United States Patent
Kallmes et al.

(10) Patent No.: US 12,420,069 B2
(45) Date of Patent: Sep. 23, 2025

(54) INTERNAL CAROTID ARTERY THROMBECTOMY DEVICES AND METHODS

(71) Applicants: Covidien LP, Mansfield, MA (US); Mayo Foundation for Medical Education and Research, Rochester, MN (US)

(72) Inventors: David F. Kallmes, Rochester, MN (US); Waleed Brinjikji, Rochester, MN (US); Brady Hatcher, Rogers, MN (US); Randy Beyreis, Rogers, MN (US)

(73) Assignees: Covidien LP, Mansfield, MA (US); Mayo Foundation for Medical Education and Research, Rochester, MN (US)

( * ) Notice: Subject to any disclaimer, the term of this patent is extended or adjusted under 35 U.S.C. 154(b) by 650 days.

(21) Appl. No.: 17/415,431

(22) PCT Filed: Dec. 18, 2019

(86) PCT No.: PCT/US2019/067074
§ 371 (c)(1),
(2) Date: Jun. 17, 2021

(87) PCT Pub. No.: WO2020/132003
PCT Pub. Date: Jun. 25, 2020

(65) Prior Publication Data
US 2022/0062597 A1    Mar. 3, 2022

Related U.S. Application Data

(60) Provisional application No. 62/781,738, filed on Dec. 19, 2018.

(51) Int. Cl.
*A61M 25/10* (2013.01)
*A61M 25/00* (2006.01)

(52) U.S. Cl.
CPC .......... *A61M 25/10* (2013.01); *A61M 25/005* (2013.01); *A61M 25/0074* (2013.01);
(Continued)

(58) Field of Classification Search
CPC ................ A61M 25/10; A61M 25/005; A61M 25/0074; A61M 25/0662; A61M 25/1006;
(Continued)

(56) References Cited

U.S. PATENT DOCUMENTS

| | | |
|---|---|---|
| 3,908,637 A | 9/1975 | Doroshow |
| 4,552,554 A | 11/1985 | Gould |

(Continued)

FOREIGN PATENT DOCUMENTS

| | | |
|---|---|---|
| CN | 1263691 A1 | 8/2000 |
| CN | 107007921 A | 8/2017 |

(Continued)

OTHER PUBLICATIONS

Extended Search Report from counterpart European Application No. 19900175.1 dated Jun. 1, 2022, 9 pp.
(Continued)

*Primary Examiner* — Katherine H Schwiker
*Assistant Examiner* — Lauren Dubose
(74) *Attorney, Agent, or Firm* — Shumaker & Sieffert, P.A.

(57) ABSTRACT

The disclosure includes a balloon guiding sheath including an elongated sheath having a proximal end, a distal end, an inner tube and an outer tube both extending between the proximal end and the distal end, an access port located adjacent the proximal end, a distal port located adjacent the distal end, and a working lumen extending through the
(Continued)

elongated sheath between the access port and the distal port. The balloon guiding sheath may include an inflatable balloon located on an outer surface of the elongated sheath adjacent the distal end, and at least one vent hole located between an outer surface of the elongated sheath and an inner surface of the inflatable balloon. The at least one vent hole may be configured to allow media to flow from the inflatable balloon to an external portion outside the balloon guiding sheath.

19 Claims, 33 Drawing Sheets

(52) U.S. Cl.
CPC ............... *A61M 2025/0079* (2013.01); *A61M 2025/105* (2013.01); *A61M 2025/1081* (2013.01)

(58) Field of Classification Search
CPC ...... A61M 25/1034; A61M 2025/0079; A61M 2025/105; A61M 2025/1081; A61M 2025/1065; A61M 2025/1093; A61M 25/10185; A61M 2210/12; A61M 2025/1086; A61M 2025/1097; A61M 2025/1077; A61M 25/1002; A61M 25/1011; A61M 2025/1043; A61M 2025/1075; A61M 2025/1013; A61B 2017/22067; A61B 2017/22094; A61B 2017/00557; A61B 1/00082; A61B 17/12136

See application file for complete search history.

(56) References Cited

U.S. PATENT DOCUMENTS

| | | | |
|---|---|---|---|
| 4,638,805 A | 1/1987 | Powell | |
| 4,654,024 A | 3/1987 | Critienden | |
| 4,771,774 A | 9/1988 | Simpson | |
| 4,841,977 A | 6/1989 | Griffith | |
| 4,857,046 A | 8/1989 | Stevens | |
| 4,926,858 A | 5/1990 | Gifford | |
| 4,955,895 A * | 9/1990 | Sugiyama | A61M 25/104 604/103.1 |
| 5,000,185 A | 3/1991 | Yock | |
| 5,047,040 A | 9/1991 | Simpson | |
| 5,085,662 A | 2/1992 | Willard | |
| 5,135,482 A | 8/1992 | Neracher | |
| 5,178,153 A | 1/1993 | Einzig | |
| 5,190,050 A | 3/1993 | Nitzsche | |
| 5,195,962 A | 3/1993 | Martin | |
| 5,201,723 A | 4/1993 | Quinn | |
| 5,263,959 A | 11/1993 | Fischell | |
| 5,312,425 A | 5/1994 | Evans | |
| 5,358,472 A | 10/1994 | Vance | |
| 5,366,464 A | 11/1994 | Belknap | |
| 5,383,460 A | 1/1995 | Jang | |
| 5,429,136 A | 7/1995 | Milo | |
| 5,431,673 A | 7/1995 | Summers | |
| 5,507,795 A | 4/1996 | Chiang | |
| 5,632,754 A | 5/1997 | Farley | |
| 5,632,755 A | 5/1997 | Nordgren | |
| 5,674,232 A | 10/1997 | Halliburton | |
| 5,681,336 A | 10/1997 | Clement | |
| 5,722,403 A | 3/1998 | McGee | |
| 5,728,065 A * | 3/1998 | Follmer | A61M 25/10 604/96.01 |
| 5,759,191 A | 6/1998 | Barbere | |
| 5,807,339 A | 9/1998 | Bostrom | |
| 5,836,957 A | 11/1998 | Schulz | |
| 5,843,050 A | 12/1998 | Jones | |
| 5,843,103 A | 12/1998 | Wulfman | |
| 5,868,778 A | 2/1999 | Gershony | |
| 5,897,537 A | 4/1999 | Berg et al. | |
| 5,904,651 A | 5/1999 | Swanson | |
| 5,935,075 A | 8/1999 | Casscells | |
| 5,951,482 A | 9/1999 | Winston | |
| 5,951,583 A | 9/1999 | Jensen | |
| 5,957,952 A | 9/1999 | Gershony | |
| 5,997,558 A | 12/1999 | Nash | |
| 6,007,530 A | 12/1999 | Dornhofer | |
| 6,010,449 A | 1/2000 | Selmon | |
| 6,017,359 A | 1/2000 | Gershony | |
| 6,022,319 A | 2/2000 | Willard et al. | |
| 6,027,514 A | 2/2000 | Stine | |
| 6,039,721 A | 3/2000 | Johnson | |
| 6,080,170 A | 6/2000 | Nash | |
| 6,106,515 A | 8/2000 | Winston | |
| 6,110,164 A | 8/2000 | Vidlund | |
| 6,120,516 A | 9/2000 | Selmon | |
| 6,134,003 A | 10/2000 | Tearney | |
| 6,143,016 A | 11/2000 | Bleam | |
| 6,168,579 B1 | 1/2001 | Tsugita | |
| 6,176,871 B1 | 1/2001 | Pathak | |
| 6,206,868 B1 | 3/2001 | Parodi | |
| 6,231,551 B1 | 5/2001 | Barbut | |
| 6,241,744 B1 | 6/2001 | Imran | |
| 6,370,030 B1 | 4/2002 | Bergstedt et al. | |
| 6,413,235 B1 | 7/2002 | Parodi | |
| 6,416,527 B1 | 7/2002 | Berg | |
| 6,451,036 B1 | 9/2002 | Heitzmann | |
| 6,454,717 B1 | 9/2002 | Pantages | |
| 6,482,216 B1 | 11/2002 | Hiblar | |
| 6,482,217 B1 | 11/2002 | Pintor | |
| 6,501,551 B1 | 12/2002 | Tearney | |
| 6,511,458 B2 | 1/2003 | Milo | |
| 6,533,753 B1 | 3/2003 | Haarstad | |
| 6,572,643 B1 | 6/2003 | Gharibadeh | |
| 6,575,995 B1 | 6/2003 | Huter | |
| 6,579,298 B1 | 6/2003 | Bruneau | |
| 6,592,557 B2 | 7/2003 | Barbut | |
| 6,615,071 B1 | 9/2003 | Casscells | |
| 6,620,148 B1 | 9/2003 | Tsugita | |
| 6,632,236 B2 | 10/2003 | Hogendijk | |
| 6,638,233 B2 | 10/2003 | Corvi | |
| 6,638,245 B2 | 10/2003 | Miller | |
| 6,645,217 B1 | 11/2003 | MacKinnon | |
| 6,648,854 B1 | 11/2003 | Patterson | |
| 6,666,874 B2 | 12/2003 | Heitzmann | |
| 6,682,505 B2 | 1/2004 | Bates | |
| 6,702,782 B2 | 3/2004 | Miller | |
| 6,719,718 B2 | 4/2004 | Bonnette et al. | |
| 6,730,063 B2 | 5/2004 | Delaney | |
| 6,758,854 B1 | 7/2004 | Butler | |
| 6,790,204 B2 | 9/2004 | Zadno-Azizi | |
| 6,796,992 B2 | 9/2004 | Barbut | |
| 6,800,085 B2 | 10/2004 | Selmon | |
| 6,818,001 B2 | 11/2004 | Wulfman | |
| 6,824,550 B1 | 11/2004 | Noriega | |
| 6,830,577 B2 | 12/2004 | Nash | |
| 6,879,851 B2 | 4/2005 | McNamara | |
| 6,902,540 B2 | 6/2005 | Dorros | |
| 6,908,474 B2 | 6/2005 | Hogendijk | |
| 6,929,634 B2 | 8/2005 | Dorros | |
| 6,960,222 B2 | 11/2005 | Vo | |
| 6,975,898 B2 | 12/2005 | Seibel | |
| 7,033,344 B2 | 4/2006 | Imran | |
| 7,063,714 B2 | 6/2006 | Dorros | |
| 7,074,231 B2 | 7/2006 | Jang | |
| 7,108,677 B2 | 9/2006 | Courtney | |
| 7,172,610 B2 | 2/2007 | Heitzmann | |
| 7,288,087 B2 | 10/2007 | Winston | |
| 7,291,146 B2 | 11/2007 | Steinke | |
| 7,445,642 B2 | 11/2008 | Amos et al. | |
| 7,458,938 B2 | 12/2008 | Patel | |
| 7,458,980 B2 | 12/2008 | Barbut | |
| 7,530,948 B2 | 5/2009 | Seibel | |
| 7,530,976 B2 | 5/2009 | MacMahon | |
| 7,538,859 B2 | 5/2009 | Tearney | |
| 7,637,885 B2 | 12/2009 | Maschke | |
| 7,645,261 B2 | 1/2010 | Hinchliffe | |

(56) References Cited

U.S. PATENT DOCUMENTS

| | | |
|---|---|---|
| 7,727,184 B2 | 6/2010 | Holmes, Jr. et al. |
| 7,729,745 B2 | 6/2010 | Maschke |
| 7,734,332 B2 | 6/2010 | Sher |
| 7,753,852 B2 | 7/2010 | Maschke |
| 7,766,049 B2 | 8/2010 | Miller |
| 7,815,590 B2 | 10/2010 | Cooper |
| 7,862,576 B2 | 1/2011 | Gurm |
| 7,909,801 B2 | 3/2011 | Hinchliffe |
| 7,938,820 B2 | 5/2011 | Vvebster |
| 7,952,718 B2 | 5/2011 | Li |
| 7,972,299 B2 | 7/2011 | Carter |
| 8,002,740 B2 | 8/2011 | Willink |
| 8,021,351 B2 | 9/2011 | Boldenow |
| 8,133,243 B2 | 3/2012 | Lupton et al. |
| 8,221,348 B2 | 7/2012 | Hackett |
| 8,252,015 B2 | 8/2012 | Leeflang |
| 8,252,219 B2 | 8/2012 | Trapp |
| 8,267,953 B2 | 9/2012 | Gurm |
| 8,313,493 B2 | 11/2012 | Fischer |
| 8,361,097 B2 | 1/2013 | Patel |
| 8,435,218 B2 | 5/2013 | Hinchliffe |
| 8,435,225 B2 | 5/2013 | Courtney |
| 8,644,913 B2 | 2/2014 | Simpson |
| 8,758,325 B2 | 6/2014 | Vvebster |
| 8,876,853 B2 | 11/2014 | Ren |
| 8,900,191 B2 | 12/2014 | Lenker |
| 8,911,459 B2 | 12/2014 | Simpson |
| 8,926,560 B2 | 1/2015 | Dinh |
| 8,945,160 B2 | 2/2015 | Krolik |
| 9,044,577 B2 | 6/2015 | Bishop |
| 9,108,017 B2 | 8/2015 | Pingleton |
| 9,119,662 B2 | 9/2015 | Moberg |
| 9,126,015 B2 | 9/2015 | Krolik |
| 9,199,058 B2 | 12/2015 | Lentz |
| 9,232,948 B2 | 1/2016 | Griffin |
| 9,351,757 B2 | 5/2016 | Kusleika |
| 9,498,247 B2 | 11/2016 | Patel |
| 9,592,075 B2 | 3/2017 | Simpson |
| 9,681,882 B2 | 6/2017 | Garrison |
| 9,757,137 B2 | 9/2017 | Krolik |
| 9,833,599 B2 | 12/2017 | Krolik |
| 9,924,957 B2 | 3/2018 | Mcguckin |
| 9,993,325 B2 | 6/2018 | Ren |
| 10,085,765 B2 | 10/2018 | Krolik et al. |
| 10,130,386 B2 | 11/2018 | Simpson |
| 10,406,329 B2 | 9/2019 | Wilson et al. |
| 2001/0020126 A1 | 9/2001 | Swanson |
| 2001/0047184 A1 | 11/2001 | Connors |
| 2002/0016565 A1 | 2/2002 | Iadno-Azizi |
| 2002/0035347 A1 | 3/2002 | Bagaoisan |
| 2002/0091407 A1 | 7/2002 | Iadno-Azizi |
| 2002/0111548 A1 | 8/2002 | Swanson |
| 2002/0115982 A1 | 8/2002 | Barbut |
| 2002/0169436 A1 | 11/2002 | Gurm |
| 2002/0169458 A1 | 11/2002 | Connors |
| 2002/0177866 A1 | 11/2002 | Weikel |
| 2002/0198491 A1 | 12/2002 | Miller et al. |
| 2002/0198492 A1 | 12/2002 | Miller et al. |
| 2003/0023204 A1 | 1/2003 | Vo |
| 2004/0002650 A1 | 1/2004 | Mandrusov |
| 2004/0049225 A1 | 3/2004 | Denison |
| 2004/0092915 A1 | 5/2004 | Levatter |
| 2004/0186368 A1 | 9/2004 | Ramzipoor |
| 2004/0260236 A1 | 12/2004 | Manning |
| 2005/0085769 A1* | 4/2005 | MacMahon ............ A61M 1/81 604/96.01 |
| 2005/0124973 A1 | 6/2005 | Dorros |
| 2005/0131453 A1 | 6/2005 | Parodi |
| 2005/0149103 A1 | 7/2005 | Connors |
| 2005/0154416 A1* | 7/2005 | Herweck ............ B29C 48/09 606/200 |
| 2005/0182295 A1 | 8/2005 | Soper |
| 2005/0187571 A1 | 8/2005 | Maschke |
| 2005/0192496 A1 | 9/2005 | Maschke |
| 2005/0203553 A1 | 9/2005 | Maschke |
| 2005/0228402 A1 | 10/2005 | Hofmann |
| 2005/0251116 A1 | 11/2005 | Steinke |
| 2005/0267323 A1 | 12/2005 | Dorros |
| 2005/0277979 A1 | 12/2005 | Dorros |
| 2006/0041228 A1 | 2/2006 | vo |
| 2006/0064009 A1 | 3/2006 | Webler |
| 2006/0064073 A1 | 3/2006 | Schonholz |
| 2006/0100706 A1 | 5/2006 | Shadduck |
| 2006/0135870 A1 | 6/2006 | Webler |
| 2006/0173475 A1 | 8/2006 | Lafontaine |
| 2006/0200191 A1 | 9/2006 | Zadno-Azizi |
| 2006/0229659 A1 | 10/2006 | Gifford |
| 2007/0015969 A1 | 1/2007 | Feldman |
| 2007/0015979 A1 | 1/2007 | Redel |
| 2007/0038061 A1 | 2/2007 | Huennekens |
| 2007/0088230 A1 | 4/2007 | Terashi |
| 2007/0106320 A1 | 5/2007 | Blix |
| 2007/0135712 A1 | 6/2007 | Maschke |
| 2007/0219484 A1 | 9/2007 | Straub |
| 2007/0225750 A1 | 9/2007 | Ren |
| 2007/0270740 A1 | 11/2007 | Holmes |
| 2007/0288036 A1 | 12/2007 | Seshadri |
| 2007/0299309 A1 | 12/2007 | Seibel |
| 2008/0004643 A1 | 1/2008 | To |
| 2008/0004644 A1 | 1/2008 | To |
| 2008/0004645 A1 | 1/2008 | To |
| 2008/0004646 A1 | 1/2008 | To |
| 2008/0015491 A1 | 1/2008 | Bei |
| 2008/0045986 A1 | 2/2008 | To |
| 2008/0058629 A1 | 3/2008 | Seibel |
| 2008/0139897 A1 | 6/2008 | Ainsworth |
| 2008/0147000 A1 | 6/2008 | Seibel |
| 2008/0177138 A1 | 7/2008 | Courtney |
| 2008/0188793 A1 | 8/2008 | Kozak |
| 2008/0243030 A1 | 10/2008 | Seibel |
| 2008/0243031 A1 | 10/2008 | Seibel |
| 2008/0312637 A1 | 12/2008 | Miller |
| 2009/0018565 A1 | 1/2009 | To |
| 2009/0018566 A1 | 1/2009 | Escudero |
| 2009/0018567 A1 | 1/2009 | Escudero |
| 2009/0024085 A1 | 1/2009 | To |
| 2009/0030400 A1 | 1/2009 | Bose |
| 2009/0062837 A1 | 3/2009 | Gasche |
| 2009/0198172 A1 | 8/2009 | Garrison |
| 2009/0221920 A1 | 9/2009 | Boppart |
| 2009/0264826 A1 | 10/2009 | Thompson |
| 2009/0287186 A1 | 11/2009 | Adams |
| 2009/0299282 A1 | 12/2009 | Lau |
| 2009/0306597 A1 | 12/2009 | Lupton |
| 2009/0318862 A1 | 12/2009 | Ali |
| 2010/0049225 A1 | 2/2010 | To |
| 2010/0125253 A1 | 5/2010 | Olson |
| 2010/0193106 A1 | 8/2010 | Trapp |
| 2010/0204712 A1 | 8/2010 | Mallaby |
| 2010/0204724 A1 | 8/2010 | Hogendijk |
| 2010/0324472 A1 | 12/2010 | Wulfman |
| 2011/0004107 A1 | 1/2011 | Rosenthal |
| 2011/0004147 A1 | 1/2011 | Renati |
| 2011/0034986 A1 | 2/2011 | Chou |
| 2011/0092955 A1 | 4/2011 | Purdy |
| 2011/0172699 A1 | 7/2011 | Miller |
| 2011/0201924 A1 | 8/2011 | Tearney |
| 2011/0245775 A1 | 10/2011 | Tekulve |
| 2011/0301625 A1 | 12/2011 | Mauch |
| 2012/0004506 A1 | 1/2012 | Tearney |
| 2012/0116350 A1 | 5/2012 | Strauss |
| 2012/0259375 A1 | 10/2012 | Druma |
| 2012/0289971 A1 | 11/2012 | Segermark et al. |
| 2012/0302994 A1 | 11/2012 | Wilson et al. |
| 2012/0330350 A1 | 12/2012 | Jones |
| 2013/0023802 A1* | 1/2013 | McIntosh ............ A61M 25/10 601/2 |
| 2013/0035628 A1 | 2/2013 | Garrison et al. |
| 2013/0138128 A1 | 5/2013 | Patel |
| 2013/0281788 A1 | 10/2013 | Garrison |
| 2014/0107575 A1 | 4/2014 | Miller |
| 2014/0128893 A1 | 5/2014 | Guggenheimer |
| 2014/0213893 A1 | 7/2014 | Simpson |
| 2014/0257311 A1 | 9/2014 | Druma |

(56) References Cited

U.S. PATENT DOCUMENTS

| | | |
|---|---|---|
| 2014/0296769 A1 | 10/2014 | Hyde |
| 2014/0371718 A1 | 12/2014 | Alvarez |
| 2015/0051625 A1 | 2/2015 | Petrucci |
| 2015/0057639 A1* | 2/2015 | Storbeck ............ A61M 25/005 264/171.27 |
| 2015/0202416 A1 | 7/2015 | Krolik |
| 2015/0208922 A1 | 7/2015 | Simpson |
| 2015/0359547 A1 | 12/2015 | Vale |
| 2016/0144155 A1 | 5/2016 | Simpson |
| 2016/0271376 A1 | 9/2016 | Godin et al. |
| 2016/0338720 A1 | 11/2016 | Kassab |
| 2017/0065293 A1 | 3/2017 | Rosenthal |
| 2017/0065295 A1 | 3/2017 | Patel |
| 2017/0105743 A1 | 4/2017 | Vale |
| 2017/0143938 A1 | 5/2017 | Ogle |
| 2017/0238808 A1 | 8/2017 | Simpson |
| 2017/0273711 A1 | 9/2017 | Simpson |
| 2017/0274189 A1 | 9/2017 | Smith et al. |
| 2017/0333048 A1 | 11/2017 | Krieger |
| 2018/0015265 A1* | 1/2018 | Jamous ................ B29C 65/16 |
| 2018/0042520 A1 | 2/2018 | Patel |
| 2018/0103974 A1 | 4/2018 | Osborne |
| 2018/0146978 A1 | 5/2018 | Patel |
| 2018/0192880 A1 | 7/2018 | Patel |
| 2018/0193042 A1 | 7/2018 | Wilson |
| 2019/0008534 A1 | 1/2019 | Garrison |
| 2019/0021759 A1 | 1/2019 | Krolik et al. |
| 2019/0046218 A1 | 2/2019 | Garrison |
| 2019/0167287 A1 | 6/2019 | Vale |
| 2019/0262590 A1 | 8/2019 | Tummala |
| 2020/0246036 A1 | 8/2020 | Kallmes et al. |
| 2021/0346039 A1 | 11/2021 | Kallmes et al. |

FOREIGN PATENT DOCUMENTS

| | | |
|---|---|---|
| CN | 108882841 A | 11/2018 |
| EP | 0808638 A1 | 11/1997 |
| EP | 1859732 A1 | 11/2007 |
| EP | 2353526 B1 | 9/2013 |
| JP | 2000217923 A | 8/2000 |
| JP | 2002214127 A | 7/2002 |
| JP | 2007533361 A | 11/2007 |
| JP | 2011530353 A | 12/2011 |
| JP | 2013005974 A | 1/2013 |
| JP | 2016508758 A | 3/2016 |
| RU | 2185859 C2 | 7/2002 |
| RU | 2218191 C2 | 12/2003 |
| WO | 0176680 A1 | 10/2001 |
| WO | 0191844 A1 | 12/2001 |
| WO | 0249690 | 6/2002 |
| WO | 03061457 A2 | 7/2003 |
| WO | 2006133030 A2 | 12/2006 |
| WO | 2007041542 A2 | 4/2007 |
| WO | 2008005888 A2 | 1/2008 |
| WO | 2009005779 A1 | 1/2009 |
| WO | 2009148317 A1 | 12/2009 |
| WO | 2010017537 A2 | 2/2010 |
| WO | 2010039464 A1 | 4/2010 |
| WO | 2010056771 A1 | 5/2010 |
| WO | 2011044387 A2 | 4/2011 |
| WO | 2014204860 A1 | 12/2014 |
| WO | 2015120146 A1 | 8/2015 |
| WO | 2017008917 A1 | 1/2017 |
| WO | 2017008918 A1 | 1/2017 |
| WO | 2017192999 A1 | 11/2017 |
| WO | 2018033401 A1 | 2/2018 |
| WO | 2018132387 A1 | 7/2018 |
| WO | 2018145212 A1 | 8/2018 |
| WO | 2020018653 A1 | 1/2020 |
| WO | 2020132003 A1 | 6/2020 |

OTHER PUBLICATIONS

Final Rejection, and translation thereof, from counterpart Japanese Application No. 2018-558196 dated Dec. 16, 2021, 10 pp.

Prosecution History from U.S. Appl. No. 16/319,764 dated Mar. 16, 2021 through Aug. 16, 2022, 109 pp.

Aziz et al., "Chronic total occlusions—a stiff challenge requiring a major breakthrough: is there light at the end of the tunnel?," Heart; vol. 91, Jun. 2005, 7 pp.

NCBI., "Stentoplasty effectiveness and safety for the treatment of osteoporotic vertebral fractures: a systematic review," National Center for Biotechnology Information; Sep. 2015; Downloaded on Feb. 17, 2019 from https://www.cbi.nlm.nih.gov/pubmed/26194207, 2 pp.

Neuroangio, "Internal Carotid Artery and Its Aneurysms," Downloaded on Mar. 12, 2018 from http://neuroangio.organatomy-and-variants/internal-carotid-artery-and-its-aneurysms/, 84 pp.

Parodi et al., "Initial 200 cases of carotid artery stenting using a reversal-of-flow cerebral protection device," Journal of Cardiovascular Surgery; Research Gate; 2007; vol. 48; No. 2; Downloaded on Jun. 8, 2018 from https://www.researchgate.net/6412060_Initial_200_cases_of_carotid_arterty_stenting_using_a_reveral-of-flow_cerebral_protection_device/links/00463538c71bae60cc000000/Initial-200-cases-0f-carotid-artery-stenting-using-, 8 pp.

Shinkle et al., "Evaluation of stent placement and outcomes with optical coherence tomography," Interventional Cardiology, vol. 2, Issue 4, Aug. 2010, ISSN 1755-5302, 9 pp.

International Search Report and Written Opinion of International Application No. PCT/US2019/67074, mailed Mar. 10, 2020, 7 pp.

International Preliminary Report on Patentability from International Application No. PCT/US2019/67074, mailed Jun. 16, 2021, 6 pp.

Prosecution History from U.S. Appl. No. 16/319,764, dated Jan. 22, 2019 through Nov. 5, 2021, 65 pp.

Notice of Reasons for Rejection, and translation thereof, from counterpart Japanese Application No. 2018-558196 dated Oct. 13, 2022, 16 pp.

Office Action from U.S. Appl. No. 17/283,467 dated Apr. 25, 2023, 13 pp.

Notification of Rejection, and English translation thereof, from Japanese Application No. 2018-558196, dated Feb. 9, 2021, 8 pp.

* cited by examiner

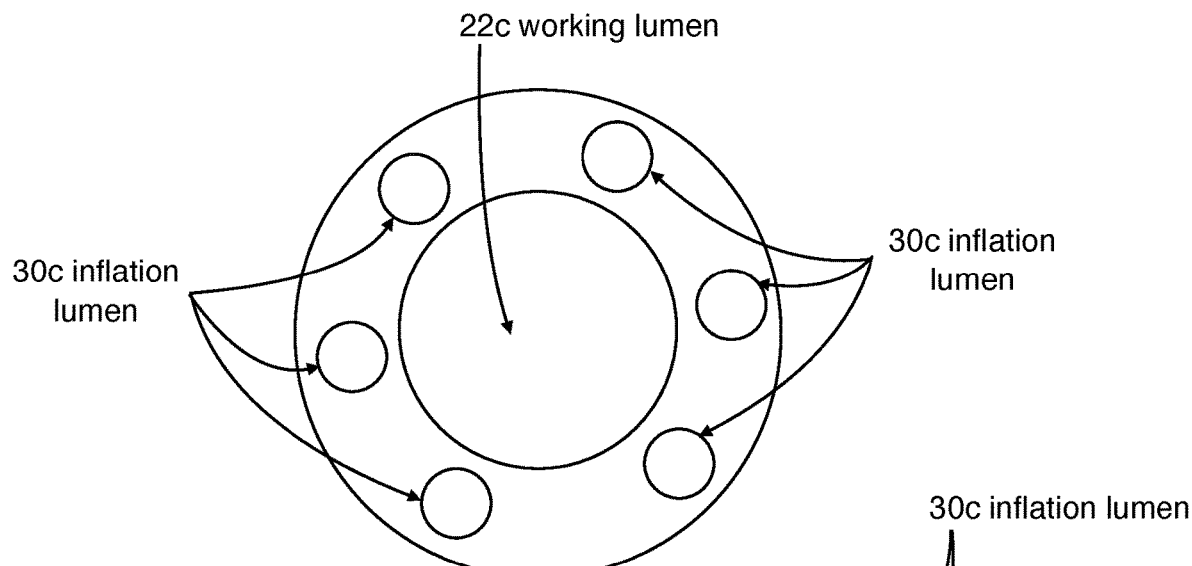
Fig. 13A
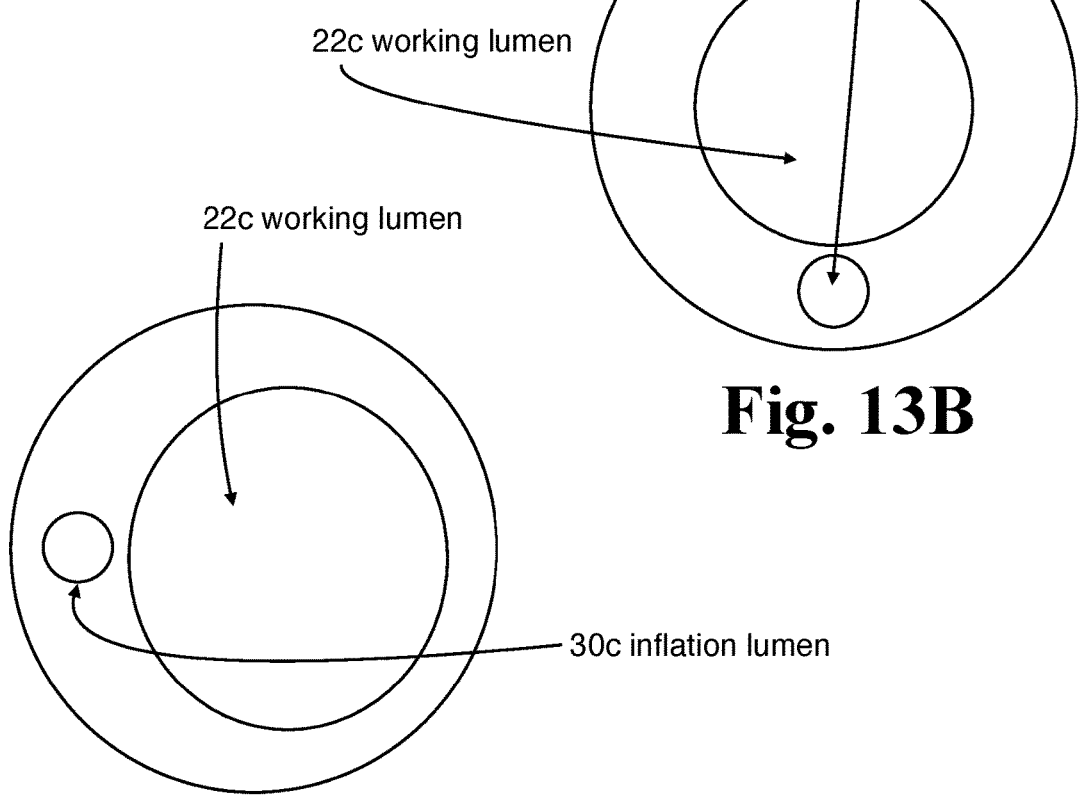
Fig. 13B
Fig. 13C

INTERNAL CAROTID ARTERY THROMBECTOMY DEVICES AND METHODS

CROSS REFERENCE TO RELATED APPLICATION

This application claims the benefit and priority of U.S. Provisional Patent Application No. 62/781,738; filed Dec. 19, 2018; and entitled INTERNAL CAROTID ARTERY THROMBECTOMY DEVICES AND METHODS; the entire contents of which are incorporated herein by reference.

The entire contents of the following application are incorporated by reference herein: International Patent Application PCT/US2017/031311; having an international filing date of May 5, 2017 and a priority date of May 6, 2016; and entitled INTERNAL CAROTID ARTERY THROMBECTOMY DEVICES AND METHODS.

BACKGROUND

Field of Invention

The invention relates generally to medical devices and methods of use. Embodiments of the invention include devices for performing thrombectomy or embolectomy in the internal carotid artery and other vessels of a patient.

Description of Related Art

Acute Ischemic Stroke (AIS) can be caused by thrombus, embolus or other occlusions in regions of the internal carotid artery (ICA) such as the Petrous part, Cavernous part or Cerebral part. Approaches for performing thrombectomy or embolectomy to treat AIS include positioning a balloon guiding catheter in the carotid artery at a location upstream from the occlusion, typically at a proximal location in the artery such as the cervical part. After the balloon is inflated to provide antegrade blood flow cessation, suction can be applied to the catheter to retrieve the embolus. Thrombectomy tools such as stent retrievers can also be delivered directly to the embolus through the guiding catheter to break up the embolus and enhance the retrieval process.

These thrombectomy procedures may involve placing a sheath through an arteriotomy in the patient's common femoral artery, and delivering the guiding catheter to the ICA through the sheath. For example, an 8-9 French (Fr) inner diameter (ID) (0.015-0.118 inches) sheath having a length on the order of twenty-five centimeters can be used to provide the access to the arterial tree through the arteriotomy. A balloon guiding catheter having a 7-8 Fr outer diameter (OD) (0.092-0.105 inches), commonly about ninety centimeters in length, can then be delivered to the ICA through the sheath. A 10-11 Fr (0.131-0.144 inch) arteriotomy may be required for the sheath during procedures of these types. Unfortunately these relatively large arteriotomies can enhance the risk of bleeding, especially since patient's undergoing these procedures may be receiving thrombolytics that may increase the risks of hemorrhagic complications.

Relatively small diameter distal access aspiration catheters (e.g., up to about 0.087 inch OD) are sometimes used during thrombectomy in the ICA. Such distal aspiration catheters include the ACE 68 from Penumbra, Inc. and the Sophia Plus from Microvention, Inc. For example, during these procedures the distal aspiration catheter can inserted with the end positioned at the distal middle cerebral artery. Other thrombecotomy tools such as stent retrievers are sometimes delivered to the intracranial vasculature through distal access catheters used in this manner. However, balloon guiding catheters have IDs that are too small to accommodate these distal aspiration catheters. Other known balloon guide catheters include the MO.MA Ultra and Cello devices from Medtronic, Inc., and the Flowgate2 device from Stryker Neurovascular. The relatively long period of time required to place a sheath and then a balloon guide catheter can detract from the benefits of this treatment.

Stents and other endovascular tools are sometimes placed in the ICA or other vasculature using guiding sheaths that do not have balloons. Guiding sheaths are typically about ninety centimeters in length. These devices act as a combination of access sheath and guiding catheter. The need for a separate sheath is obviated by the use of these guiding sheaths since they are sufficiently long to provide access to the target vessel. Although guiding sheaths do not provide arterial occlusion, they can be rapidly placed.

There is a continuing need for improved devices and methods for performing mechanical revascularization such as thrombectomy and embolectomy in the ICA and other vasculature. In particular, there is a need for such devices and methods that provide enhanced efficacy. Devices and methods of these types that can improve the efficiency of health care delivery would be especially desirable.

SUMMARY

The present disclosure describes a balloon guiding sheath that includes an elongated sheath having a proximal end, a distal end, a proximal portion defining a first outer diameter, and a distal portion defining a second outer diameter. The balloon guiding sheath may include an access port located on the proximal end, a distal port located on the distal end, a working lumen extending through the elongated sheath between the access port and the distal port, an inflation port on the proximal end, an inflatable balloon coupled to the distal end, and an inflation lumen extending in the elongated sheath between the inflation port and the balloon. The elongated sheath may be sized and configured to enable direct insertion into a patient's vasculature through an arteriotomy in the patient's femoral artery to position the balloon at a target site.

The first outer diameter may be greater than the second outer diameter. In some embodiments, the first outer diameter is approximately equal to 0.123 inches. However, in some embodiments, the first outer diameter is approximately equal to 0.137 inches. Additionally, in some embodiments, the second outer diameter is approximately equal to 0.104 inches such that the elongated sheath fits through an 8 Fr opening. Even still, in some embodiments, the second outer diameter is approximately equal to 0.124 inches such that the elongated sheath fits through a 10 Fr opening.

The distal portion of the elongated sheath may include an inner tube and an outer tube that surrounds the inner tube. Furthermore, the distal portion of the elongated sheath may include a reinforcement layer located between the inner tube and the outer tube. The reinforcement layer arranged and configured to enable flow of at least one of fluid and media through the inflation lumen.

The inflation lumen may include a proximal inflation lumen extending from the inflation port to a middle portion located between the proximal portion and the distal portion. The inflation lumen may also include a distal inflation lumen extending from the middle portion to the balloon, whereby the distal inflation lumen is located between the inner tube and the outer tube.

In some embodiments, the proximal portion of the working lumen defines a first inner diameter approximately equal to 0.090 inches. In some embodiments, the first inner diameter is greater than or equal to 0.101 inches and less than or equal to 0.113 inches. In some embodiments, the first inner diameter is approximately equal to 0.113 inches.

Additionally, the distal portion of the working lumen may define a second inner diameter greater than or equal to 0.087 inches and less than or equal to 0.090 inches. In some embodiments, the second inner diameter greater than or equal to 0.101 inches and less than or equal to 0.113 inches. In some embodiments, the second inner diameter is approximately equal to 0.101 inches.

In some embodiments, the working lumen defines an inner diameter extending from the proximal end to the distal end. The inner diameter may be approximately equal to 0.088 inches. The proximal portion of the working lumen may equal approximately 85 centimeters in length. The distal portion of the working lumen may equal approximately 10 centimeters in length. The elongated sheath may define a working length approximately equal to 95 centimeters.

Furthermore, in some embodiments, the working length is long enough to enable the distal end to reach at least a cervical portion of a patient's internal carotid artery from the femoral artery. Even still, in some embodiments, the working length is long enough to enable the distal end to reach at least a petrous portion of a patient's internal carotid artery from the femoral artery. As well, in some embodiments, the working length is long enough to enable the distal end to reach at least a cavernous portion of a patient's internal carotid artery from the femoral artery.

In some embodiments, the balloon extends around and beyond a distal tip of the elongated sheath and defines a funnel-shaped opening into the distal port when the balloon is in an inflated state such that the balloon does not occlude the working lumen of the distal port. The elongated sheath may be arranged and configured to have sufficient stiffness and tip flexibility to enable insertion of the working length of the sheath into a patient's vasculature through an arteriotomy in the patient's carotid artery to position the distal port at a target site in at least one of a petrous portion of a patient's internal carotid artery, a cavernous portion of a patient's internal carotid artery, and a cerebral portion of a patient's internal carotid artery.

The disclosure also includes a balloon guiding sheath that comprises an elongated sheath having a proximal end, a distal end, a proximal portion defining a first outer diameter, and a distal portion defining a second outer diameter. The balloon guiding sheath may also include an access port located on the proximal end, a distal port located on the distal end, a working lumen extending through the elongated sheath between the access port and the distal port, an inflation port on the proximal end, an inflatable balloon coupled to the distal end, and an inflation lumen extending through the elongated sheath between the inflation port and the balloon. The inflation lumen may comprise a distal inflation port extending through an endwall of the elongated sheath, wherein the inflation lumen is not in fluid communication with the working lumen between the access port and the distal port. The elongated sheath may be sized and configured to enable direct insertion into a patient's vasculature through an arteriotomy in the patient's femoral artery to position the balloon at a target site. In some embodiments, the first outer diameter is greater than the second outer diameter.

In some embodiments, the balloon guiding sheath comprises a first inflation hole extending from the inflation lumen through a sidewall of the elongated sheath, wherein when a guide wire is inserted into the inflation lumen and out through the distal inflation port, the distal inflation port thereby creates a seal against the guide wire. Additionally, the inflation lumen may be arranged and configured to enable flow of at least one of fluid and media through the inflation lumen into the first inflation hole and into the balloon to thereby inflate the balloon.

In some embodiments, the inflation lumen is a first inflation lumen. The balloon guiding sheath may further comprise a second inflation lumen extending through the elongated sheath between the inflation port and the balloon. The second inflation lumen may comprise a second distal inflation port extending through the endwall of the elongated sheath, wherein the second inflation lumen is not in fluid communication with the working lumen between the access port and the distal port. The balloon guiding sheath may also include a second inflation hole extending from the second inflation lumen through the sidewall of the elongated sheath, wherein when a second guide wire is inserted into the second inflation lumen and out through the second distal inflation port, the second distal inflation port thereby creates a seal against the second guide wire. The second inflation lumen may be arranged and configured to enable flow of at least one of fluid and media through the second inflation lumen into the second inflation hole and into the balloon to thereby inflate the balloon.

The elongated sheath may define a central axis extending from the proximal end to the distal end, wherein at least a portion of the working lumen overlaps the central axis of the elongated sheath, and wherein the inflation lumen does not overlap the central axis of the elongated sheath. In some embodiments, the elongated sheath does not have a generally constant outer diameter along its working length.

The elongated sheath may define a working length long enough to enable the distal end to reach at least a cervical portion of a patient's internal carotid artery from the carotid artery. In some embodiments, the working length is long enough to enable the distal end to reach a cavernous portion of the patient's internal carotid artery from the femoral artery. Even still, in some embodiments, the elongated sheath is arranged and configured to have sufficient stiffness and tip flexibility to enable insertion of the working length of the sheath into a patient's vasculature through an arteriotomy in the patient's carotid artery to position the distal port at a target site in at least one of a petrous portion of a patient's internal carotid artery, a cavernous portion of the patient's internal carotid artery, and a cerebral portion of the patient's internal carotid artery.

The disclosure also includes a method for using a balloon guiding sheath comprising an elongated sheath having a proximal end, a distal end, a proximal portion defining a first outer diameter, and a distal portion defining a second outer diameter that is less than the first outer diameter, the guiding sheath including an access port located on the proximal end, a distal port located on the distal end, a working lumen extending through the elongated sheath between the access port and the distal port, an inflation port on the proximal end, an inflatable balloon coupled to the distal end, and an inflation lumen extending in the elongated sheath between the inflation port and the balloon. The method may include inserting the guiding sheath directly into a patient's vasculature through an arteriotomy in a patient's femoral artery, advancing the guiding sheath through the patient's vasculature and positioning the distal end in a target site of a patient's internal carotid artery, and inflating the balloon via the inflation lumen. The target site may be a cervical portion of the internal carotid artery, a petrous portion of the internal carotid artery, and/or a cavernous portion of the internal carotid artery.

Methods may include applying relatively low pressure to the access port to suction an embolus, deflating the balloon, and withdrawing the guiding sheath through the arteriotomy in the carotid artery. Methods may also include inserting a tool into the guiding sheath through the access port after positioning the distal end at the target site, advancing the tool through the guiding sheath, actuating the tool to retrieve an embolus, withdrawing the tool from the guiding sheath, deflating the balloon, and withdrawing the guiding sheath through the arteriotomy in the carotid artery.

The distal portion of the elongated sheath may comprise an inner tube and an outer tube that surrounds the inner tube. The inflation lumen may comprise a proximal inflation lumen extending from the inflation port to a middle portion located between the proximal portion and the distal portion, and a distal inflation lumen extending from the middle portion to the balloon. The distal inflation lumen may be located between the inner tube and the outer tube.

In some embodiments, inflating the balloon via the inflation lumen occurs in response to: inserting a guide wire into the working lumen, and sealing an outer surface of the guide wire against an inner surface of the working lumen adjacent the distal port. The elongated sheath further may comprise at least one inflation hole extending from the working lumen through a sidewall of the elongated sheath. In such embodiments, the method may include flowing at least one of fluid and media through a space within the inflation lumen between the guide wire and an inner surface of the inflation lumen and into the at least one inflation hole and into the balloon to thereby inflate the balloon.

Methods may also include removing the guide wire from the working lumen. In response to removing the guide wire from the working lumen, methods may include deflating the balloon.

The disclosure may also include a balloon guiding sheath that includes an elongated sheath having a proximal end, a distal end, a proximal portion defining a first outer diameter, and a distal portion defining a second outer diameter; an access port located on the proximal end; a distal port located on the distal end; a working lumen extending through the elongated sheath between the access port and the distal port; an inflation port on the proximal end; an inflatable balloon coupled to the distal end; and an inflation lumen extending in the elongated sheath between the inflation port and the balloon. The elongated sheath may be sized and configured to enable direct insertion into a patient's vasculature through an arteriotomy in the patient's femoral artery to position the balloon at a target site.

The first outer diameter may be greater than the second outer diameter. In some embodiments, the distal portion of the elongated sheath comprises an inner tube and an outer tube that surrounds the inner tube. The distal portion of the elongated sheath may include a reinforcement layer located between the inner tube and the outer tube, the reinforcement layer arranged and configured to enable flow of at least one of fluid and media through the inflation lumen.

The inflation lumen may comprise a proximal inflation lumen extending from the inflation port to a middle portion located between the proximal portion and the distal portion.

The inflation lumen may also include a distal inflation lumen extending from the middle portion to the balloon, the distal inflation lumen located between the inner tube and the outer tube.

In some embodiments, the first outer diameter is approximately equal to 0.123 inches. Yet, in some embodiments, the second outer diameter is approximately equal to 0.104 inches such that the elongated sheath fits through an 8 Fr opening. Even still, in some embodiments, the proximal portion of the working lumen defines a first inner diameter approximately equal to 0.090 inches. Furthermore, in some embodiments, the distal portion of the working lumen defines a second inner diameter greater than or equal to 0.087 inches and less than or equal to 0.090 inches.

The working lumen may define an inner diameter extending from the proximal end to the distal end. In some embodiments, the inner diameter is approximately equal to 0.088 inches. The elongated sheath may define a working length approximately equal to 95 centimeters. In some embodiments, the proximal portion of the working lumen may equal approximately 85 centimeters in length, and the distal portion of the working lumen may equal approximately 10 centimeters in length.

In some embodiments, the first outer diameter is approximately equal to 0.137 inches, and the second outer diameter is approximately equal to 0.124 inches such that the elongated sheath fits through a 10 Fr opening. As well, in some embodiments, the proximal portion of the working lumen defines a first inner diameter greater than or equal to 0.101 inches and less than or equal to 0.113 inches, and the distal portion of the working lumen defines a second inner diameter greater than or equal to 0.101 inches and less than or equal to 0.113 inches. In some embodiments, the first inner diameter is approximately equal to 0.113 inches and the second inner diameter is approximately equal to 0.101 inches.

In some embodiments, the elongated sheath defines a working length that is long enough to enable the distal end to reach at least a cervical portion of a patient's internal carotid artery from the femoral artery. In some embodiments, the elongated sheath defines a working length that is long enough to enable the distal end to reach at least a petrous portion of a patient's internal carotid artery from the femoral artery. The working length may also be long enough to enable the distal end to reach at least a cavernous portion of a patient's internal carotid artery from the femoral artery.

The balloon may extend around and beyond a distal tip of the elongated sheath and define a funnel-shaped opening into the distal port when the balloon is in an inflated state such that the balloon does not occlude the working lumen of the distal port. Additionally, in some embodiments, the elongated sheath is arranged and configured to have sufficient stiffness and tip flexibility to enable insertion of the working length of the sheath into a patient's vasculature through an arteriotomy in the patient's carotid artery to position the distal port at a target site in at least one of a petrous portion of a patient's internal carotid artery, a cavernous portion of a patient's internal carotid artery, and a cerebral portion of a patient's internal carotid artery.

The disclosure also includes a balloon guiding sheath that includes an elongated sheath having a proximal end, a distal end, a proximal portion defining a first outer diameter, and a distal portion defining a second outer diameter; an access port located on the proximal end; a distal port located on the distal end; a working lumen extending through the elongated sheath between the access port and the distal port; an inflation port on the proximal end; an inflatable balloon coupled to the distal end; and an inflation lumen extending through the elongated sheath between the inflation port and the balloon, the inflation lumen comprising a distal inflation port extending through an endwall of the elongated sheath, wherein the inflation lumen is not in fluid communication with the working lumen between the access port and the distal port. In such embodiments, the elongated sheath is sized and configured to enable direct insertion into a patient's vasculature through an arteriotomy in the patient's femoral artery to position the balloon at a target site.

In some embodiments, the balloon guiding sheath includes a first inflation hole extending from the inflation lumen through a sidewall of the elongated sheath, wherein when a guide wire is inserted into the inflation lumen and out through the distal inflation port, the distal inflation port thereby creates a seal against the guide wire. The inflation lumen may thereby be arranged and configured to enable flow of at least one of fluid and media through the inflation lumen into the first inflation hole and into the balloon to thereby inflate the balloon.

In some embodiments, the inflation lumen is a first inflation lumen, and the balloon guiding sheath further includes a second inflation lumen extending through the elongated sheath between the inflation port and the balloon, the second inflation lumen comprising a second distal inflation port extending through the endwall of the elongated sheath, wherein the second inflation lumen is not in fluid communication with the working lumen between the access port and the distal port; and a second inflation hole extending from the second inflation lumen through the sidewall of the elongated sheath, wherein when a second guide wire is inserted into the second inflation lumen and out through the second distal inflation port, the second distal inflation port thereby creates a seal against the second guide wire. The second inflation lumen may be arranged and configured to enable flow of at least one of fluid and media through the second inflation lumen into the second inflation hole and into the balloon to thereby inflate the balloon.

The elongated sheath may define a central axis extending from the proximal end to the distal end, wherein at least a portion of the working lumen overlaps the central axis of the elongated sheath, and wherein the inflation lumen does not overlap the central axis of the elongated sheath. In some embodiments, the elongated sheath does not have a generally constant outer diameter along its working length.

Even still, in some embodiments, the elongated sheath defines a working length long enough to enable the distal end to reach at least a cervical portion of a patient's internal carotid artery from the carotid artery. In some embodiments, the working length is long enough to enable the distal end to reach a cavernous portion of the patient's internal carotid artery from the femoral artery.

The elongated sheath may be arranged and configured to have sufficient stiffness and tip flexibility to enable insertion of the working length of the sheath into a patient's vasculature through an arteriotomy in the patient's carotid artery to position the distal port at a target site in at least one of a petrous portion of a patient's internal carotid artery, a cavernous portion of the patient's internal carotid artery, and a cerebral portion of the patient's internal carotid artery.

In many embodiments, the balloon guiding sheath includes at least one vent hole located between an outer surface of the elongated sheath and an inner surface of the inflatable balloon. The at least one vent hole may allow media to flow from the inflatable balloon to an external portion outside the balloon guiding sheath. The at least one vent hole may be located along a proximal edge of the inflatable balloon.

In some embodiments, the at least one vent hole comprises a first vent hole and a second vent hole radially spaced from the first vent hole. The first vent hole may be located opposite the second vent hole along the elongated sheath.

The disclosure also includes a method for using a balloon guiding sheath. Methods may include venting, via at least one vent hole, media from an inflatable balloon to an external portion located outside the balloon guiding sheath. Methods may also include inserting the guiding sheath directly into a patient's vasculature through an arteriotomy in a patient's femoral artery and advancing the guiding sheath through the patient's vasculature and positioning the distal end in a target site of a patient's internal carotid artery. Even still, methods may include inflating the balloon via the inflation lumen. In some embodiments, the target site is a cervical portion of the internal carotid artery. Yet, in some embodiments, the target site is a petrous portion of the internal carotid artery. Even still, in some embodiments, the target site is a cavernous portion of the internal carotid artery.

In some embodiments, the method includes applying relatively low pressure to the access port to suction an embolus; deflating the balloon; and/or withdrawing the guiding sheath through the arteriotomy in the carotid artery. In some embodiments, the method includes inserting a tool into the guiding sheath through the access port after positioning the distal end at the target site; advancing the tool through the guiding sheath; actuating the tool to retrieve an embolus; withdrawing the tool from the guiding sheath; deflating the balloon; and/or withdrawing the guiding sheath through the arteriotomy in the carotid artery.

In some embodiments, inflating the balloon via the inflation lumen occurs in response to: inserting a guide wire into the working lumen; and/or sealing an outer surface of the guide wire against an inner surface of the working lumen adjacent the distal port. Methods may include flowing at least one of fluid and media through a space within the inflation lumen between the guide wire and an inner surface of the inflation lumen and into the at least one inflation hole and into the balloon to thereby inflate the balloon.

In some embodiments, the method includes removing the guide wire from the working lumen. In response to removing the guide wire from the working lumen, methods may include deflating the balloon.

The disclosure also includes a balloon guiding sheath, comprising: an elongated sheath having a proximal end, a distal end opposite the proximal end, an inner tube extending between the proximal end and the distal end, an outer tube surrounding the inner tube and extending between the proximal end and the distal end, an access port located adjacent the proximal end, a distal port located adjacent the distal end, and a working lumen extending through the elongated sheath between the access port and the distal port; an inflatable balloon located on an outer surface of the elongated sheath adjacent the distal end, the inflatable balloon being fluidly coupled to an inflation lumen extending between the inflatable balloon and an inflation port located adjacent the proximal end; and at least one vent hole located between an outer surface of the elongated sheath and an inner surface of the inflatable balloon, wherein the at least one vent hole allows media to flow from the inflatable balloon to an external portion outside the balloon guiding sheath.

In some embodiments, the elongated sheath is sized and configured to enable insertion into a patient's vasculature through an arteriotomy in a patient's radial artery to position the inflatable balloon at a target site. The insertion site may be referred to as transradial arterial access.

In some embodiments, the at least one vent hole is located along a proximal side of the inflatable balloon. Even still, in some embodiments, the at least one vent hole is located along a proximal edge of the inflatable balloon.

In some embodiments, the at least one vent hole comprises a first vent hole and a second vent hole radially spaced from the first vent hole. Furthermore, in some embodiments, the first vent hole is located opposite the second vent hole along the elongated sheath.

In some embodiments, the balloon guiding sheath further comprises a reinforcement layer located between the inner tube and the outer tube, the reinforcement layer arranged and configured to enable flow of at least one of fluid and media through the inflation lumen.

In some embodiments, the elongated sheath defines a working length comprising a proximal portion located distal the proximal end, and a distal portion located between the proximal portion and the distal end, and the elongated sheath defines a generally constant outer diameter from the proximal portion to the distal portion.

In some embodiments, the generally constant outer diameter is equal to 0.123 inches. Additionally, in some embodiments, the generally constant outer diameter is equal to 0.110 inches. Even still, in some embodiments, the generally constant outer diameter is equal to 0.102 inches.

In some embodiments, the elongated sheath defines a working length comprising a proximal portion located distal the proximal end, and a distal portion located between the proximal portion and the distal end, and the elongated sheath defines a generally constant inner diameter from the proximal portion to the distal portion.

In some embodiments, the generally constant inner diameter is equal to 0.103 inches. As well, in some embodiments, the generally constant inner diameter is equal to 0.088 inches. Even still, in some embodiments, the generally constant inner diameter is equal to 0.087 inches.

Additionally, in some embodiments, the elongated sheath defines a working length comprising a proximal portion located distal the proximal end, and a distal portion located between the proximal portion and the distal end, and the elongated sheath defines an outer diameter that tapers downward from the proximal portion to the distal portion.

In some embodiments, the inflatable balloon is located in a non-recessed portion of the outer surface. In some embodiments, the working length is long enough to enable the distal port to reach a cavernous portion of a patient's internal carotid artery from the radial artery.

In some embodiments, the elongated sheath is arranged and configured to have sufficient stiffness and tip flexibility to enable insertion of the working length of the sheath into a patient's vasculature through an arteriotomy in a patient's radial artery to position the distal port at a target site in at least one of a petrous portion of a patient's internal carotid artery, a cavernous portion of the patient's internal carotid artery, and a cerebral portion of the patient's internal carotid artery.

Other objects and advantages of the embodiments herein will become readily apparent from the following detailed description taken in conjunction with the accompanying drawings. The embodiments described above include many optional features and aspects. Features and aspects of the embodiments can be combined.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

FIGS. 13A, 13B, and 13C illustrate cross-sectional views of section 13-13 of the balloon guiding sheath, according to some embodiments.

DETAILED DESCRIPTION

Figure 1:
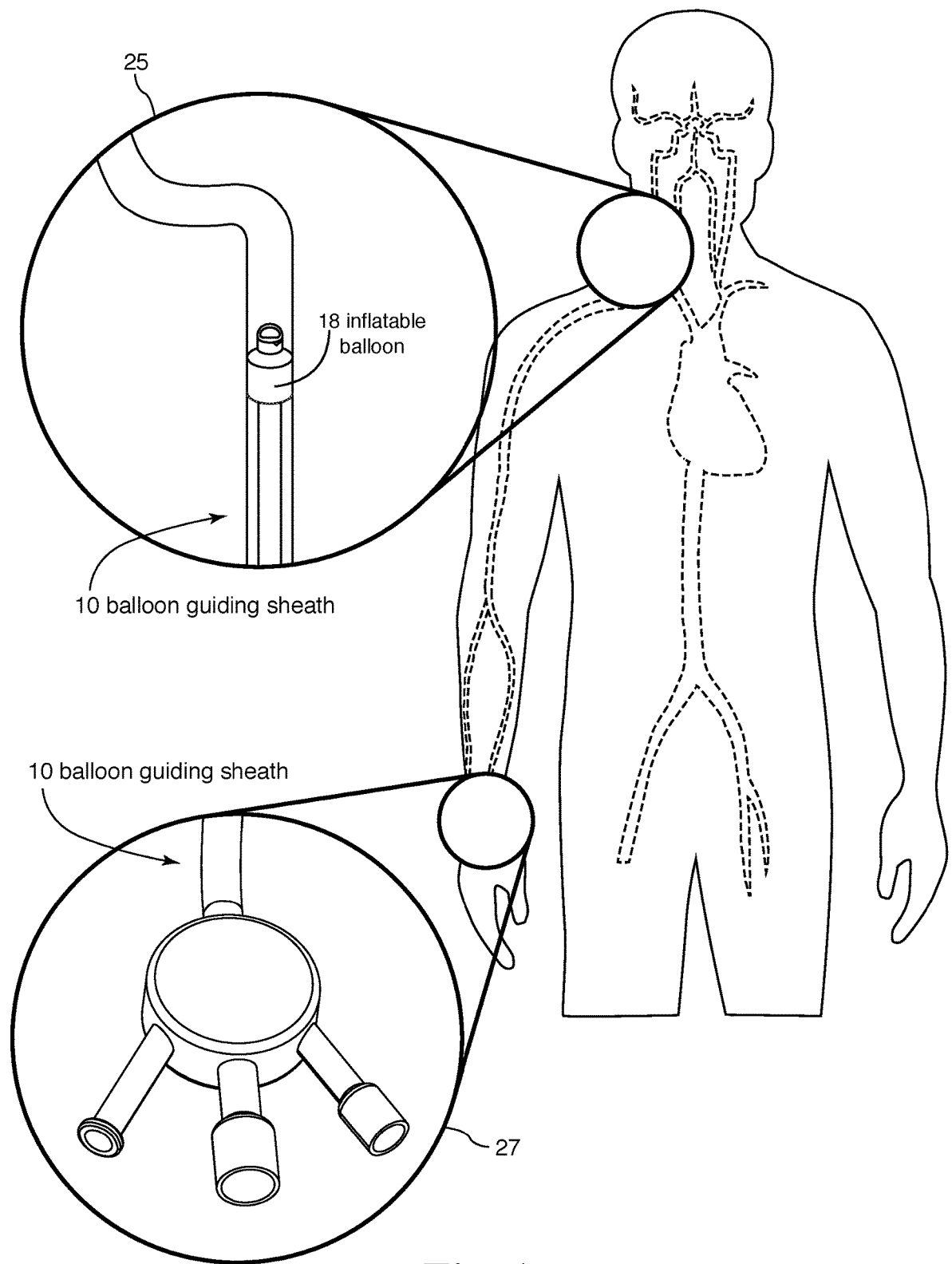
FIG. 1 illustrates a diagrammatic view of a person undergoing a thrombectomy procedure, according to some embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Additionally, reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

LIST OF REFERENCE NUMERALS

10—Balloon guiding sheath
12—Elongated sheath
13a, c—Inner tube
13b, d—Outer tube
14—Access port
16—Inflation port
18—Inflatable balloon
20—Distal port
21—Distal inflation port
22—Working lumen
30—First inflation lumen
31—Reinforcement layer
32—Second inflation lumen
34—Outer diameter
36—Inner diameter
38—Working length
39—Generally constant outer diameter
40—At least one vent hole
50—Internal carotid artery
52—Cervical portion
54—Petrous portion
56—Cavernous portion
58—Cerebral portion
59—Distal tip
60—Central axis
70—First portion
72—First inner diameter
74—Second portion
76—Second inner diameter
80—First inflation hole
82—Second inflation hole
84—Guide wire
90—Proximal portion
92—First outer diameter
94—Distal portion
96—Second outer diameter
98—Middle portion
110—Proximal inflation lumen
112—First inner diameter
114—Distal inflation lumen
116—Second inner diameter
118—Outer surface
120—Inner surface
122—Proximal side
124—Proximal edge FIG. 1 illustrates a diagrammatic view of a person undergoing a thrombectomy procedure to treat acute ischemic stroke. As indicated by enlarged circle area 27, an elongated sheath 12 can be inserted into an artery (e.g., a radial artery, known as transradial arterial access). A proximal portion of the elongated sheath 12 can remain outside of the patient's body while a distal portion of the elongated sheath 12 is advanced toward another artery (e.g., a target site in the patient's neck or skull to remove the thrombus) as indicated by enlarged circle area 25.

Figure 2A:
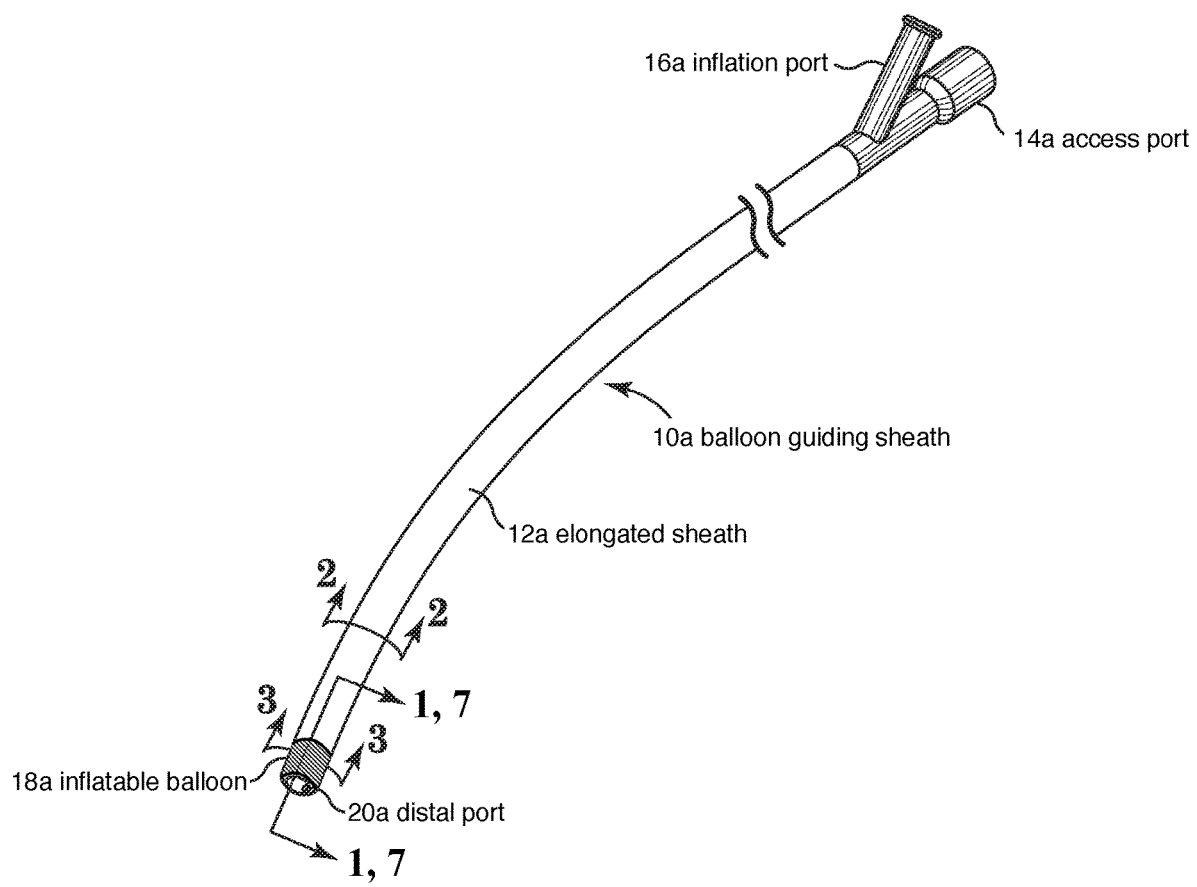
FIG. 2A illustrates a balloon guiding sheath, according to some embodiments.

A balloon guiding sheath 10a in accordance with embodiments of the invention can be described generally with reference to FIGS. 2A-7. As shown in FIG. 2A, a balloon guiding sheath 10a may comprise an elongated sheath 12a having a proximal end and a distal end. With reference to FIG. 3A, the elongated sheath 12a may include an inner tube 13a and an outer tube 13b that surrounds the inner tube 13a. It should be appreciated that many embodiments may also be implemented with one tube, as will be discussed later regarding FIG. 8. Other embodiments may include three or more tubes, also referred to as layers.

The components of the balloon guiding sheath 10 may be formed from a polymer (e.g. polytetrafluoroethylene, nylon, and the like). In some embodiments, the components may comprise Pellethane 63D or higher. Generally, the material selection may be focused on enhancing pushability in the balloon guiding sheath 10 as opposed to flexibility. However, it should be appreciated that in some embodiments the material selection may be focused on either or both pushability and/or flexibility.

Figure 3A:
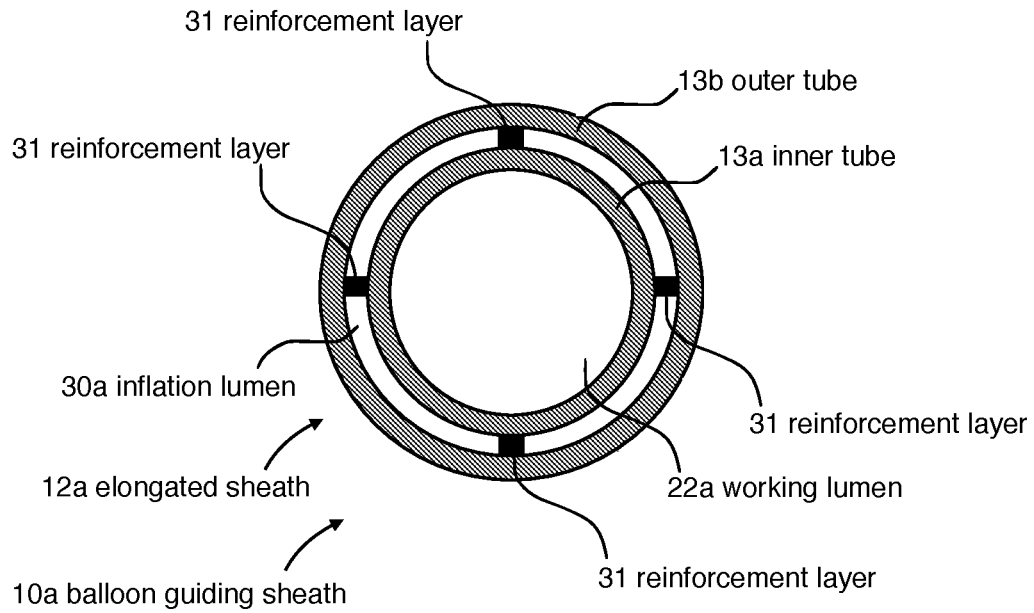
FIG. 3A illustrates a cross-sectional view of section 2-2 of the balloon guiding sheath, according to some embodiments.
Figure 3B:
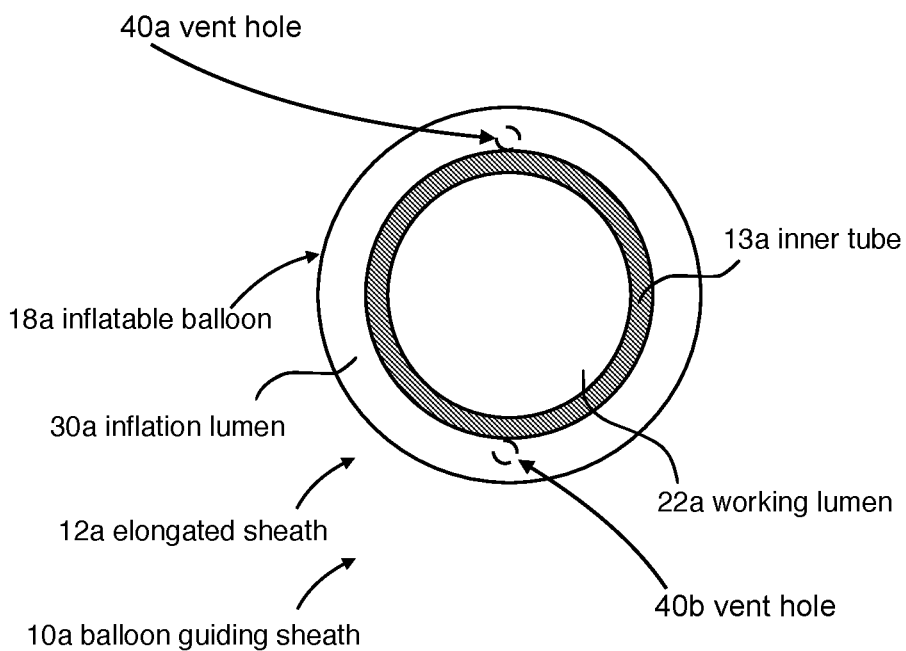
FIG. 3B illustrates a cross-sectional view of section 3-3 of the balloon guiding sheath, according to some embodiments.

As shown in FIG. 2A, the guiding sheath 10a may include an access port 14a located on the proximal end and an inflation port 16a also located on the proximal end. The guiding sheath 10a may include an inflatable balloon 18a coupled to the distal end and a distal port 20a also located on the distal end. As shown in FIGS. 3A and 3B, the guiding sheath 10a may include a working lumen 22a extending through the elongated sheath 12 between the access port 14a and the distal port 20a.

The guiding sheath 10a may also include an inflation lumen 30a that extends between the inflation port 16a and the balloon 18a. In the embodiment disclosed in FIGS. 1-7, the inflation lumen 30a is located between the inner tube 13a and the outer tube 13b. As illustrated, the inflation lumen 30a is not in fluid communication with the working lumen 22a. However, as will be discussed with regards to FIGS. 8-11B, embodiments may be arranged and configured whereby the working lumen 22 is in fluid communication with the inflation lumen 30.

Figure 2B:
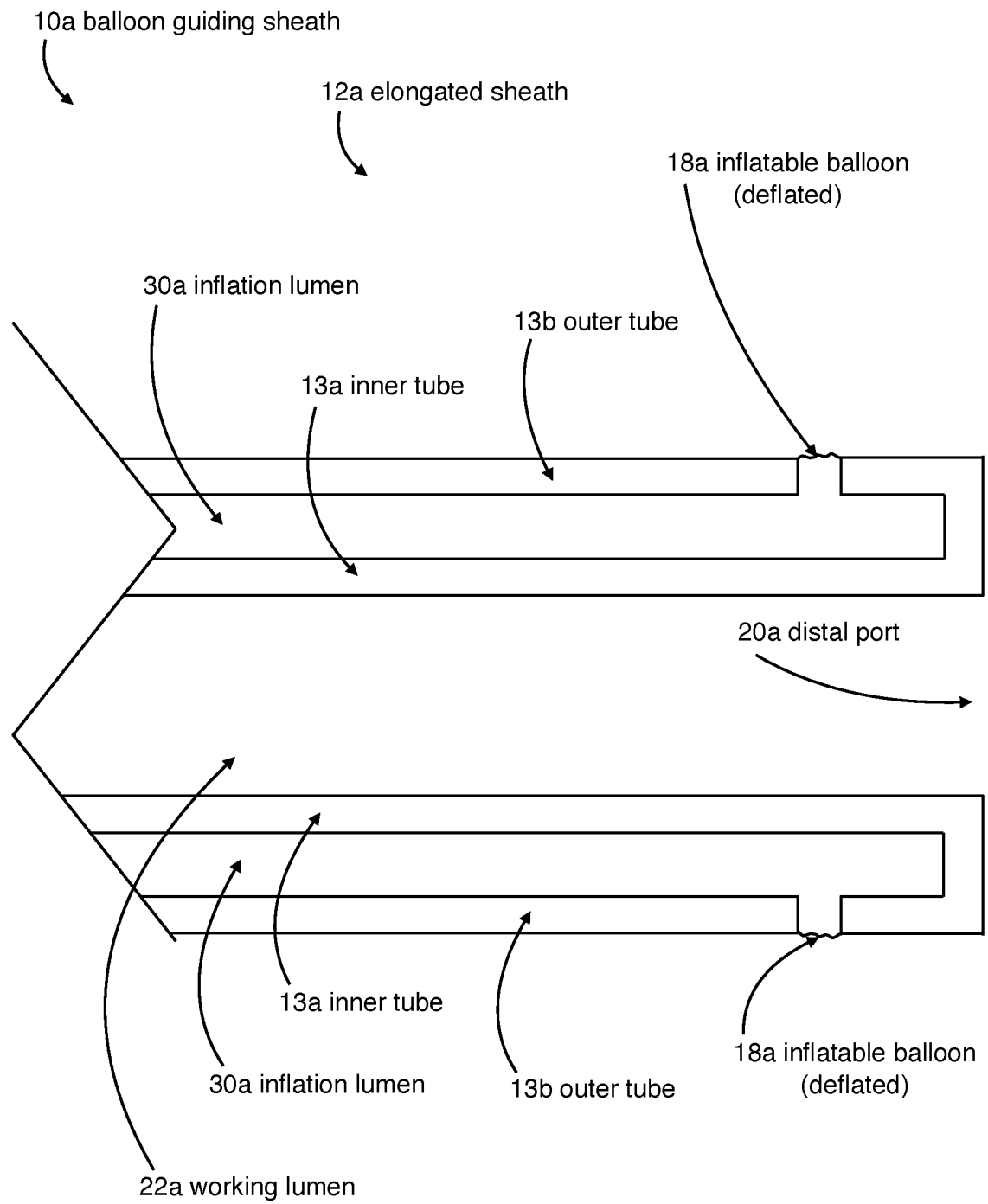
FIGS. 2B and 2C illustrate a cross-sectional view of section 1-1 of the balloon guiding sheath, with the balloon in a deflated state and an inflated state, respectively according to some embodiments.
Figure 2C:
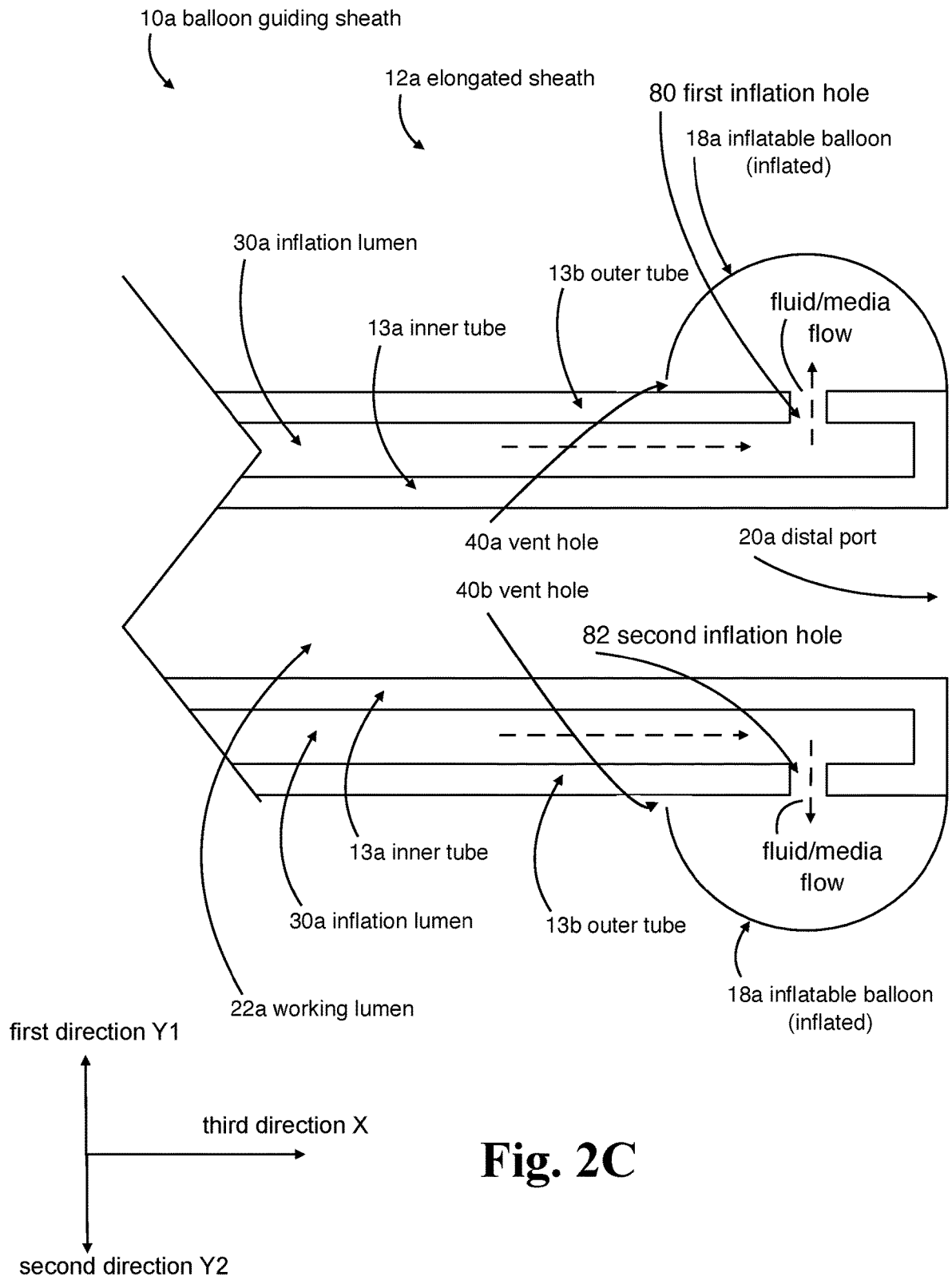

Now with reference to FIGS. 2B and 2C, a cross-sectional side view of section 1-1 is illustrated. As shown, the balloon 18a may move between a deflated state (FIG. 2B) and an inflated state (FIG. 2C) in response to fluid and/or media traveling through the inflation lumen 30a and into the balloon 18a. In such embodiments, the inflation lumen 30a is not in fluid communication with working lumen 22a. In this regard, the balloon 18a may be arranged and configured to inflate and deflate irrespective of any interaction with the working lumen 22a.

With reference to FIG. 3A, the guiding sheath 10a may include a reinforcement layer 31 located between the inner tube 13a and the outer tube 13b. The reinforcement layer 31 may be arranged and configured to enable flow of at least one of fluid and media through the inflation lumen 30a to thereby inflate the balloon 18a. The reinforcement layer 31 may be comprised of coiled and/or braided strands of material (e.g. stainless steel or polymer wire).

The elongated sheath 12a may be sized and configured to enable direct insertion into a patient's vasculature through an arteriotomy in the patient's carotid artery and/or vertebral artery. During use, the guiding sheath 10a may be positioned at a target site, whereby the balloon 18a is inflated to occlude blood flow through the patient's artery. The working lumen 22a, via the access port 14a, shall be arranged and configured to receive various instrumentation, such as a guide wire, tool(s), and the like. The instrumentation is then advanced through the working lumen 22a to the target site to treat and remove the embolus.

Figure 4:
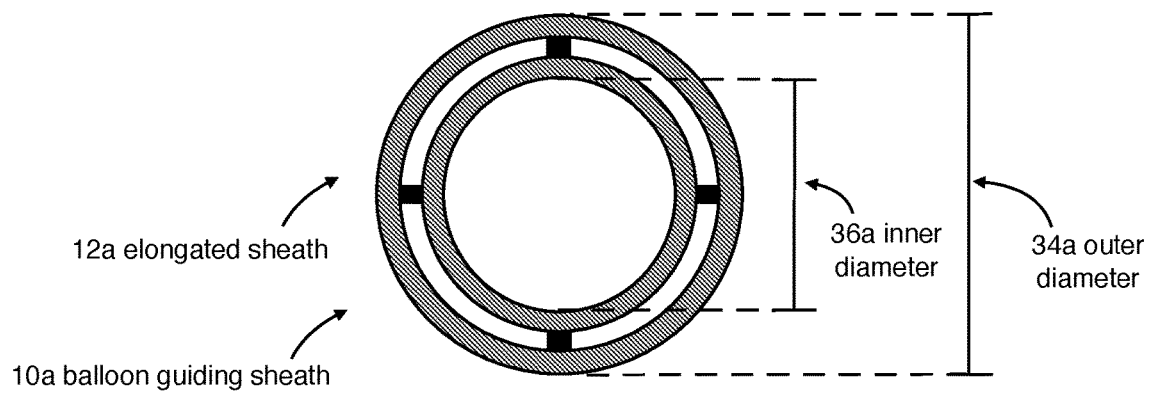
FIG. 4 illustrates a cross-sectional view of section 2-2 of the balloon guiding sheath, according to some embodiments.

Now with reference to FIG. 4, the elongated sheath 12a may define an outer diameter 34a that is less than or equal to 0.104 inches. In this regard, the elongated sheath 12a may fit through an 8 Fr opening. It should be appreciated that the opening may be a puncture, cavity, and/or aperture whether in the patient's vasculature or in any medical device used to treat the embolus. Moreover, the working lumen 22a may define an inner diameter 36a less than or equal to 0.090 inches. In some embodiments, the inner diameter 36a of the working lumen 22a is greater than or equal to 0.087 inches. However, it should be appreciated that the outer and inner diameters 34a, 36a may define any such dimension. For example, the outer diameter 34a may be greater than or equal to 0.104 inches. Additionally, in some embodiments, the inner diameter 36a may be less than or equal to 0.088 inches, or greater than or equal to 0.090 inches.

Figure 5:
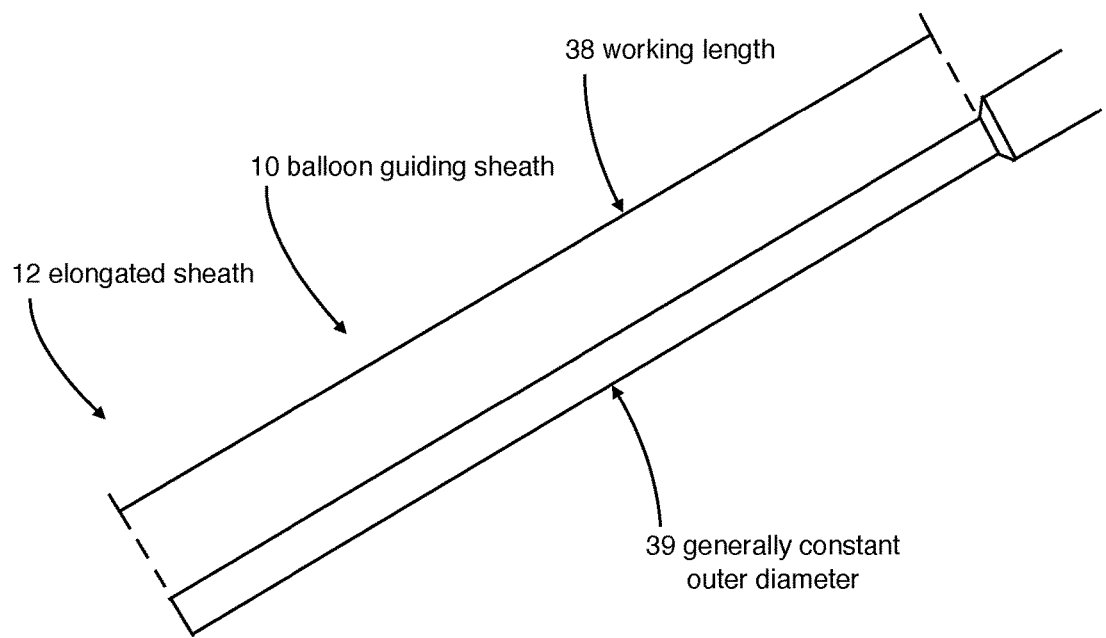
FIG. 5 illustrates a working length and generally constant outer diameter of the elongated sheath, according to some embodiments.
Figure 6:
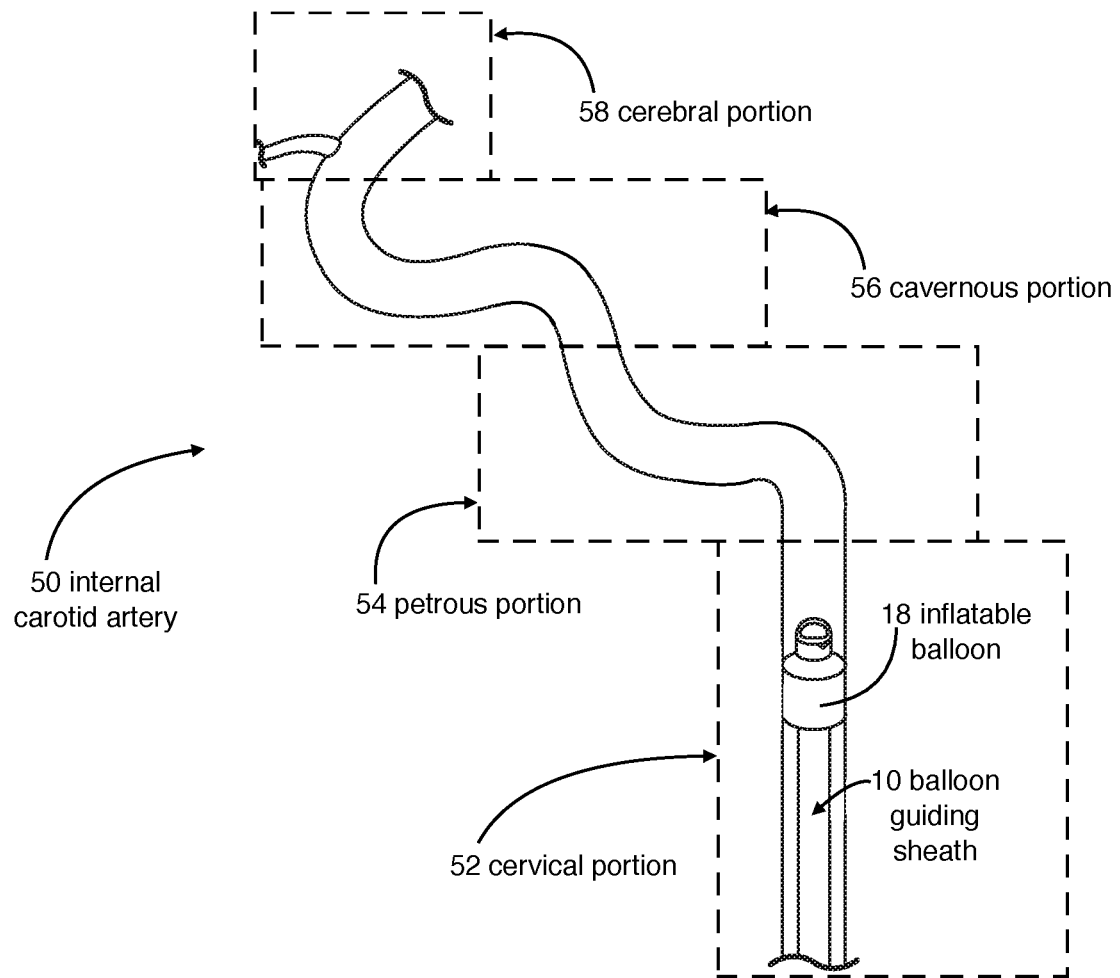
FIG. 6 illustrates an anatomy of an internal carotid artery, according to some embodiments.

As shown in FIG. 5, the elongated sheath 12a may have a generally constant outer diameter 39 along its working length 38a. However, some embodiments may have varying diameters along the working length 38. With additional reference to FIG. 6, the elongated sheath 12a may have a working length 38a that is long enough to enable the distal end to reach at least a cervical portion 52 of a patient's internal carotid artery 50 from the carotid artery. Even still, in some embodiments, the working length 38a may be long enough to enable the distal end to reach a petrous portion 54, cavernous portion 56, and/or a cerebral portion 58 of a patient's internal carotid artery 50 from the carotid artery. It should be appreciated that the location of the dashed boxes in FIG. 6 are not exact and merely intended to distinguish between the various portions of the patient's internal carotid artery.

Generally, the guiding sheath 10 disclosed herein is intended to maximize the inner diameter 36a, while maintaining a relatively thin outer diameter 34a. This may result in overall less inflation area within the inflation lumen 30 to inflate the balloon 18. Because inflation time is directly related to inflation area and length of the inflation lumen 30, the working length 38 shall be less than or equal to 30 centimeters. However, in some embodiments, the working length 38 is greater than or equal to 30 centimeters.

To effectively reach various portions of the patient's internal carotid artery, the elongated sheath 12 may be arranged and configured to have sufficient stiffness and tip flexibility to enable insertion of the working length 38 of the elongated sheath 12 into a patient's vasculature through an arteriotomy in the patient's carotid artery. As such, the distal port 20a may be positioned at a target site in the petrous portion 54, cavernous portion 56, and the cerebral portion 58 of the patient's internal carotid artery 50.

Figure 7A:
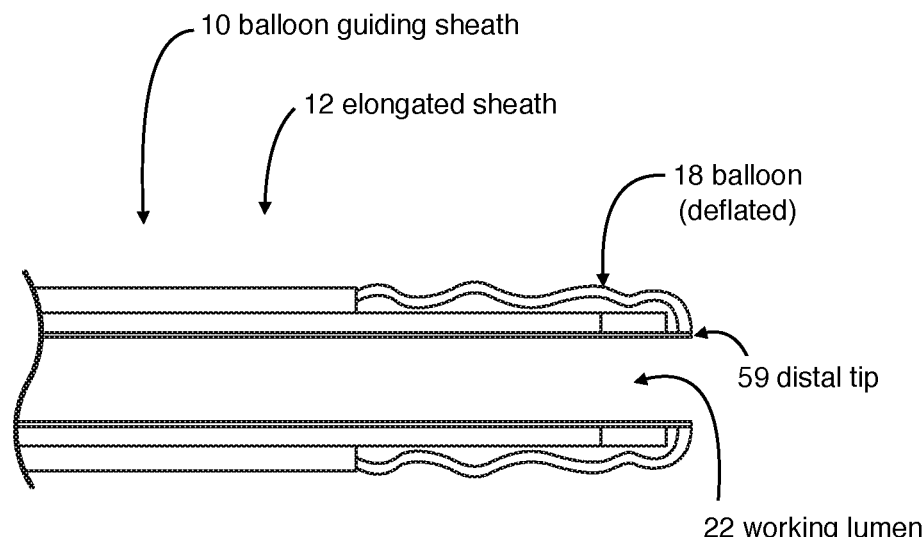
FIGS. 7A and 7B illustrate cross-sectional views of section 7-7 of the balloon guiding sheath with the balloon in a deflated state and an inflated state, respectively, according to some embodiments.
Figure 7B:
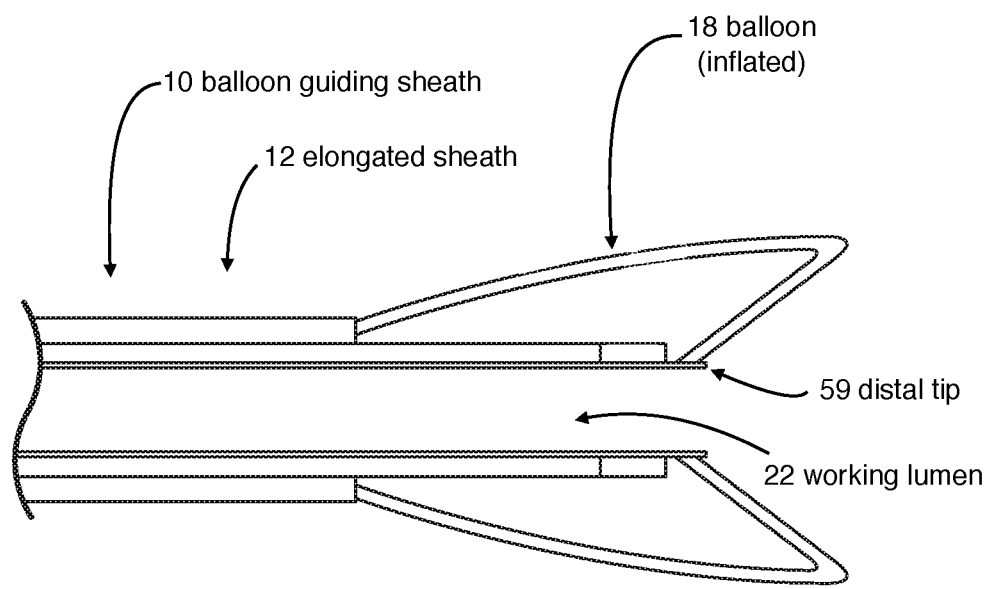

In order to safely remove the embolus from the target site, the balloon 18 may define various shapes and sizes. For example, as shown in FIGS. 7A and 7B, the balloon may be arranged and configured to extend around and beyond a distal tip 59 of the elongated sheath 12. With specific reference to FIG. 7B, the balloon 18 may define a funnel-shaped opening into the distal port 20 when the balloon 18 is in an inflated state. The funnel-shape may thereby ensure that the embolus and any harmful tissue is effectively directed and guided into the working lumen 22 for complete removal from the patient's artery. Furthermore, the funnel-shape may safeguard the balloon 18 so that the balloon 18 does not occlude the working lumen 22 and any instrumentation or tissue that needs to travel through the working lumen 22.

Generally, the guiding sheath 10 disclosed herein may be implemented with any size, shape, and location of balloon 18. For example, in some embodiments, the balloon 18 does not extend beyond the distal tip 59 of the working lumen 22.

Figure 8:
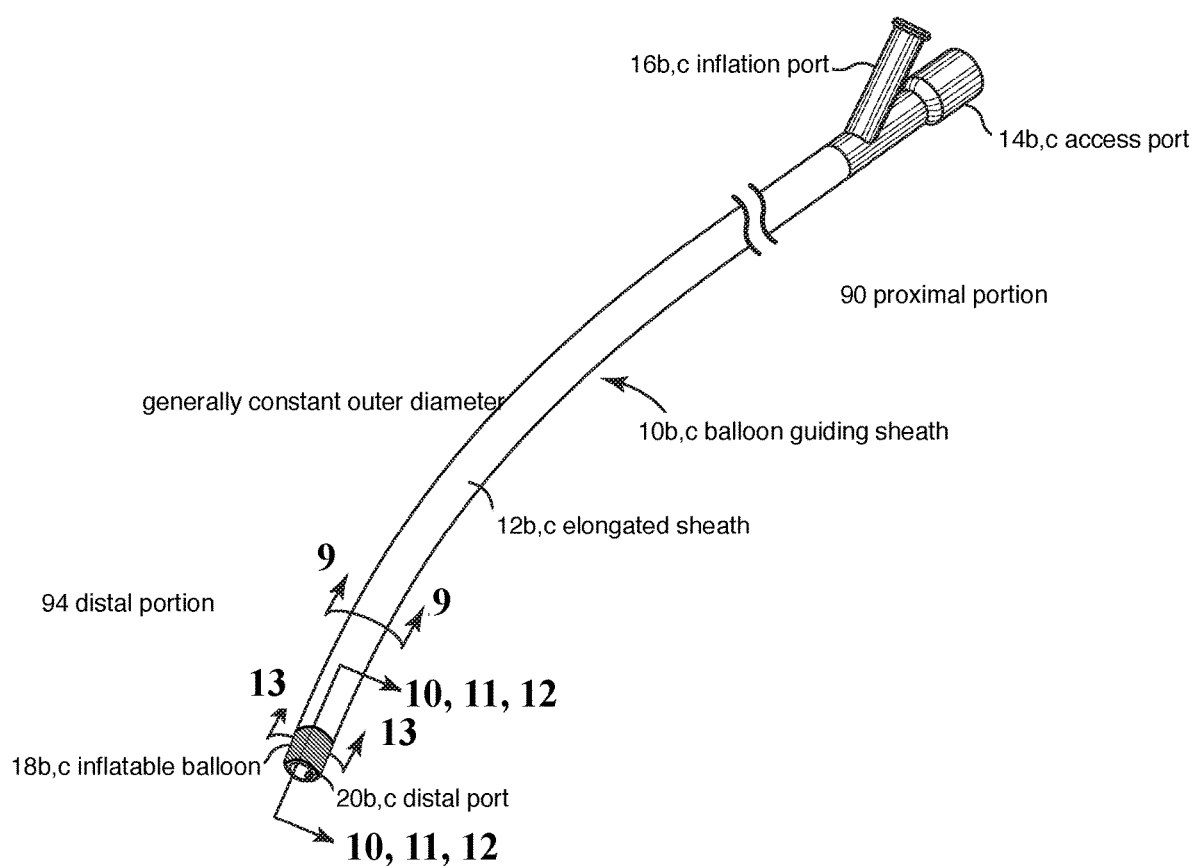
FIG. 8 illustrates another balloon guiding sheath, according to some embodiments.

Another balloon guiding sheath 10b in accordance with embodiments of the invention is now described with reference to FIGS. 8-13 C. As shown in FIG. 8, the guiding sheath 10b includes an elongated sheath 12b having a proximal end and a distal end. The guiding sheath 10b may include an access port 14b located on the proximal end and an inflation port 16b on the proximal end. The guiding sheath 10b may include an inflatable balloon 18b coupled to the distal end and a distal port 20b located on the distal end. The elongated sheath 12b may be sized and configured to enable direct insertion into a patient's vasculature through an arteriotomy in at least one of the patient's carotid artery and vertebral artery to position the balloon 18b at the target site of the embolus.

Similar to embodiment 10a, the guiding sheath 10b may also include a working lumen 22b extending through the elongated sheath 12b between the access port 14b and the distal port 20*b*. The guiding sheath 10*b* may include an inflation lumen 30*b* extending through the elongated sheath 12*b* between the inflation port 16*b* and the balloon 18*b*. Unlike embodiment 10*a*, guiding sheath 10*b* may be arranged and configured such that the working lumen 22*b* transitions between being in fluid communication with the inflation lumen 30*b* and then not being in fluid communication with the inflation lumen 30*b*. In this regard, prior to advancing the guide wire 84 through the working lumen 22*b*, the working lumen 22*b* and the inflation lumen 30*b* are in fluid communication with each other. However, once the guide wire 84 is advanced through the working lumen 22*b* and beyond the distal tip 59 of the elongated sheath 12*b*, the guide wire 84 thereby occludes the distal tip 59 which cuts off the fluid communication between the working lumen 22*b* and the inflation lumen 30*b* thereby allowing fluid and/or media to flow through the inflation lumen 30*b* and into the balloon 18*b* to inflate the balloon 18*b*.

Stated differently, the working lumen 22*b* may not be in fluid communication with the inflation lumen 30*b* when the balloon 18*b* is inflated. Additionally, the working lumen 22*b* may be in fluid communication with the inflation lumen 30*b* when the balloon 18*b* is at least partially deflated. However, either scenario may apply if the balloon 18*b* is in the midst of inflating or deflating. In other words, it can be said that the working lumen 22*b* is not in fluid communication with the inflation lumen 30*b* when the balloon 18*b* is inflated or at least partially inflated. Likewise, the working lumen 22*b* is in fluid communication with the inflation lumen 30*b* when the balloon 18*b* is deflated or at least partially deflated. Such tip-occluding embodiments may be beneficial because they maximize the inner diameter of the working lumen 22*b* while minimizing the outer diameter of the elongated sheath 12*b*.

Figure 9:
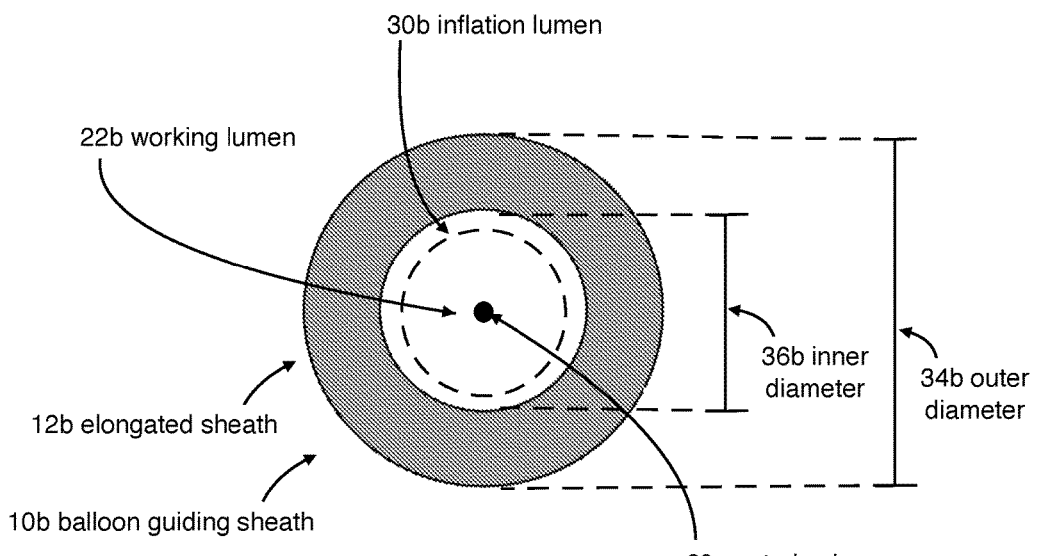
FIG. 9 illustrates a cross-sectional view of section 9-9 of the balloon guiding sheath, according to some embodiments.

To further describe the relationship between the working lumen 22*b* and the inflation lumen 30*b* we now refer to FIG. 9. The elongated sheath 12*b* may define a central axis 60 extending from the proximal end to the distal end. As shown in FIG. 9, at least a portion of the working lumen 22*b* may overlap the central axis 60 of the elongated sheath 12*b*, while the inflation lumen 30*b* does not overlap the central axis 60 of the elongated sheath 12*b*.

With continued reference to FIG. 9, the elongated sheath 12*b* may define an outer diameter 34*b* less than or equal to 0.104 inches such that the elongated sheath 12*b* fits through an 8 Fr opening. Additionally, the working lumen 22*b* may define an inner diameter 36*b* less than or equal to 0.090 inches. In some embodiments, the inner diameter 36*b* of the working lumen 22*b* is greater than or equal to 0.087 inches. Similar to above, it should be appreciated that the outer and inner diameters 34*b*, 36*b* may define any such dimension. For example, the outer diameter 34*b* may be greater than or equal to 0.104 inches. Additionally, in some embodiments, the inner diameter 36*b* may be less than or equal to 0.087 inches, or greater than or equal to 0.090 inches.

Similar to the embodiment described above, the elongated sheath 12*b* also has a generally constant outer diameter 39 along its working length 38*b*. Additionally, the elongated sheath 12*b* may also define a working length 38*b* long enough to enable the distal end to reach at least a cervical portion 52, petrous portion 54, cavernous portion 56, and a cerebral portion 58 of the patient's internal carotid artery 50 from the carotid artery.

Furthermore, the balloon 18*b* may extend around and beyond a distal tip 59 of the elongated sheath 12*b* and define a funnel-shaped opening into the distal port 20*b* when the balloon 18*b* is in an inflated state. Moreover, the elongated sheath 12*b* may also be arranged and configured to have sufficient stiffness and tip flexibility to enable insertion of the working length 38*b* of the elongated sheath 12*b* into a patient's vasculature through an arteriotomy in the patient's carotid artery to position the distal port 20*b* at a target site in at least one of the petrous portion 54, cavernous portion 56, and the cerebral portion 58 of the patient's internal carotid artery 50.

Figure 10:
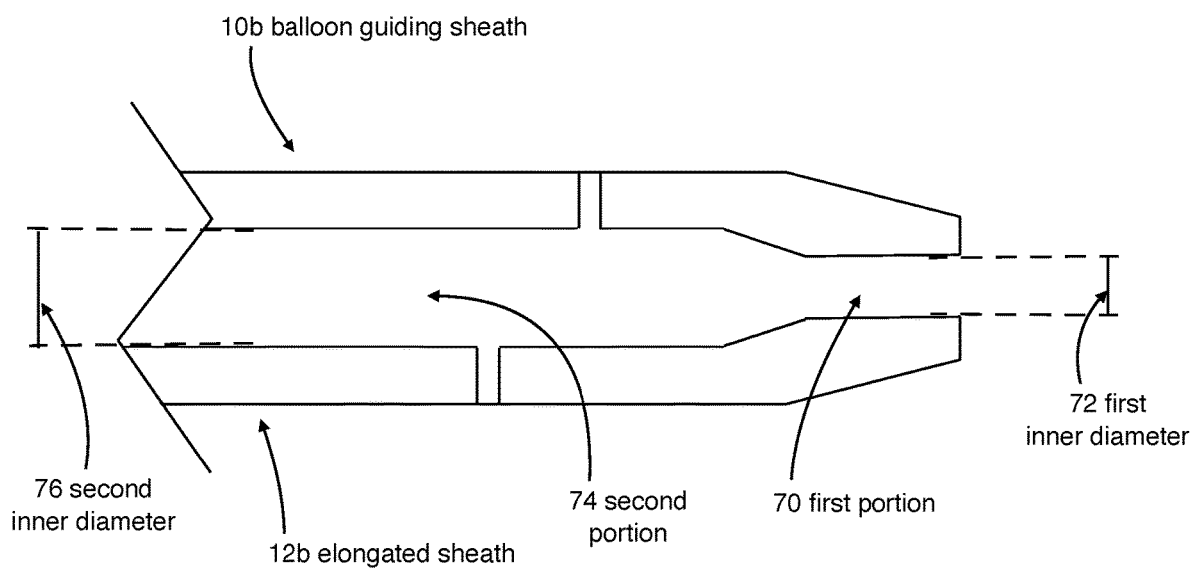
FIG. 10 illustrates a cross-sectional view of section 10-10 of the balloon guiding sheath, according to some embodiments.

Now with reference to FIG. 10, the working lumen 22*b* may define various portions having different size diameters. As shown, the working lumen 22*b* may comprise a first portion 70 defining a first inner diameter 72 and a second portion 74 defining a second inner diameter 76. As shown, the second portion 74 is located proximal to the first portion 70. The second inner diameter 76 may be greater than the first inner diameter 72.

Figure 11A:
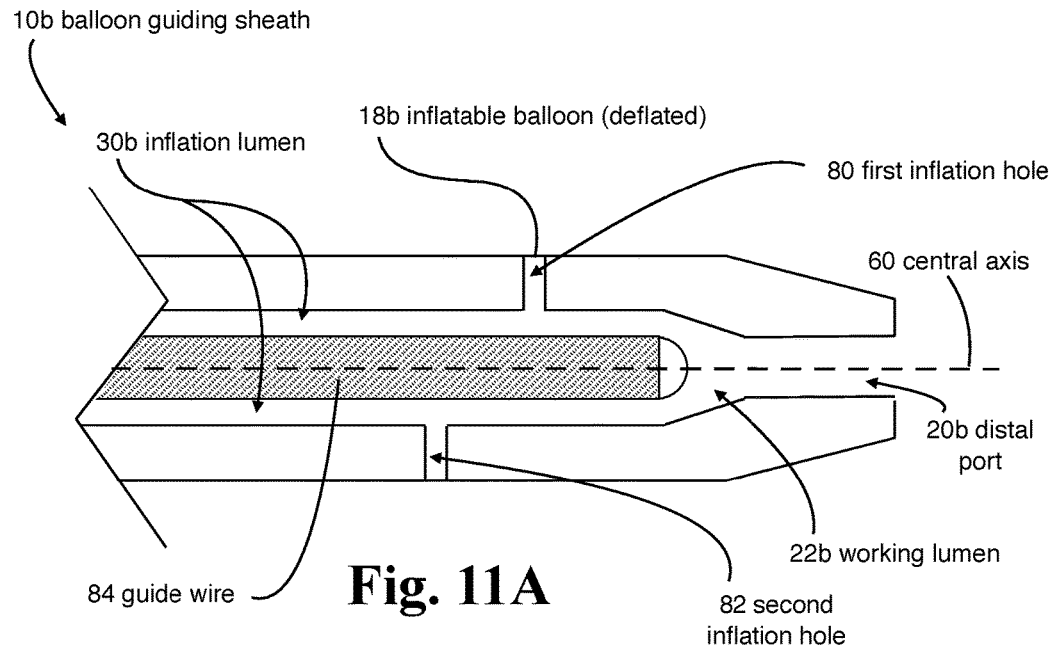
FIGS. 11A and 11B illustrate cross-sectional views of section 11-11 of the balloon guiding sheath with the balloon in a deflated state and an inflated state, respectively, according to some embodiments.
Figure 11B:
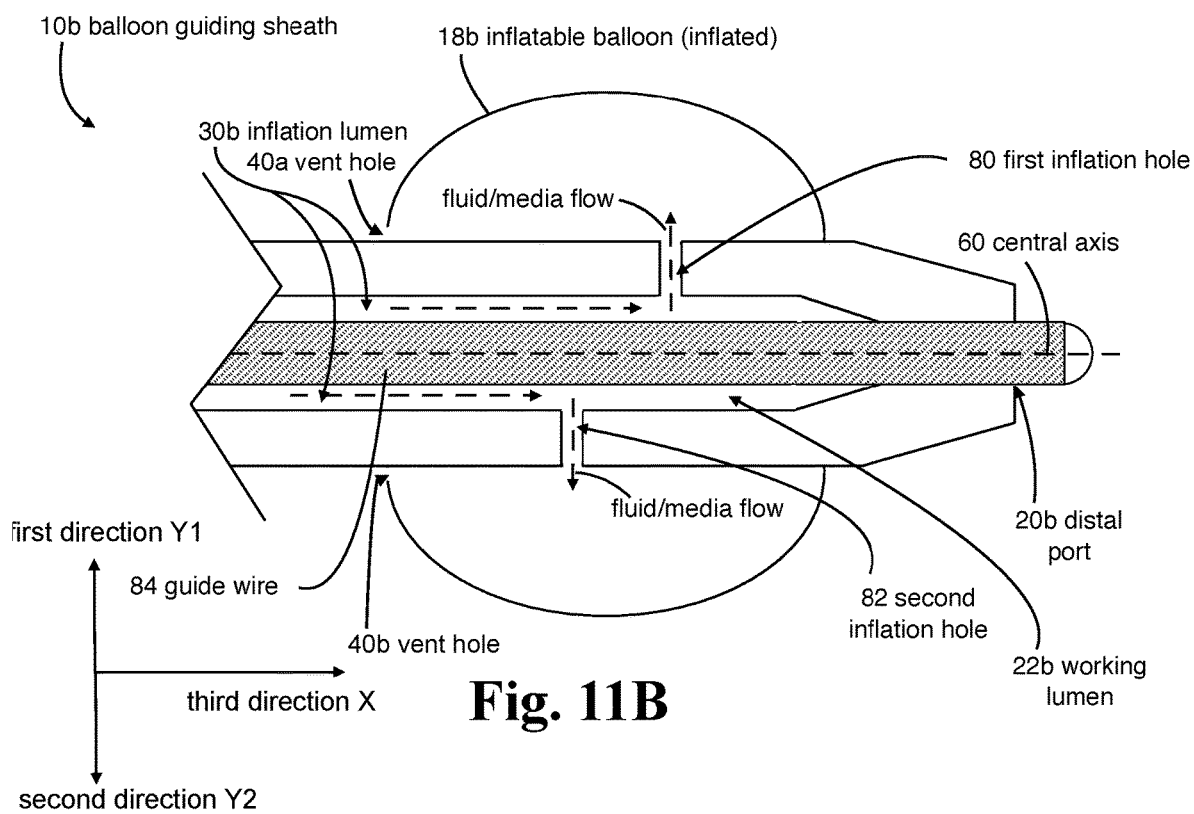

As shown in FIGS. 11A and 11B, the balloon guiding sheath 10*b* may include a first inflation hole 80 extending from the working lumen 22*b* through a sidewall of the elongated sheath 12*b*. In this regard, when a guide wire 84 is inserted into the working lumen 22*b* and out through the distal port 20*b*, the distal port 20*b* thereby creates a seal against the guide wire 84. Once the guide wire 84 creates a seal with the distal port 20*b*, this enables flow of fluid and/or media through the inflation lumen 30*b* into the first inflation hole 80 and into the balloon 18*b* to thereby inflate the balloon 18*b*. While many of the figures show the balloon 18 disposed flush with the distal port 20, it should be appreciated that the balloon 18 may be offset by any distance, as shown in FIGS. 11A and 11B. In some embodiments, the balloon 18 is offset about 4 millimeters from the distal port 20.

Furthermore, the guiding sheath 10*b* may include a second inflation hole 82 extending from the working lumen 22*b* through the sidewall of the elongated sheath 12*b*. Again, once the guide wire 84 creates a seal with the distal port 20*b*, this enables flow of fluid and/or media through the inflation lumen 30*b* into the second inflation hole 82 and into the balloon 18*b* to thereby inflate the balloon 18*b*. As shown in FIGS. 11A and 11B, the first and second inflation holes 80, 82 may be horizontally offset from each other. However, in some embodiments, the first and second inflation holes 80, 82 are substantially horizontally aligned with each other. The inflation holes may be staggered to thereby inflate various portions of the balloon at different times.

Furthermore, while not shown, the working lumen 22 may define more than two portions having more two ore more different diameters. In this manner, the guide wire 84 may occlude various portions of the working lumen 22 thereby allowing one or more balloons 18 to inflate at specific intervals. Such configurations may be beneficial in treating and removing different types and sizes of emboli.

Figure 12A:
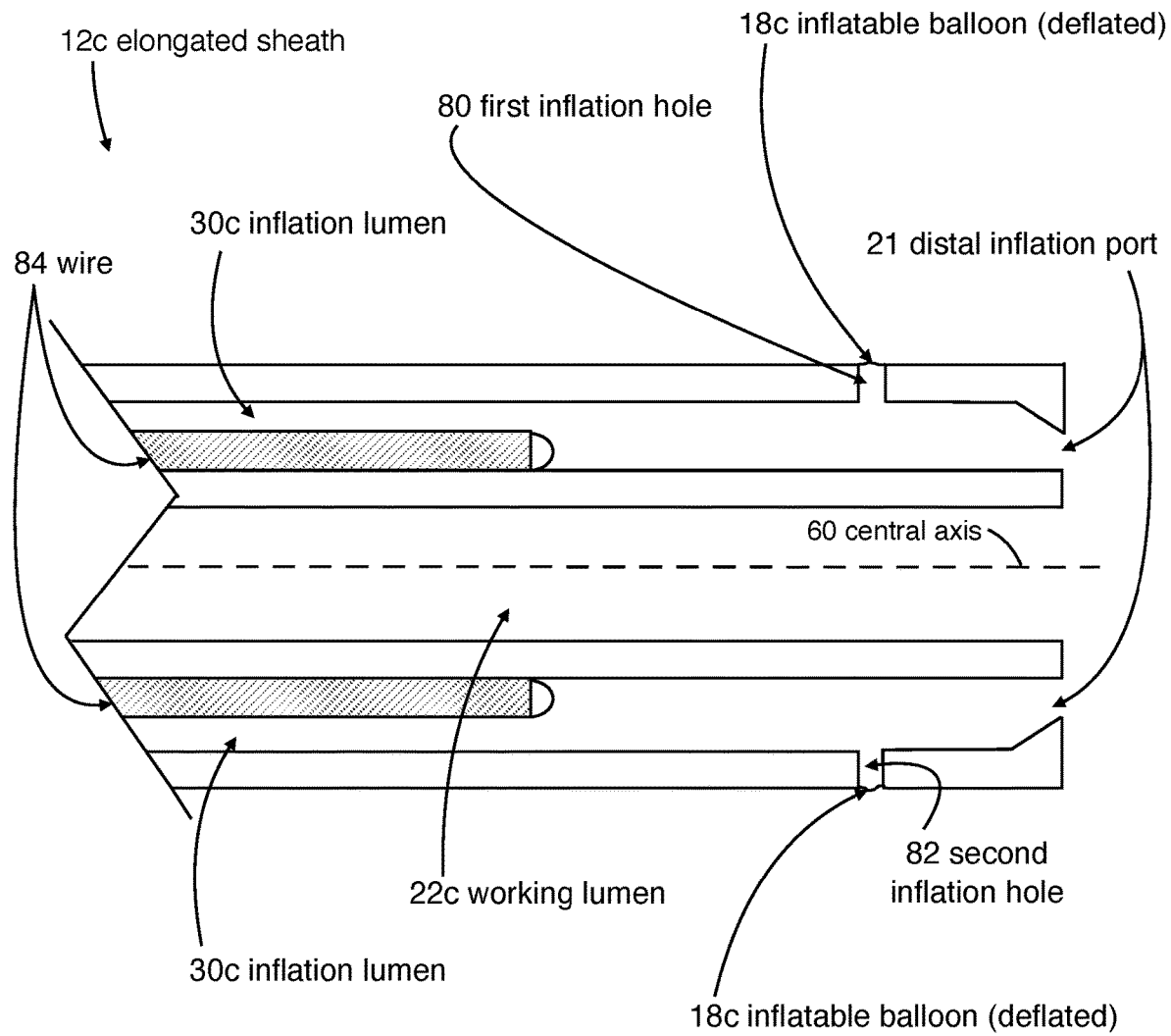
FIGS. 12A and 12B illustrate cross-sectional views of section 12-12 of the balloon guiding sheath with the balloon in a deflated state and an inflated state, respectively, according to some embodiments.
Figure 12B:
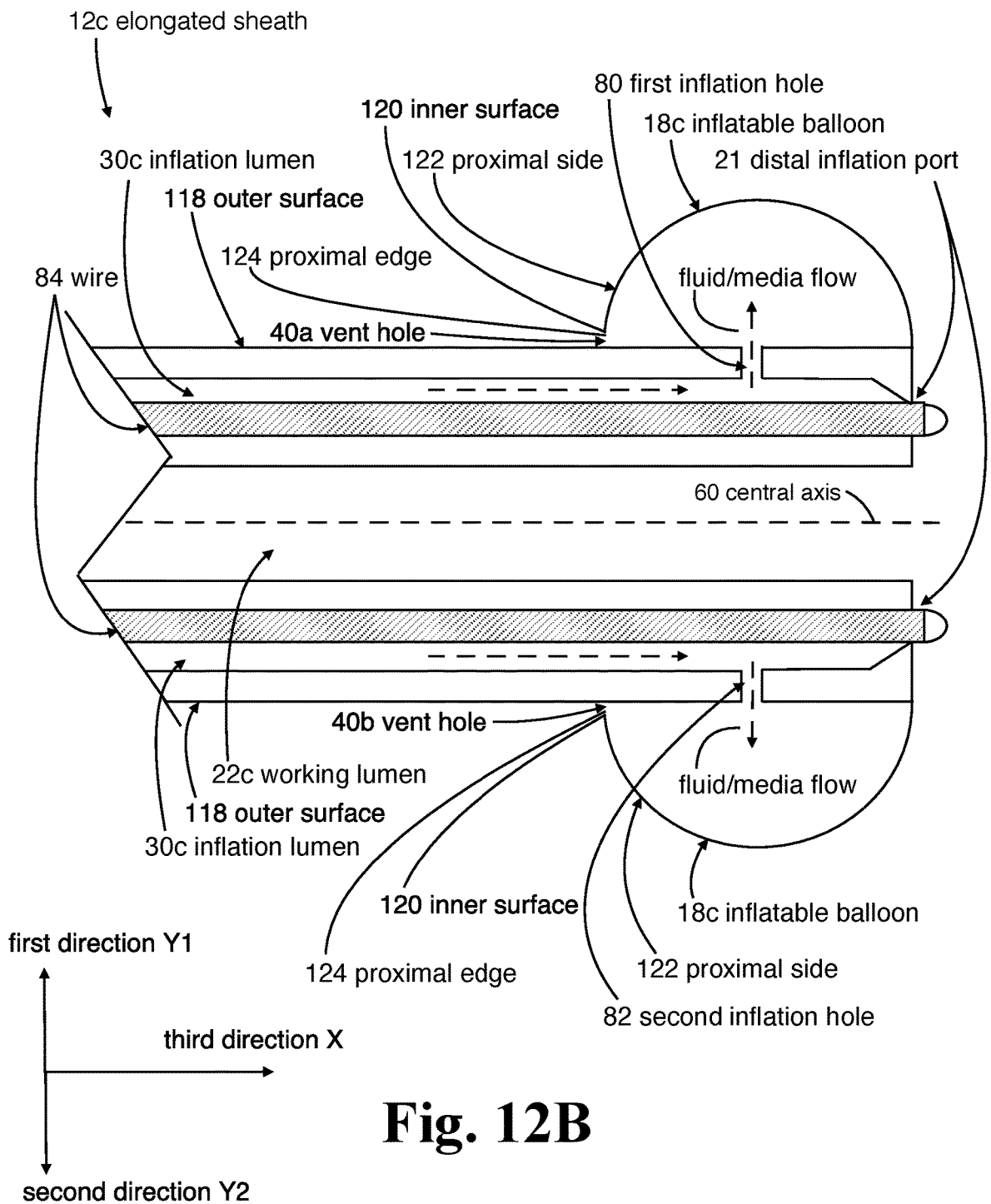

Now with reference to FIGS. 12A and 12B, the guiding sheath 10*c* may include one or more inflation lumen(s) 30*c* extending through the elongated sheath 12*c* between the inflation port 16*c* and the balloon 18*c*. As shown, the inflation lumen 30*c* may comprise a distal inflation port 21 extending through an endwall of the elongated sheath 12*c*. In this regard, the inflation lumen 30*c* is not in fluid communication with the working lumen between the access port 14*c* and the distal port 20*c*.

The balloon guiding sheath 10*c* may also include one or more inflation hole(s) 80, 82 extending from the inflation lumen 30*c* through a sidewall of the elongated sheath 12*c*. As such, when a guide wire 84 is inserted into the inflation lumen 30*c* and out through the distal inflation port 21, the distal inflation port 21 may thereby create a seal against the guide wire 84. Once the seal is created, the inflation lumen 30*c* may enable flow of at least one of fluid and media through the inflation lumen 30*c* into the one or more inflation hole(s) 80, 82 and into the balloon 18*c* to thereby inflate the balloon 18*c*, as shown in FIG. 12B. As further shown in FIGS. 12A and 12B, the elongated sheath 12*c* may have a generally constant outer diameter 39 along its working length.

FIGS. 13A, 13B, and 13C illustrate a variety of cross-sectional views of section 13-13 of the elongated sheath 12*c*. As shown, the guiding sheath 10 may include one or more inflation lumen(s) 30*c* arranged in a variety of configurations. For example, as shown in FIG. 13A, the elongated sheath 12*c* may include six inflation lumens 30*c* arranged in any pattern around the working lumen 22*c*. As illustrated in FIG. 13B, the elongated sheath 12*c* may include two inflation lumens 30*c* arranged on opposite sides of the working lumen 22*c*. Even still, as shown in FIG. 13C, the elongated sheath 12*c* may include one inflation lumen 30*c* adjacent an oval-shaped working lumen 22*c* that is off-center with respect to the central axis. It should be appreciated that the working lumen 22*c* may define any such cross-sectional shape, such as circular, round, oblong, and even shapes such as triangular, rectangular, and any shape defining five or more sides.

Figure 14A:
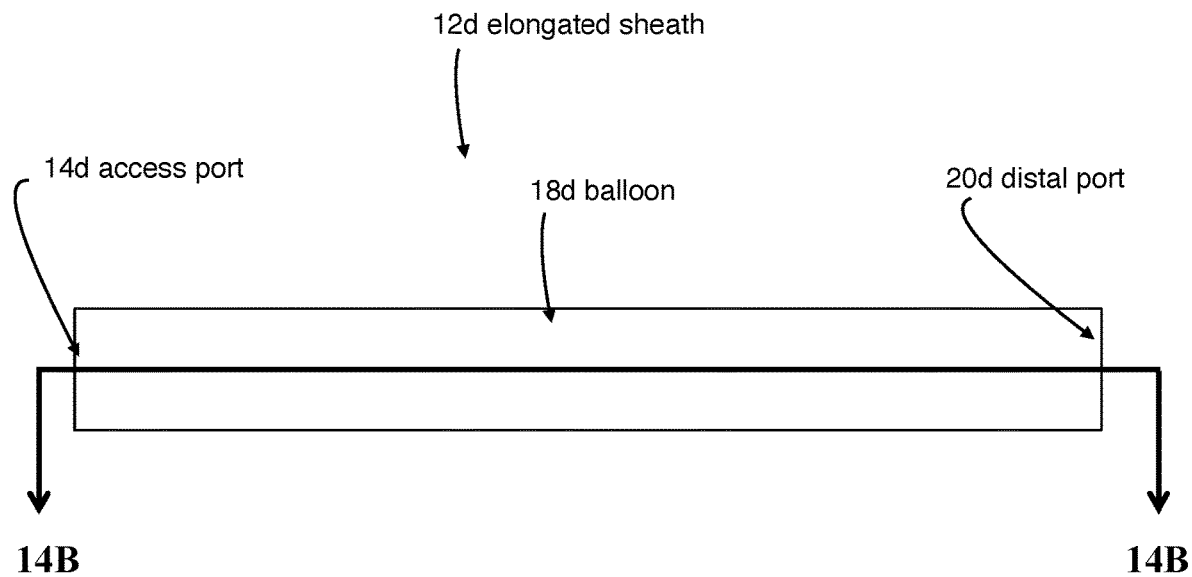
FIG. 14A illustrates another balloon guiding sheath, according to some embodiments.
Figure 14B:
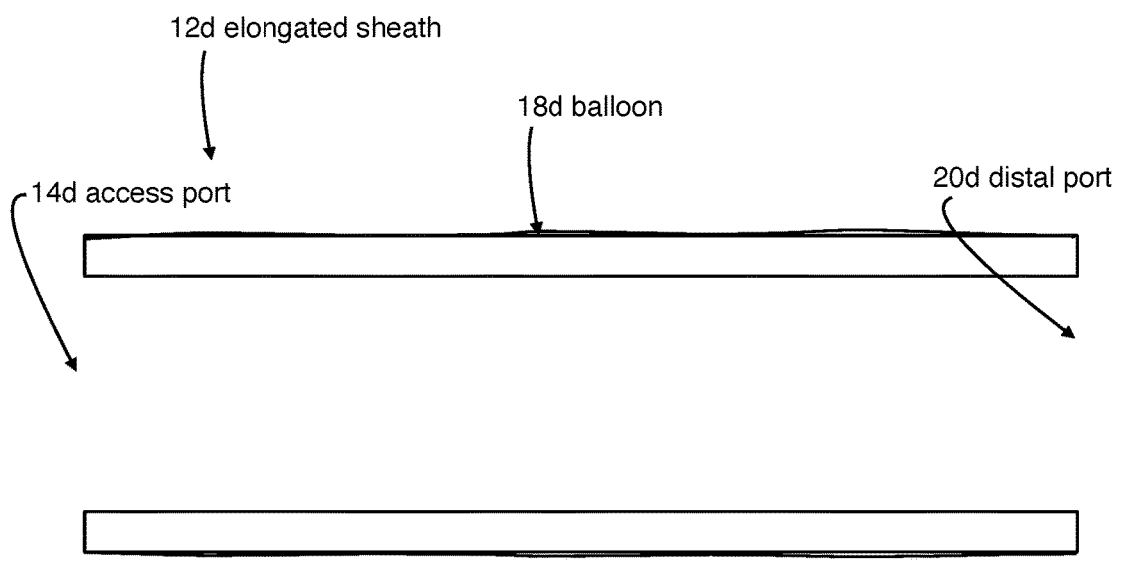
FIG. 14B illustrate cross-sectional views of section 14B-14B of the balloon guiding sheath, according to some embodiments.

As shown in FIGS. 14A and 14B, the elongated sheath 12*d* may define another embodiment whereby the balloon 18*d* extends along the entire outer surface area, or at least more than half of the outer surface area, of the elongated sheath 12*d*. In such embodiments, the balloon 18*d* may extend all the way from the access port 14*d* to the distal port 20*d*. The balloon 18*d* material may be arranged and configured such that certain sections of the balloon may inflate/deflate at predetermined zones. Some embodiments, with respect to FIGS. 14A and 14B, may be devoid of inflation holes 80, 82.

Additionally, in some embodiments, the entire elongated sheath 12 is foldable, or self-expanding. This may allow the elongated sheath 12, while in it's folded state, to be moved to the target site and then expanded to thereby provide antegrade blood flow cessation.

All of the illustrated embodiments have shown the inflation holes 80, 82 to be disposed closer to the distal port 20 then the access port 14; however, many embodiments may be configured whereby the inflation holes 80, 82 are disposed closer to the access port 14 then the distal port 20. Such embodiments may result in shorter time to inflate and deflate the balloon 18.

Additionally, because of the need to minimize air in the balloon 18 during use, the guiding sheath 10 may be arranged and configured to include a vent hole(s) at the proximal end of the balloon 18. The vent hole(s) may be formed by bonding a wire between the balloon 18 and the elongated sheath 12, and then removing the wire prior to use. Thereby when the balloon 18 is inflated, the vent hole may allow air to escape through the vent hole, but not let fluid and/or media leak out. In this regard, the vent hole is large enough to allow air through, but small enough to prevent liquid and media from passing through.

With reference to FIGS. 15-18, the disclosure also includes methods for using the balloon guiding sheaths 10*a*, 10*b* as described above. Some methods may be implemented with either guiding sheath 10*a* or 10*b*. However, some methods may only be implemented with embodiment 10*b*. Each circumstance will be described in detail below.

Figure 15:
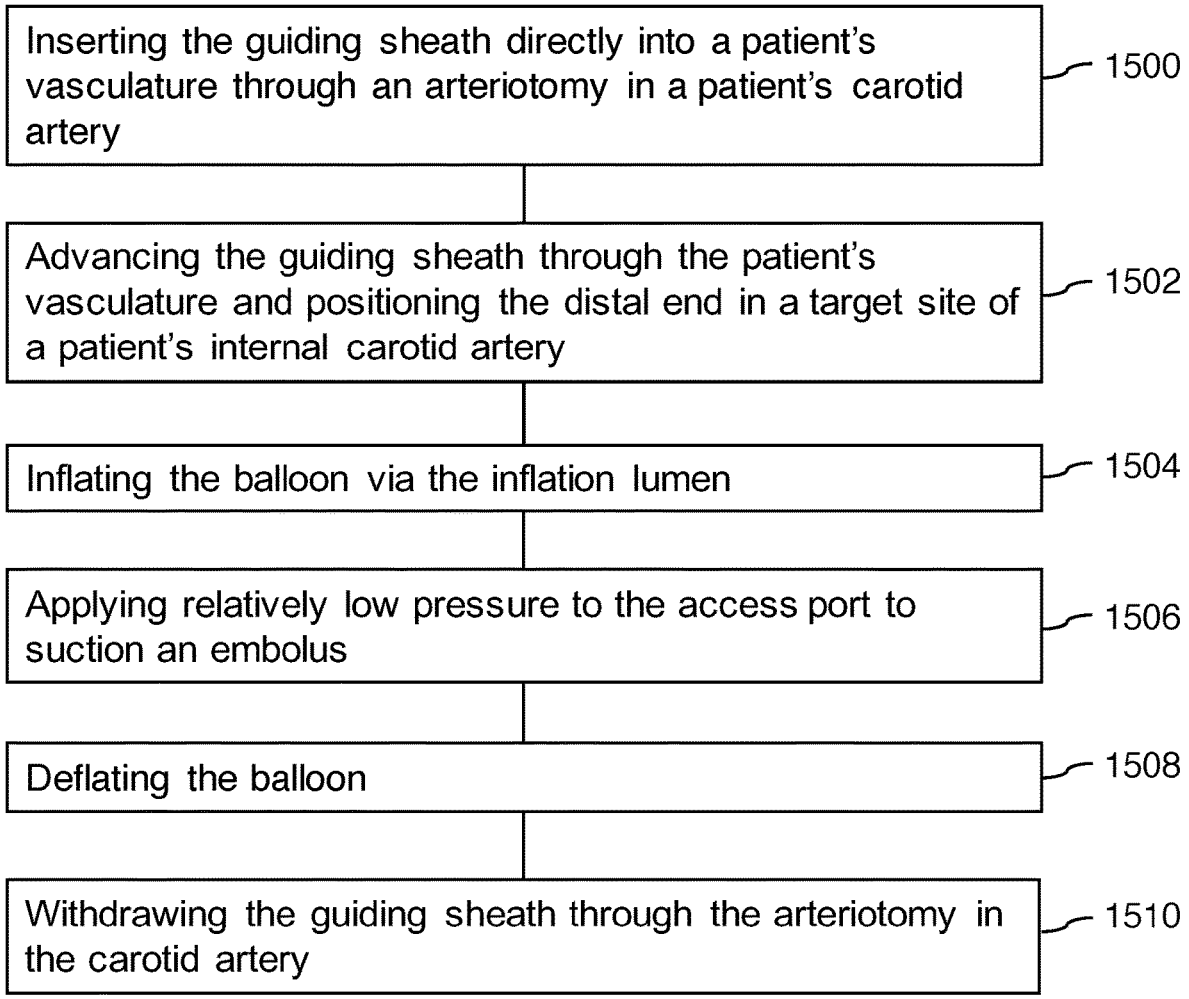
FIGS. 15, 16, 17, and 18 illustrate methods of using a balloon guiding sheath, according to some embodiments.

As shown in FIG. 15, methods may include inserting the guiding sheath 10*a*, 10*b* directly into a patient's vasculature through an arteriotomy in a patient's carotid artery (at step 1500). Methods may also include advancing the guiding sheath 10*a*, 10*b* through the patient's vasculature and positioning the distal end in a target site of a patient's internal carotid artery 50 (at step 1502). Once the guide sheath 10*a*, 10*b* has been advanced, methods may include inflating the balloon 18*a*, 18*b* via the inflation lumen 30*a*, 30*b* (at step 1504). As previously disclosed, the target site may be at least a cervical portion 52, petrous portion 54, cavernous portion 56, and a cerebral portion 58 of the internal carotid artery 50.

Furthermore, methods may include applying relatively low pressure to the access port 14*a*, 14*b* to suction an embolus (at step 1506). Methods may thereby include deflating the balloon 18*a*, 18*b* (at step 1508) and thereby withdrawing the guiding sheath 10*a*, 10*b* through the arteriotomy in the carotid artery (at step 1510).

Figure 16:
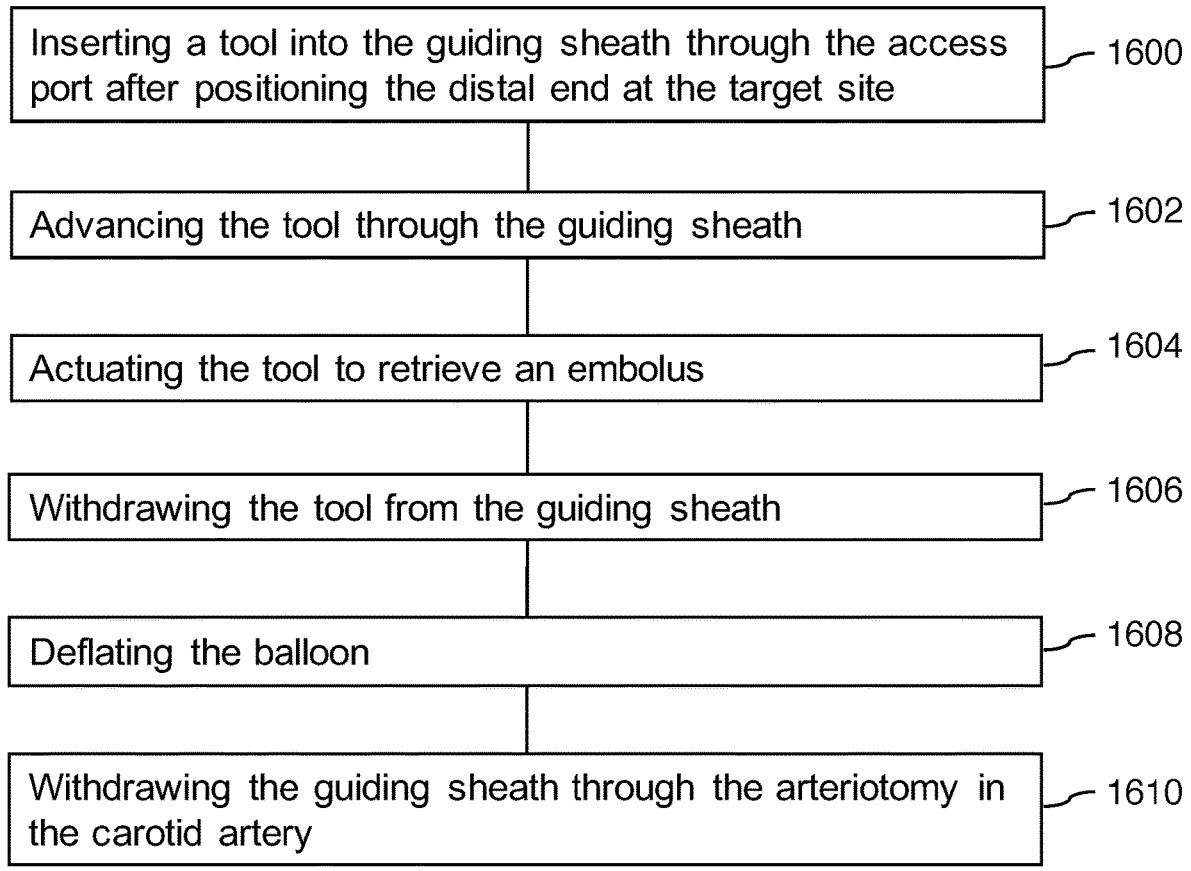

Now with reference to FIG. 16, after positioning the distal end at the target site, the user may insert a tool into the guiding sheath 10*a*, 10*b* through the access port 14*a*, 14*b* (at step 1600). The user may advance the tool through the guiding sheath 10*a*, 10*b* (at step 1602) and actuate the tool to retrieve the embolus (at step 1604). Once the embolus has been retrieved, the tool may be withdrawn from the guiding sheath 10*a*, 10*b* (at step 1606). In order to complete the embolus removal, the user may thereby deflate the balloon 18*a*, 18*b* (at step 1608) and withdraw the guiding sheath 10*a*, 10*b* through the arteriotomy in the carotid artery (at step 1610).

Figure 17:
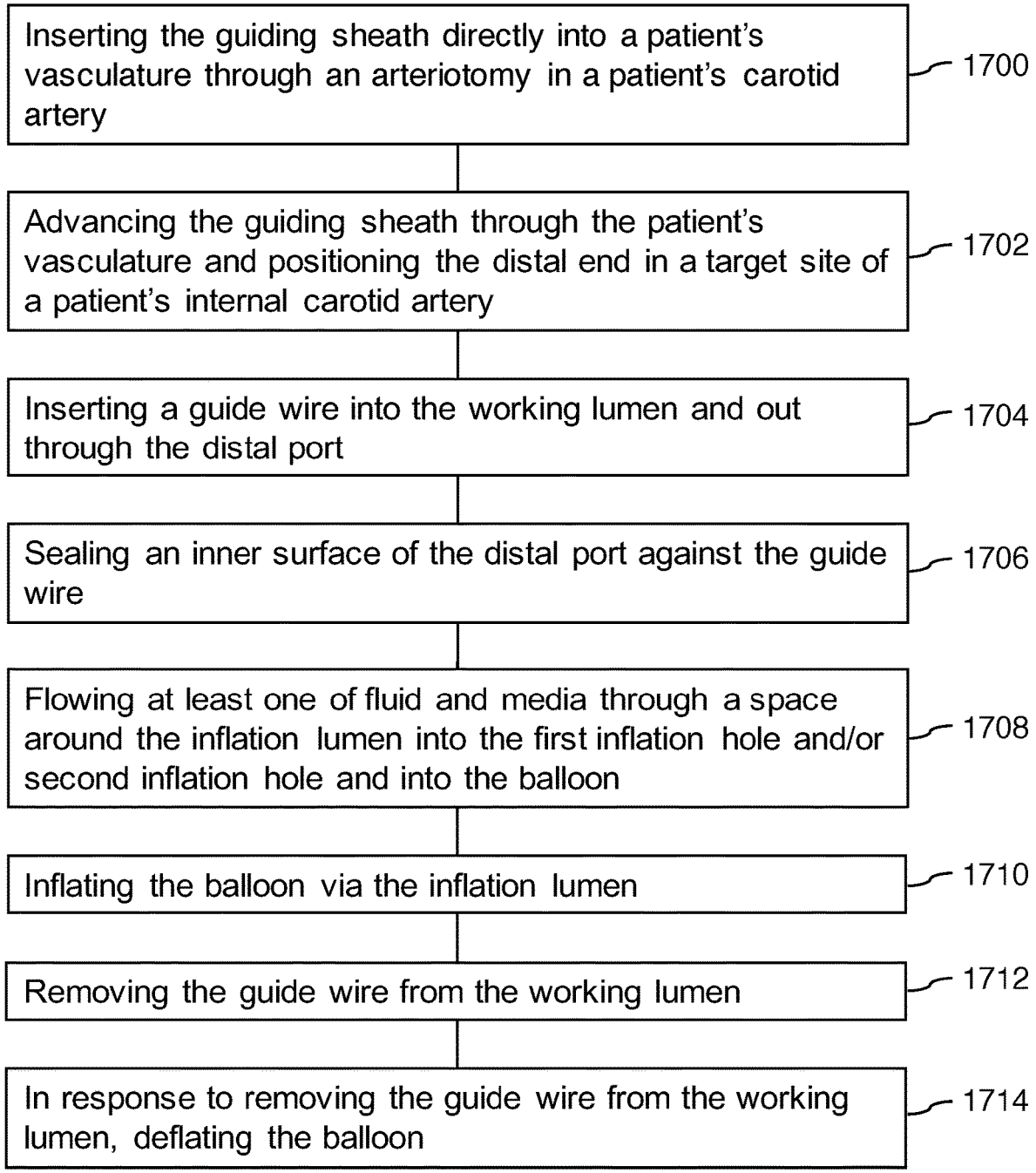

As shown in FIG. 17, the method may also include specific method steps to be performed with balloon guiding sheath 10*b*. In some embodiments, methods include inserting the guiding sheath 10*b* directly into a patient's vasculature through an arteriotomy in a patient's carotid artery (at step 1700). The user may then advance the guiding sheath 10*b* through the patient's vasculature and position the distal end in a target site of a patient's internal carotid artery (at step 1702).

In order to begin the balloon inflation process, the user may insert a guide wire 84 into the working lumen 22*b* and out through the distal port 20*b* (at step 1704) to thereby seal an inner surface of the distal port 20*b* against the guide wire 84 (at step 1706). Once the distal port 20*b* has been sealed, methods may include flowing fluid and/or media through a space around the inflation lumen 30*b* into the first inflation hole 80 and/or second inflation hole 82 and into the balloon 18*b* to inflate the balloon 18*b* (at step 1708). As the fluid and/or media flows into the balloon 18*b* via the inflation lumen 30*b*, the balloon 18*b* may become inflated (at step 1710) to occlude the artery.

Once the balloon 18*b* has been inflated, the user may perform none or any combination of steps 1600, 1602, 1604, and/or 1606 in order to remove the embolus. Upon completion of such steps, the user may remove the guide wire 84 from the working lumen 22*b* (at step 1712). As such, the working lumen 22*b* and the inflation lumen 30*b* may once again be in fluid communication, which means that the inflation lumen 30*b* is not able to adequately flow liquid and/or media into the balloon 18*b* to keep the balloon inflated. As such, in response to removing the guide wire 84 from the working lumen 22*b*, the balloon 18*b* may deflate (at step 1714).

Figure 18:
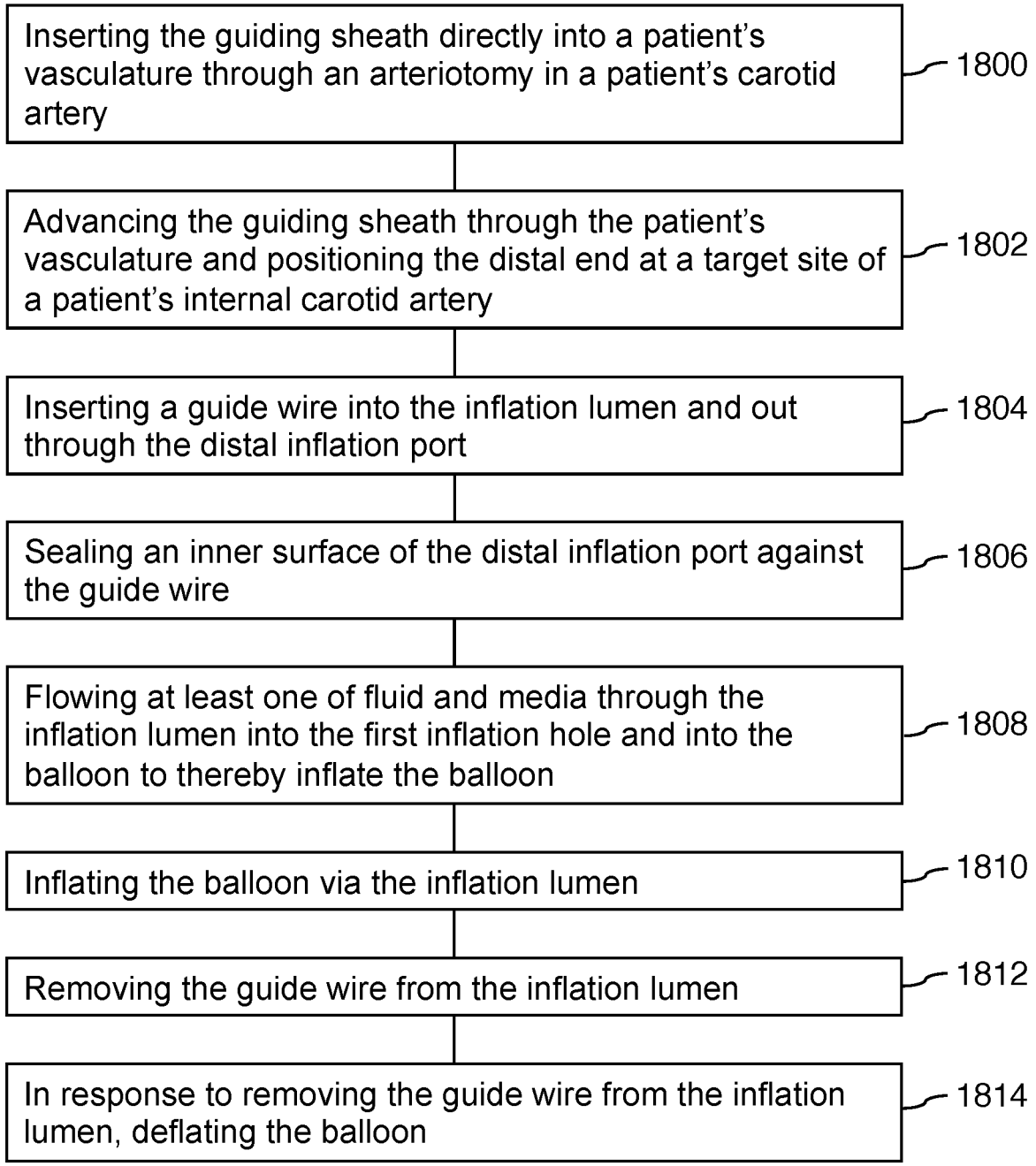

As illustrated in FIG. 18, methods may include steps for using a tip-occluding embodiment whereby the inflation lumen 30*c* is not in fluid communication with the working lumen 22*c*. Using such embodiments, methods may include inserting the guiding sheath 10*c* directly into a patient's vasculature through an arteriotomy in a patient's carotid artery (at step 1800). Methods may also include advancing the guiding sheath 10c through the patient's vasculature and positioning the distal end at a target site of a patient's internal carotid artery (at step 1802).

Once the guiding sheath 10c has been positioned in its desired location within the patient's carotid artery, methods may include inserting a guide wire 84 into the inflation lumen 30c and out through the distal inflation port 21 (at step 1804) and sealing an inner surface of the distal inflation port 21 against the guide wire 84 (at step 1806). Once the seal has been created, the method may include flowing at least one of fluid and media through the inflation lumen 30c into the first inflation hole 80 and into the balloon 18c to thereby inflate the balloon 18c (at step 1808) and thereby inflating the balloon 18c via the inflation lumen 30c (at step 1810).

In order to deflate the balloon 18c, methods may include removing the guide wire 84 from the inflation lumen 30c (at step 1812). In response to removing the guide wire 84 from the inflation lumen 30c, methods may include the step of deflating the balloon 18c (at step 1814).

Figure 19:
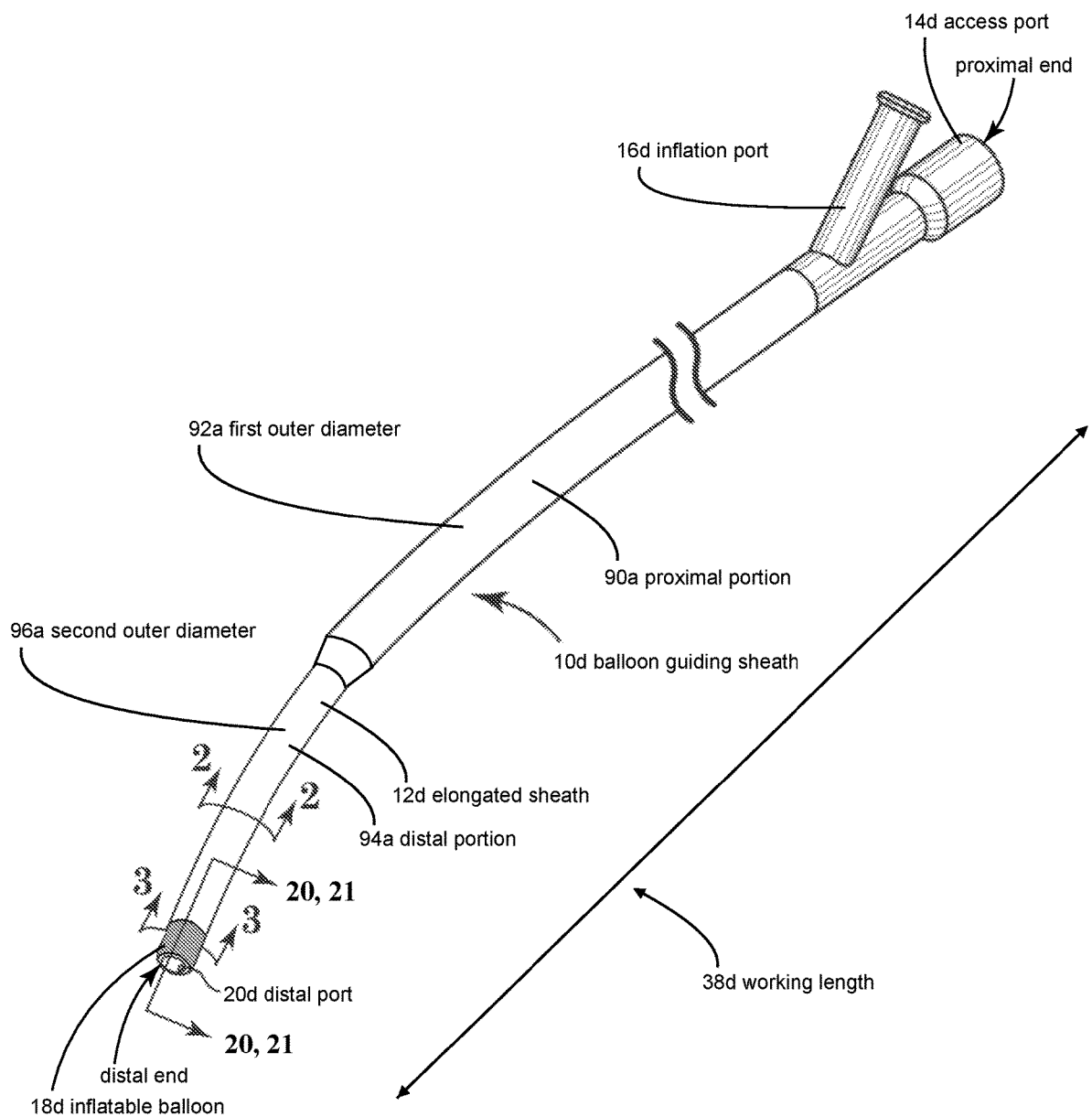
FIG. 19 illustrates another balloon guiding sheath, according to some embodiments.
Figure 20A:
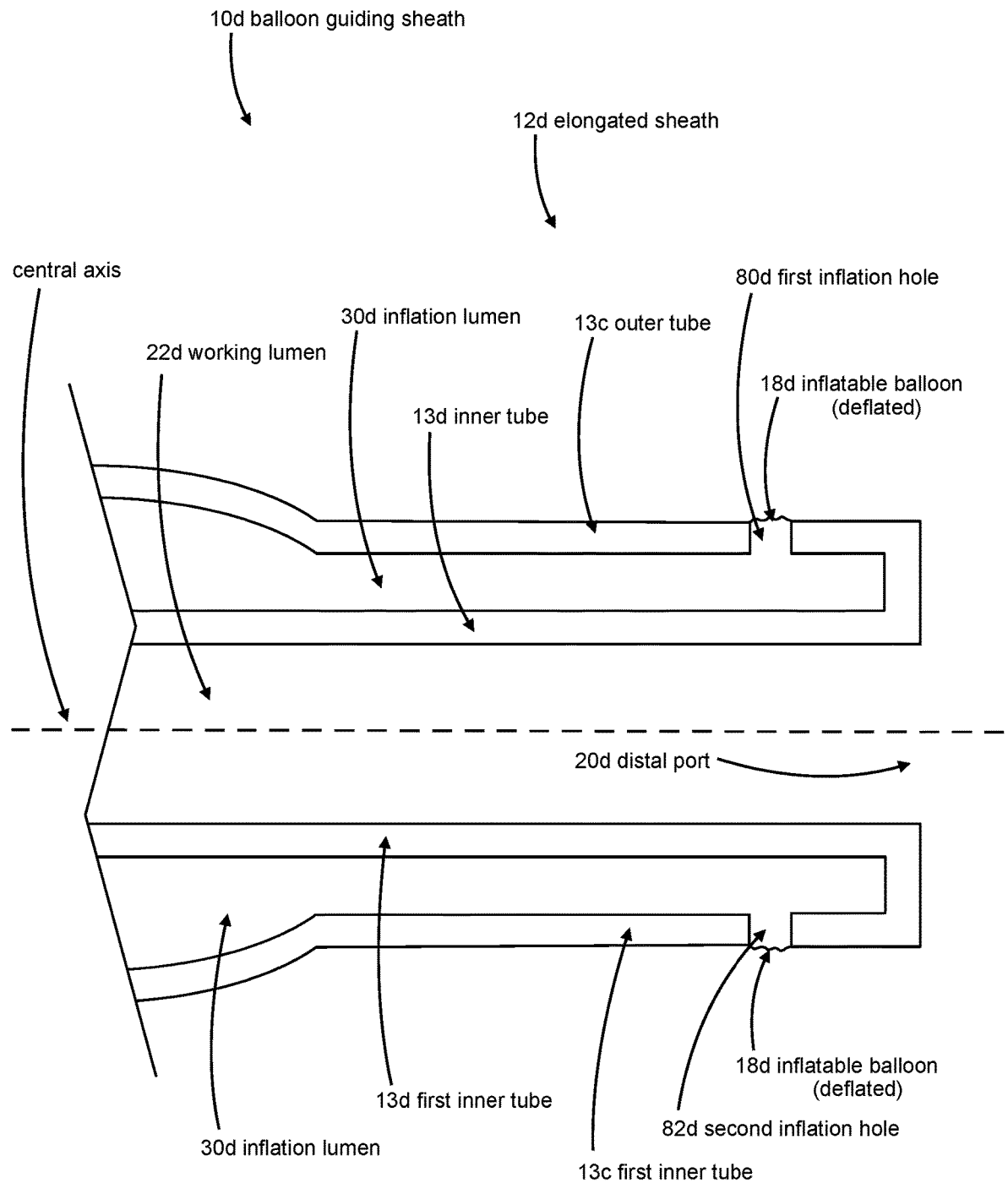
FIGS. 20A and 20B illustrate cross-sectional views of section 20-20 of the balloon guiding sheath, according to some embodiments.
Figure 20B:
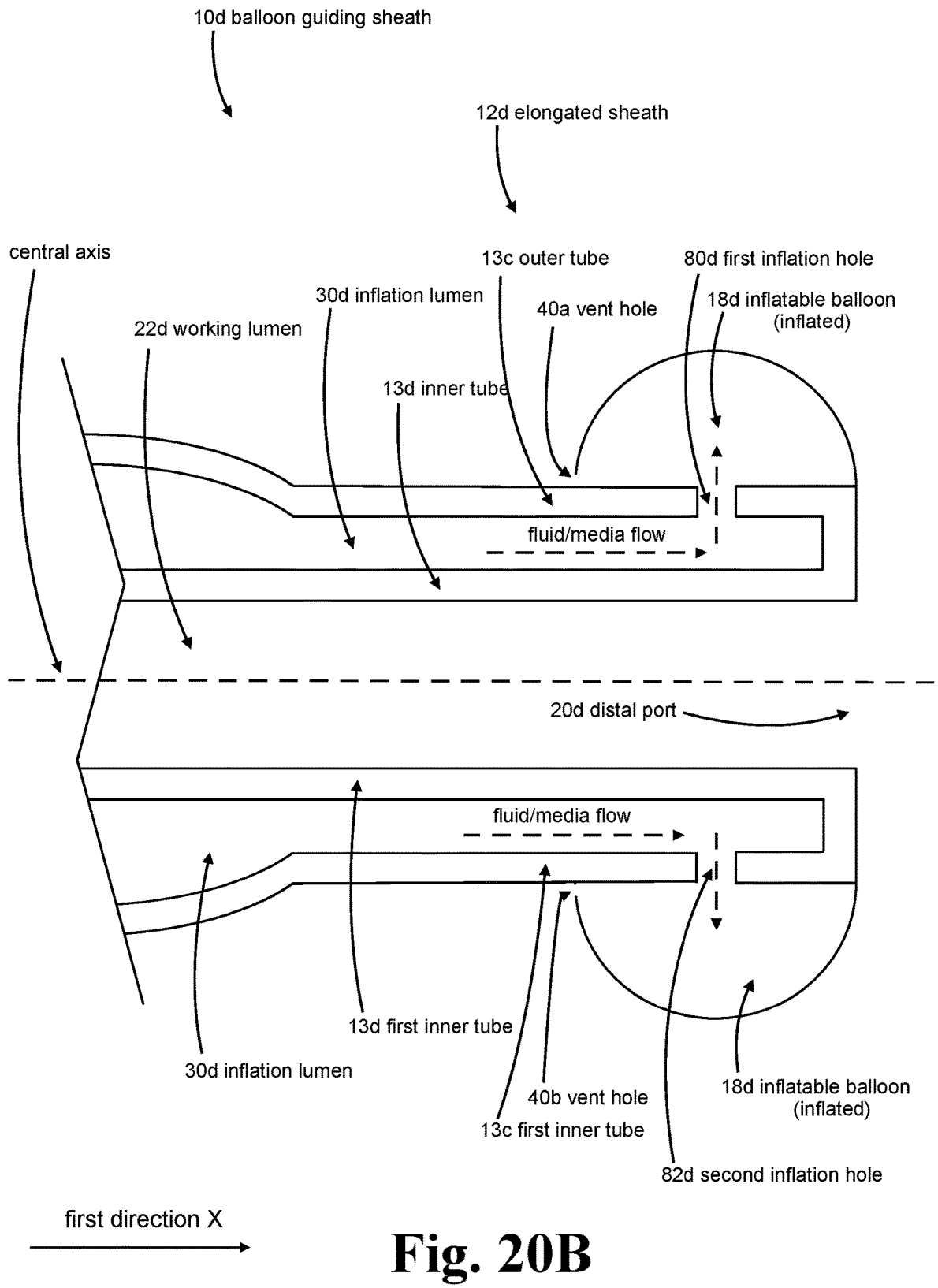
Figure 21:
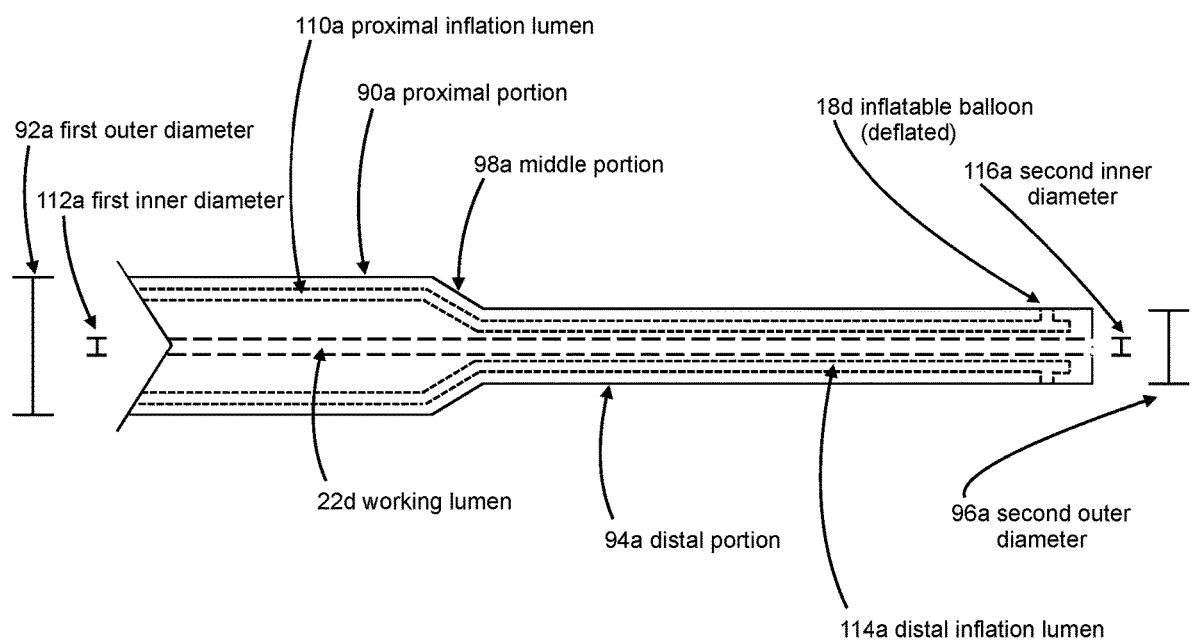
FIG. 21 illustrates a cross-sectional view of section 21-21 of the balloon guiding sheath, according to some embodiments.

A balloon guiding sheath 10d in accordance with embodiments of the invention can be described generally with reference to FIGS. 19-21. As shown in FIG. 19, a balloon guiding sheath 10d may comprise an elongated sheath 12d having a proximal end, a distal end, a proximal portion 90a defining a first outer diameter 92a, and a distal portion 94a defining a second outer diameter 96a. With reference to FIGS. 20A and 20B, the elongated sheath 12d may include an inner tube 13c and an outer tube 13d that surrounds the inner tube 13c. It should be appreciated that many embodiments may also be implemented with other tube arrangements, as will be discussed later regarding FIGS. 22-24. Other embodiments may include two, three, or four or more tubes, also referred to as layers.

Similar to other embodiments described throughout this disclosure, the components of the balloon guiding sheath 10d may be formed from a polymer (e.g. polytetrafluoroethylene, nylon, and the like). In some embodiments, the components may comprise Pellethane 65D or higher. Generally, the material selection may be focused on enhancing pushability in the balloon guiding sheath 10d as opposed to flexibility. However, it should be appreciated that in some embodiments the material selection may be focused on either or both pushability and/or flexibility. Generally, in many embodiments, the elongated sheath 12d is arranged and configured to have sufficient stiffness and tip flexibility to enable insertion of the working length 38d of the elongated sheath 12d into a patient's vasculature through an arteriotomy in the patient's femoral artery to position the distal port 20 at a target site in at least one of a petrous portion 54 of a patient's internal carotid artery 50, a cavernous portion 56 of a patient's internal carotid artery 50, and a cerebral portion 58 of a patient's internal carotid artery 50.

As shown in FIG. 19, the guiding sheath 10d may include an access port 14d located on the proximal end and an inflation port 16d also located on the proximal end. The guiding sheath 10d may include an inflatable balloon 18d coupled to the distal end and a distal port 20d also located on the distal end. As shown in FIGS. 20a and 20b, the guiding sheath 10d may include a working lumen 22d extending through the elongated sheath 12 between the access port 14d and the distal port 20d.

Furthermore, the guiding sheath 10d may include an inflation lumen 30d that extends between the inflation port 16d and the balloon 18d. In the embodiment disclosed with respect to FIGS. 19-21, the inflation lumen 30d is located between the inner tube 13c and the outer tube 13d. As illustrated, the inflation lumen 30d is not in fluid communication with the working lumen 22d.

With reference back to FIG. 3A, the guiding sheath 10d may include a reinforcement layer 31 located between the inner tube 13c and the outer tube 13d. The reinforcement layer 31 may be arranged and configured to enable flow of at least one of fluid and media through the inflation lumen 30d to thereby inflate the balloon 18d. The reinforcement layer 31 may be comprised of coiled and/or braided strands of material (e.g. stainless steel or polymer wire). It should be appreciated that any of the components described with respect to different embodiments may thereby be implemented with respect to any embodiment described throughout this disclosure.

Now with reference to FIGS. 20A and 20B, a cross-sectional side view of section 20-20 is shown. As shown, the balloon 18d may move between a deflated state (FIG. 20A) and an inflated state (FIG. 20B). The inflation and deflation may occur in response to fluid and/or media traveling through the inflation lumen 30d, through a respective inflation hole(s) 80d, 82d (e.g. first inflation hole 80d and second inflation hole 82d), and into the balloon 18d. In such embodiments, the inflation lumen 30d is not in fluid communication with working lumen 22d. In this regard, the balloon 18d may inflate and deflate irrespective of any interaction with the working lumen 22d. In doing so, the clinician may thereby occlude blood flow through the patient's artery while moving devices and tools through the working lumen 22d without interfering with balloon 18d inflation and deflation.

In many embodiments, the elongated sheath 12d is sized and configured to enable direct insertion into a patient's vasculature through an arteriotomy in the patient's femoral artery to position the balloon 18d at a target site. As shown in FIG. 21, which illustrates a cross-sectional side view of section 21-21, the first outer diameter 92a may be greater than the second outer diameter 96a. As such, the elongated sheath 12d may not have a generally constant outer diameter along its working length 38d.

With regard to specific dimensions, in some embodiments, the first outer diameter 92a is approximately equal to 0.123 inches. Even still, in some embodiments, the first outer diameter 92a is approximately equal to 0.137 inches. The second outer diameter 96a may be approximately equal to 0.104 inches such that the elongated sheath 12d fits through an 8 French (Fr) opening. In some embodiments, the second outer diameter 96a is approximately equal to 0.124 inches such that the elongated sheath 12d fits through a 10 French (Fr) opening. Generally, it should be appreciated that the first outer diameter 92a, second outer diameter 96a, and any other dimension recited in this disclosure may be equal to any value based on medical application and patient anatomy.

With continued reference to FIG. 21, the inflation lumen 30d may include a proximal inflation lumen 110a, indicated by broken lines, which extends from the inflation port 16d to a middle portion 98a located between the proximal portion 90a and the distal portion 94a. Additionally, the inflation lumen 30d may include a distal inflation lumen 114a, represented in broken lines, which extends from the middle portion 98a to the balloon 18d. In this regard, the distal inflation lumen 114a may be located between the inner tube 13c and the outer tube 13d.

Again, in regards to various commercial embodiments, the proximal and distal portions 90a, 94a may define a variety of different dimensions arranged and configured to meet the needs of specific applications and patient anatomies. For example, the working lumen 22d may define an inner diameter having a substantially constant diameter from the distal end to the proximal end. Specifically, in some embodiments, the inner diameter is approximately equal to 0.088 inches.

However, in many embodiments, the working lumen 22d does not define a constant inner diameter from the distal end to the proximal end. In some embodiments, the proximal portion 90a of the working lumen 22d defines a first inner diameter 112a approximately equal to 0.090 inches, while the distal portion 94a of the working lumen 22d defines a second inner diameter 116a greater than or equal to 0.086 inches and less than or equal to 0.090 inches. Even still, in some embodiments, the first inner diameter 112a is greater than or equal to 0.101 inches and less than or equal to 0.113 inches, and the second inner diameter 116a is greater than or equal to 0.101 inches and less than or equal to 0.113 inches. With even more specificity, in some embodiments, the first inner diameter 112a is approximately equal to 0.113 inches and the second inner diameter 116a is approximately equal to 0.101 inches.

The elongated sheath 12d may define a variety of working lengths sized and configured to accommodate treatment locations in different target sites. In some embodiments, the working length 38d is long enough to enable the distal end to reach at least a cervical portion 52 of a patient's internal carotid artery 50 from the femoral artery. The working length 38d may be long enough to enable the distal end to reach at least a petrous portion 54 of the patient's internal carotid artery 50 from the femoral artery. Even still, the working length 38d may be long enough to enable the distal end to reach at least a cavernous portion 56 of the patient's internal carotid artery 50 from the femoral artery. In some embodiments, the working length 38d is approximately equal to 95 centimeters. However, it should be appreciated that the working length 38d may be any length less than or greater than 95 centimeters. In some embodiments, the proximal portion 90a of the working lumen 22d equals approximately 85 centimeters in length, while the distal portion 94a of the working lumen 22d equals approximately 10 centimeters in length. However, the lengths of the proximal portion 90a and the distal portion 94a may define any length such that they equal the overall working length 38d.

Figure 22:
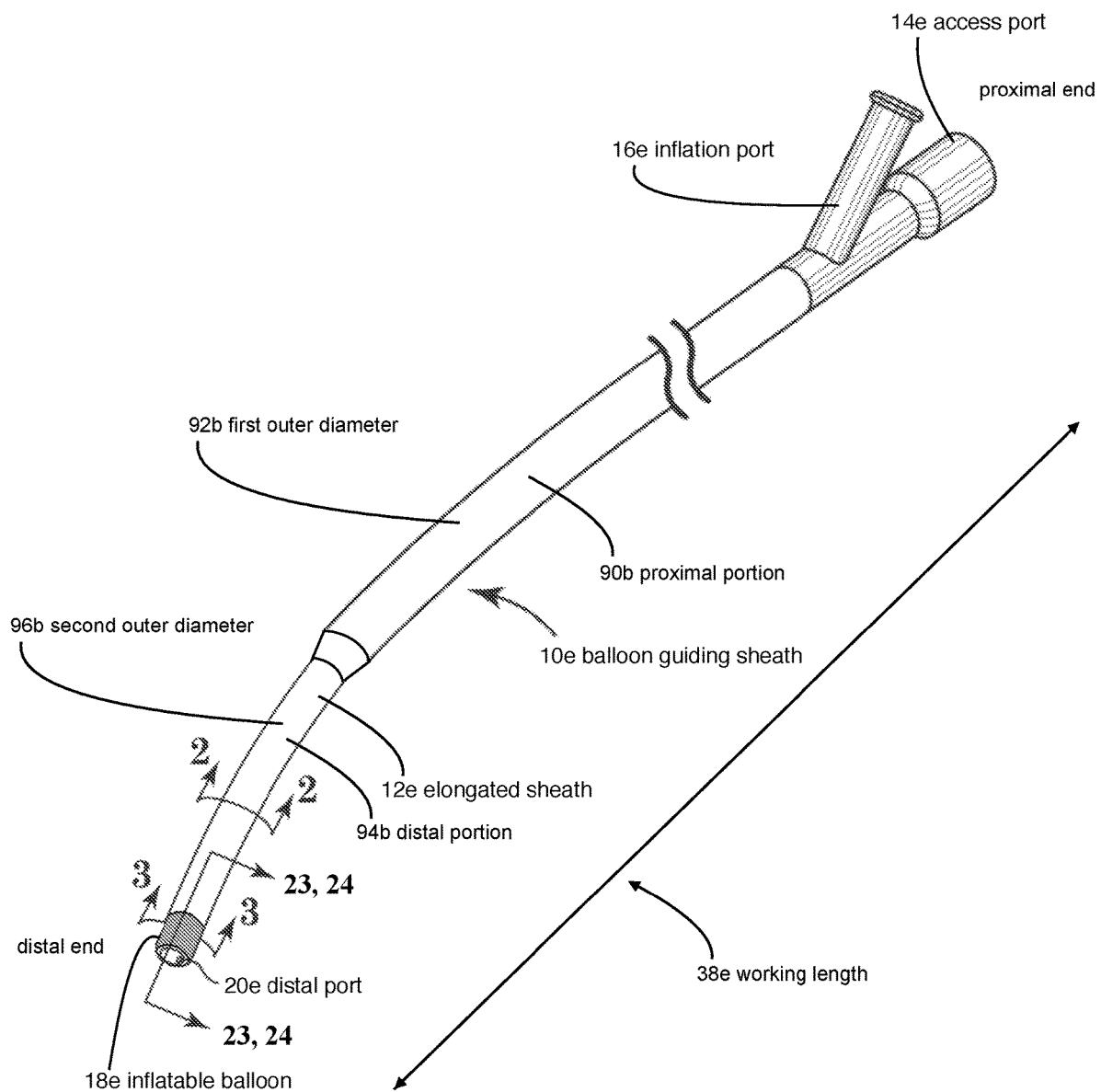
FIG. 22 illustrates yet another balloon guiding sheath, according to some embodiments.

Yet another balloon guiding sheath 10e in accordance with embodiments of the invention is now described with reference to FIGS. 22-24. As shown in FIG. 22, the guiding sheath 10e includes an elongated sheath 12e having a proximal end and a distal end. The guiding sheath 10e may include an access port 14e located on the proximal end and a distal port 20e located on the distal end. As well, the guiding sheath 10e includes a working lumen 22e extending through the elongated sheath 12e between the access port 14e and the distal port 20e. Similar to other embodiments disclosed, the guiding sheath 10e includes an inflation port 16e located on the proximal end and an inflation lumen 30e extending through the elongated sheath 12e between the inflation port 16e and the balloon 18e.

Figure 23A:
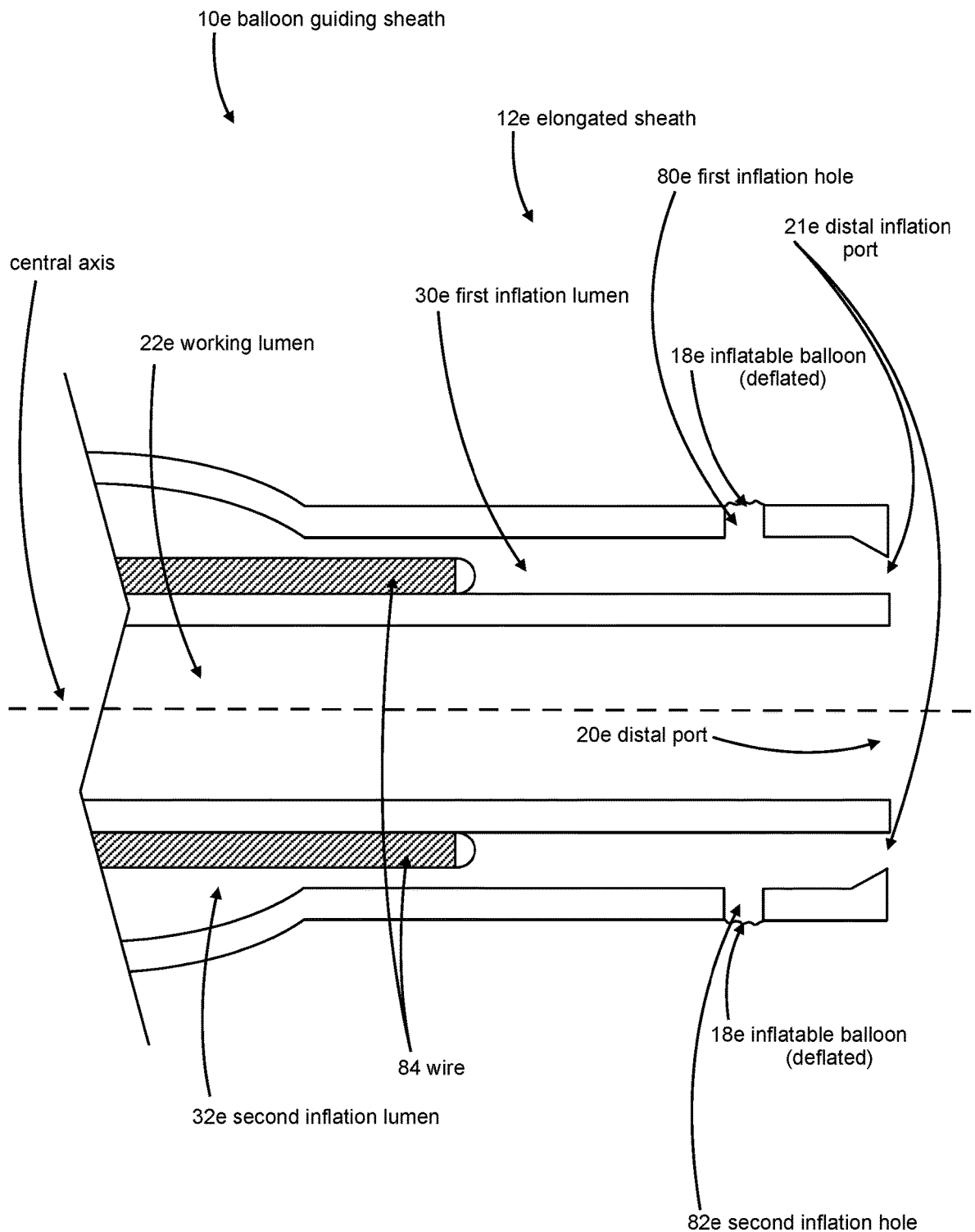
FIGS. 23A and 23B illustrate cross-sectional views of section 23-23 of the balloon guiding sheath, according to some embodiments.
Figure 23B:
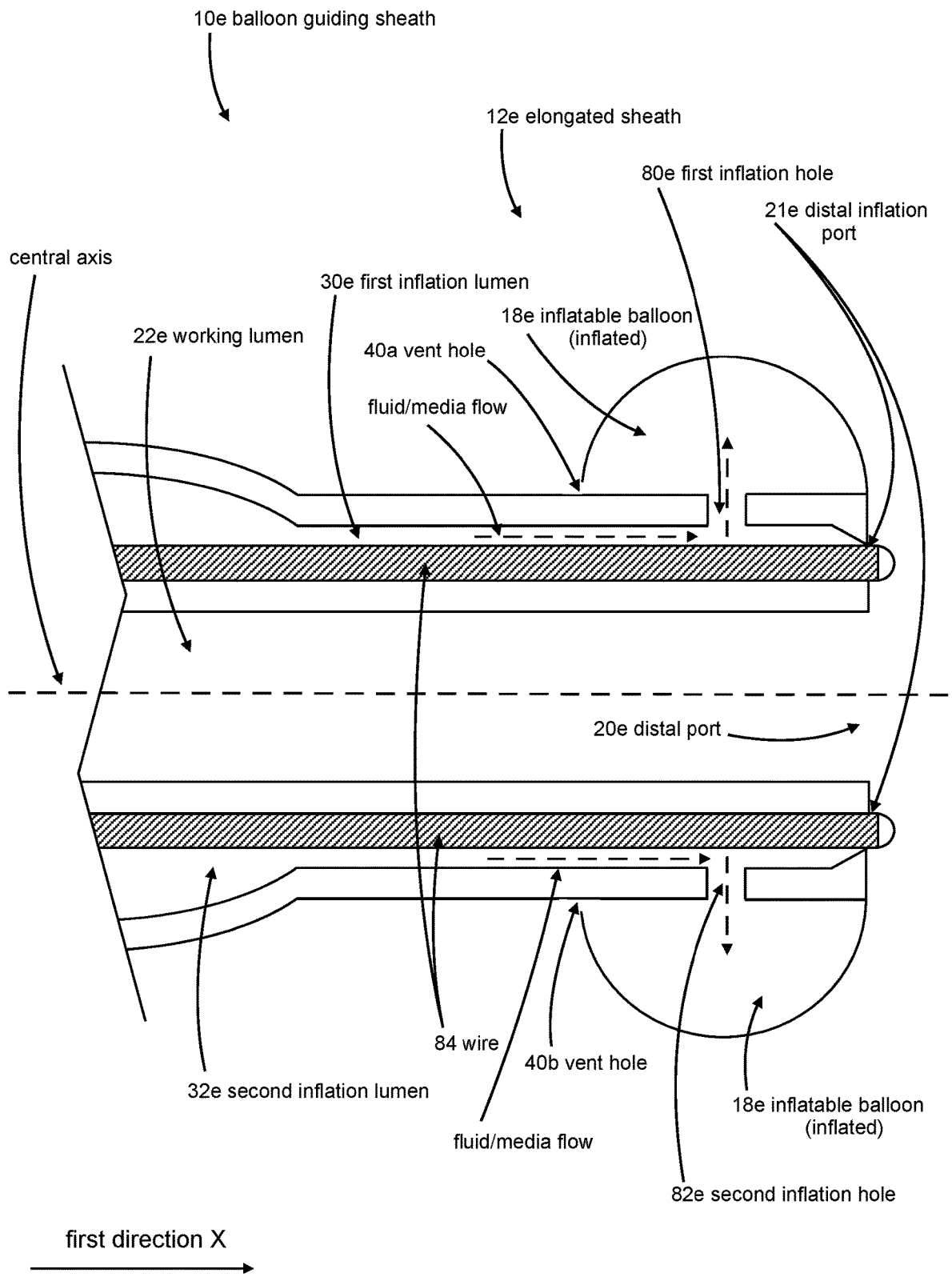

With respect to FIGS. 23A and 23B, which illustrate a cross-sectional side view of section 23-23, the inflation lumen 30e may include a distal inflation port 21e extending through an endwall of the elongated sheath 12e. The inflation lumen 30e may not be in fluid communication with the working lumen 22e between the access port 14e and the distal port 20e. The guiding sheath 10e may also include one or more inflation hole(s) 80e, 82e extending from the inflation lumen 30e through a sidewall of the elongated sheath 12e and into the balloon(s) 18e.

Similar to the embodiment described with respect to FIGS. 12A and 12B, when a wire 84 is inserted into the inflation lumen 30e and out through the distal inflation port 21e, the distal inflation port 21e may thereby create a seal against the guide wire 84. Once the seal is created, the inflation lumen 30e may enable flow of at least one of fluid and media through the inflation lumen 30e into the one or more inflation hole(s) 80e, 82e and into the balloon 18e to thereby inflate the balloon 18e, as shown in FIG. 23B.

In some embodiments, the elongated sheath 12e includes more than one inflation lumen. For example, the balloon guiding sheath 10e may thereby include a second inflation lumen 32e extending through the elongated sheath 12e between the inflation port 16e and the balloon 18e. The second inflation lumen 32e may include a second distal inflation port 21e extending through the endwall of the elongated sheath 12e. In such embodiments, the second inflation lumen 32e is not in fluid communication with the working lumen 22e between the access port 14e and the distal port 20e. The guiding sheath 10e may thereby include a second inflation hole 82e extending from the second inflation lumen 32e through the sidewall of the elongated sheath 12e. Similar to the inflation technique described above, when a second wire 84 is inserted into the second inflation lumen 32e and out through the second distal inflation port 21e, the second distal inflation port 21e may thereby create a seal against the second wire 84. Once this occurs, the flow of fluid and/or media through the second inflation lumen 32e into the second inflation hole 82e and into the balloon 18e thereby inflates the balloon 18e.

Regarding specific orientations of the working lumen 22e with respect to the inflation lumen 30e, the elongated sheath 12e may define a central axis extending from the proximal end to the distal end. As shown in FIGS. 23A and 23B, at least a portion of the working lumen 22e may overlap the central axis of the elongated sheath 12e, while the inflation lumen 30e does not overlap the central axis of the elongated sheath 12e. As such, the inflation lumen 30e may be radially spaced from the working lumen 22e.

The elongated sheath 12e may be sized and configured to enable direct insertion into a patient's vasculature through an arteriotomy in the patient's femoral artery to position the balloon 18e at a target site. As shown in FIG. 24, which illustrates a cross-sectional side view of section 24-24, the elongated sheath 12e may have a proximal portion 90b defining a first outer diameter 92b, and a distal portion 94b defining a second outer diameter 96b. In some embodiments, the first outer diameter 92b may be greater than the second outer diameter 96b. As such, the elongated sheath 12e may not have a generally constant outer diameter, and instead have a varying outer diameter along its working length 38e.

Figure 24:
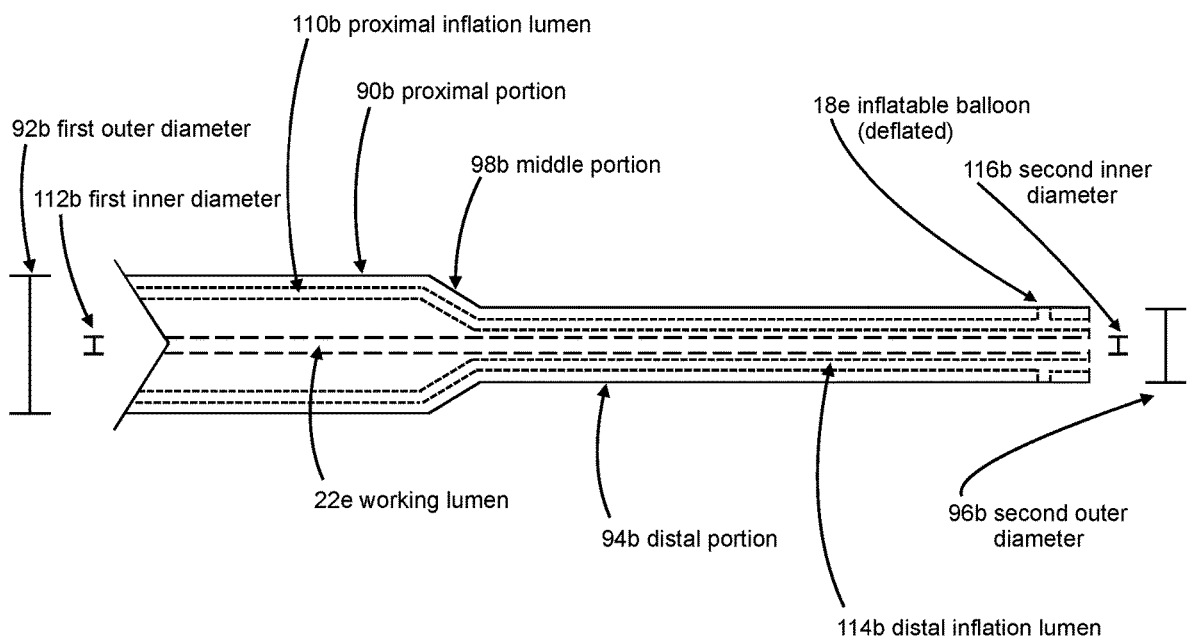
FIG. 24 illustrates a cross-sectional view of section 24-24 of the balloon guiding sheath, according to some embodiments.

With continued reference to FIG. 24, the inflation lumen 30e may include a proximal inflation lumen 110b, represented by the broken lines, which extends from the inflation port 16e to a middle portion 98b located between the proximal portion 90b and the distal portion 94b. Additionally, the inflation lumen 30e may include a distal inflation lumen 114b, represented by the broken lines, which extends from the middle portion 98b to the balloon 18e. In some embodiments, the proximal portion 90b of the working lumen 22e defines a first inner diameter 112b, while the distal portion 94b of the working lumen 22e defines a second inner diameter 116b.

Generally, embodiments disclosed with respect to FIGS. 22-24 may define any of the dimensions as previously defined throughout this disclosure. Generally, the guiding sheath 10e may be sized and configured such that the elongated sheath defines a working length long enough to enable the distal end to reach at least a cervical portion 52 of a patient's internal carotid artery 50 from the carotid artery. As well, the working length may be long enough to enable the distal end to reach a cavernous portion 56 of the patient's internal carotid artery 50 from the femoral artery.

Figure 25:
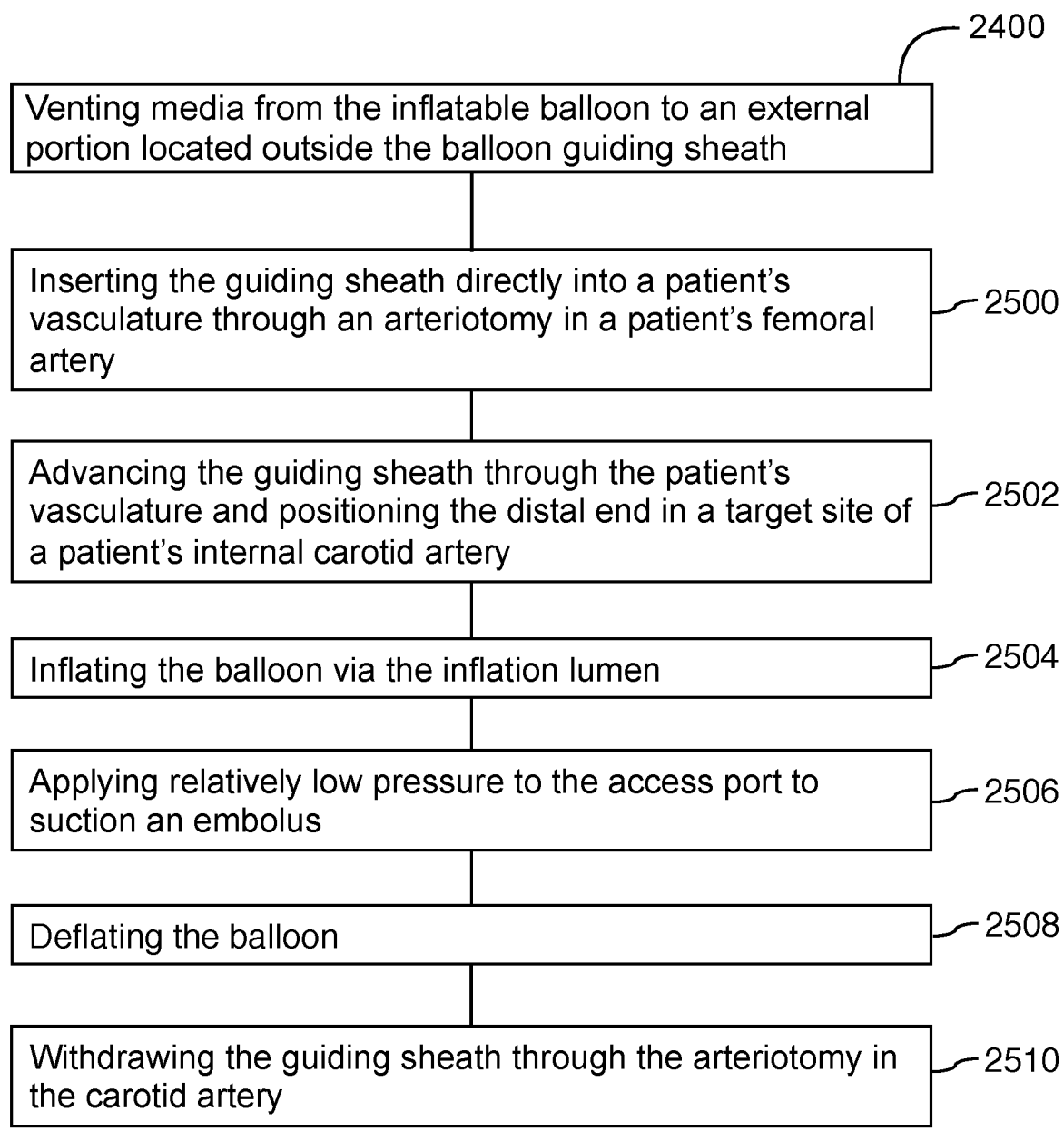
FIGS. 25, 26, and 27 illustrate methods of using a balloon guiding sheath, according to some embodiments.
Figure 26:
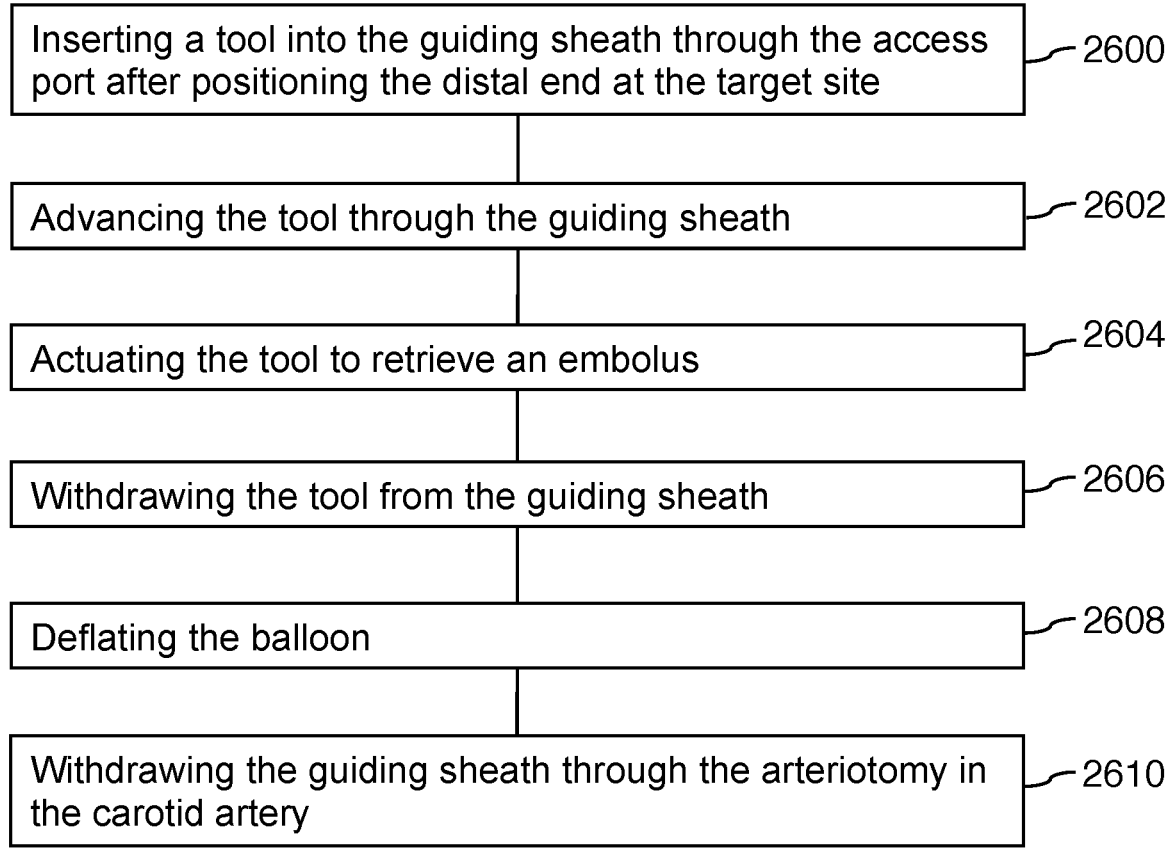
Figure 27:
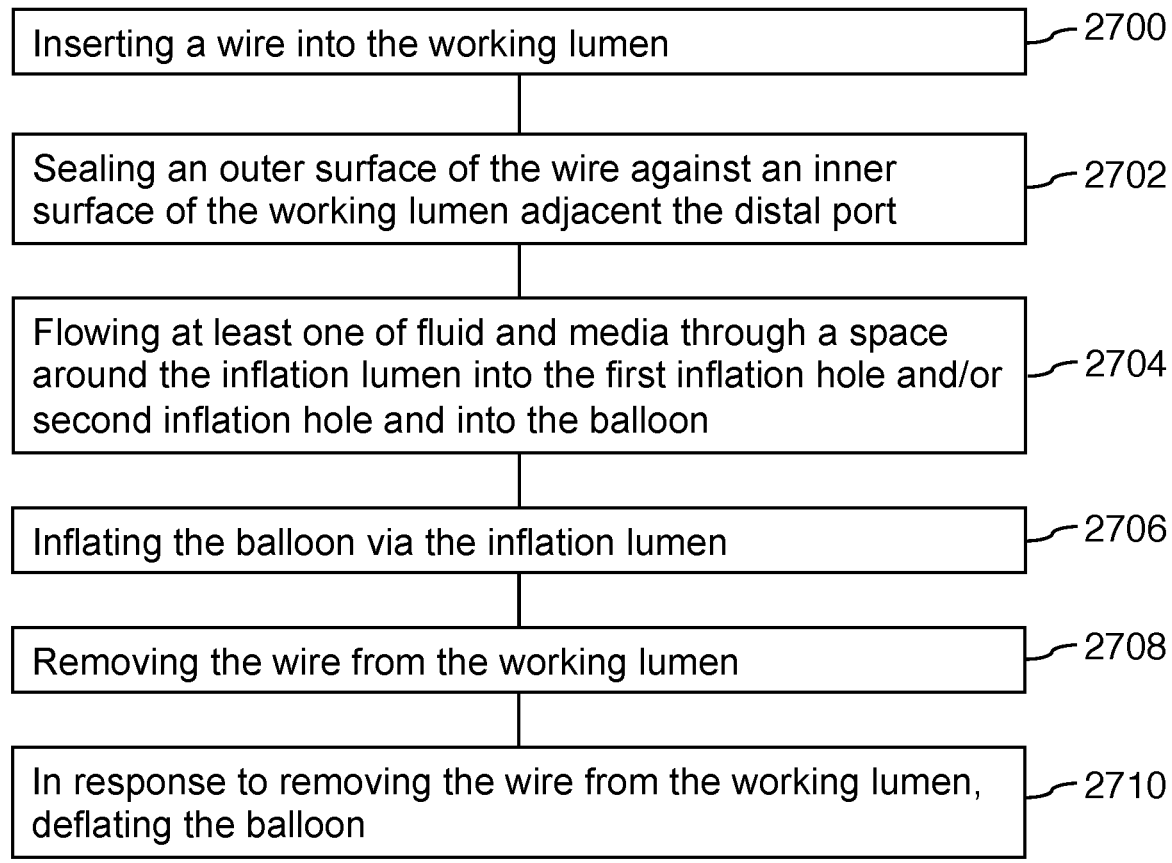

With reference to FIGS. 25-27, the disclosure also includes methods for using the balloon guiding sheaths 10d, 10e as described above. Some methods may be implemented with either guiding sheath 10d or 10e. However, some methods may only be implemented with embodiment 10e. Each circumstance is described in below.

As shown in FIG. 25, methods may include, inserting the guiding sheath 10d, 10e directly into a patient's vasculature through an arteriotomy in a patient's femoral artery (at step 2500), advancing the guiding sheath 10d, 10e through the patient's vasculature, and positioning the distal end in a target site of a patient's internal carotid artery (at step 2502). Methods may also include inflating the balloon 18d, 18e via the inflation lumen 30d, 30e (at step 2504). It should be appreciated that the target site may be a cervical portion 52 of the internal carotid artery 50, a petrous portion 54 of the internal carotid artery 50, and/or a cavernous portion 56 of the internal carotid artery 50.

As further shown, many methods include applying relatively low pressure to the access port 14d, 14e to suction an embolus (at step 2506). Once this is complete, methods may include deflating the balloon (at step 2508) and thereby withdrawing the guiding sheath 10d, 10e through the arteriotomy in the carotid artery (at step 2510).

However, clinicians may need to perform other treatments to the target site, which may require the use of additional equipment. Accordingly, methods may include the following intervening steps that may occur after step 2504. As shown in FIG. 26, such intervening steps may include inserting a tool into the guiding sheath 10d, 10e through the access port 14d, 14e after positioning the distal end at the target site (at step 2600), and advancing the tool through the guiding sheath 10d, 10e (at step 2602). Methods may thereby include actuating the tool to retrieve the embolus (at step 2604) and withdrawing the tool from the guiding sheath 10d, 10e (at step 2606). Once complete, methods may include deflating the balloon 18d, 18e (at step 2608) and withdrawing the guiding sheath 10d, 10e through the arteriotomy in the carotid artery (at step 2610).

As shown in FIG. 27, the method may also include specific method steps to be performed with balloon guiding sheath 10e. In accordance, inflating the balloon 18e via the inflation lumen 30e occurs in response to inserting a guide wire 84 into the working lumen 22e (at step 2700) and sealing an outer surface of the guide wire 84 against an inner surface of the working lumen 22e adjacent the distal port 20e (at step 2702). Methods may also include flowing at least one media through a space within the inflation lumen 30e between the wire 84 and an inner surface of the inflation lumen 30 and into at least one inflation hole 80e, 82e and into the balloon 18e (at step 2704), thereby inflating the balloon 18e (at step 2706).

In some embodiments, methods may also include removing the wire 84 from the working lumen 22e (at step 2708) and in response to removing the wire 84 from the working lumen 22e, deflating the balloon 18e (at step 2710).

When an air bubble enters an artery, the air bubble can travel to a patient's brain, heart, or lungs and cause a heart attack, stroke, or respiratory failure. Unfortunately, medical devices such as the balloon guiding sheath 10 may contain small amounts of trapped air that can be harmful to the patient. Accordingly, these air bubbles, or arterial air embolisms, must be expressed from the guiding sheath 10 before entering a patient's vasculature.

Accordingly, this disclosure includes embodiments arranged and configured to vent air bubbles and media from the inflatable balloon 18 to an external portion located outside of the balloon guiding sheath 10. Because air is lighter than the media located within the sheath 10, when pressure is applied at a proximal end of the inflation lumen 30, this may push the air bubble(s) through the inflation lumen 30, into the inflatable balloon 18, and out through at least one vent hole 40. The ability to vent media and/or air bubbles may assist in eliminating air from the inflatable balloon 18 and inflation lumen(s) 30 prior to treating a patient.

It should be appreciated that any of the balloon guiding sheaths 10 disclosed throughout this disclosure may include at least one vent hole 40. For example, as shown in FIGS. 2C, 11B, 12B, 20B and 23B, the at least one vent hole 40 may be located between an outer surface of the elongated sheath 12 and an inner surface of the inflatable balloon 18. In this regard, the at least one vent hole 40 may allow the inflatable balloon 18 to be in fluid communication with an external portion located outside the guiding sheath 10 to thereby vent (or emit) media and/or air bubbles from the balloon 18.

Once all of the air has been expressed from the balloon guiding sheath 10 prior to the sheath 10 entering the patient's vasculature, the sheath 10 may continue to express small amounts of media into the patient's vasculature during the actual treatment. With continued reference to FIGS. 2C, 11B, 12B, 20B and 23B, the at least one vent hole 40 may be located along a proximal edge 124 of the inflatable balloon 18, whereby the at least one vent hole extends towards an inner portion of the balloon 18. In this regard, because the at least one vent hole 40 is located along a proximal side 122 of the balloon 18, when media is vented from the balloon 18, the media may be exhausted in a direction that is away from the treatment site.

However, it should also be appreciated that the at least one vent hole 40 may be located along a distal side of the inflatable balloon 18 whereby the at least one vent hole 40 extends from the distal edge of the balloon 18 towards an inner portion of the balloon 18. As such, when the media is vented from the sheath 10, the media may be exhausted in a direction that is towards the treatment site.

The at least one vent hole 40 may be arranged in a variety of configurations. For example, as illustrated in FIG. 3B, the at least one vent hole 40 may include one or more vents (or pathways) located in various positions around the outer perimeter of the elongated sheath 12. In some embodiments, the one or more pathways defining the at least one vent hole 40 extend along a first direction X along the elongated sheath 12. In many embodiments, the at least one vent hole 40 does not extend radially around the perimeter of the balloon 18. However, it should be appreciated that in some embodiments, the at least one vent hole 40 extends along a direction that is different from the first direction X. In this regard, the at least one vent hole 40 may radially extend around at least a portion of the elongated sheath 12.

The balloon guiding sheath 10 may be configured such that every inflation lumen 30 is fluidly coupled to at least one vent hole 40. In this manner, the number of vent holes 40 may not be equal to the number of inflation lumens 30. Because the one or more inflation lumens 30 are fluidly coupled to at least one vent hole 40, this may ensure that all air is able to be expressed from every inflation lumen 30 and the inflatable balloon 18 within the guiding sheath 10. For example, in some embodiments, the guiding sheath 10 includes two inflation lumens 30 and one vent hole 40. Because the two inflation lumens 30 are in fluid communication with the inflatable balloon 18, which is in fluid communication with the one vent hole 40, this still allows the air to be pushed out of both inflation lumens 30.

However, it should be appreciated that some embodiments of the balloon guiding sheath 10 may include one dedicated vent hole 40 for every inflation lumen 30 included in the sheath 10. This may also ensure that all air is sufficiently expressed from every inflation lumen 30 prior to treatment.

The at least one vent hole 40 may define a narrow pathway, such as a round tubular hole, that fluidly couples the inner portion of the balloon 18 with the external portion of the balloon guiding sheath 10. The narrow opening of the at least one vent hole 40 may thereby limit the amount of media that is vented from the balloon 18. The narrow opening may also allow for a relatively low pressure to be applied on the inflatable balloon 18 to thereby keep the balloon 18 inflated. Because the at least one vent hole 40 may be round, it may define an inner diameter, which may be any size diameter such that it is sized and configured to meet the needs described thus far, such as effectively expressing air from the inflation lumen 30 and/or balloon 18 with relatively low pressure. However, it should be appreciated that the at least one vent hole 40 may define any geometric shape, such as a rectangle, oblong shape, and the like. Moreover, the dimensions of the at least one vent hole 40 may define any suitable size to accommodate the needs set forth within this disclosure.

In some embodiments, the at least one vent hole 40 comprises a first vent hole 40a and a second vent hole 40b radially spaced from the first vent hole 40a. In some embodiments, the first vent hole 40a is located opposite the second vent hole 40b along the elongated sheath 12. However, it should be appreciated the balloon guiding sheath 10 may include any number of vent holes 40, such as one vent hole, two vent holes, three vent holes, four vent holes, and five or more vent holes.

Furthermore, the disclosure also includes methods of use regarding embodiments having at least one vent hole 40. As shown in FIG. 25, methods may also include venting, via the at least one vent hole 40, media from the inflatable balloon to the external portion located outside the balloon guiding sheath 10 (at step 2400).

Figure 28:
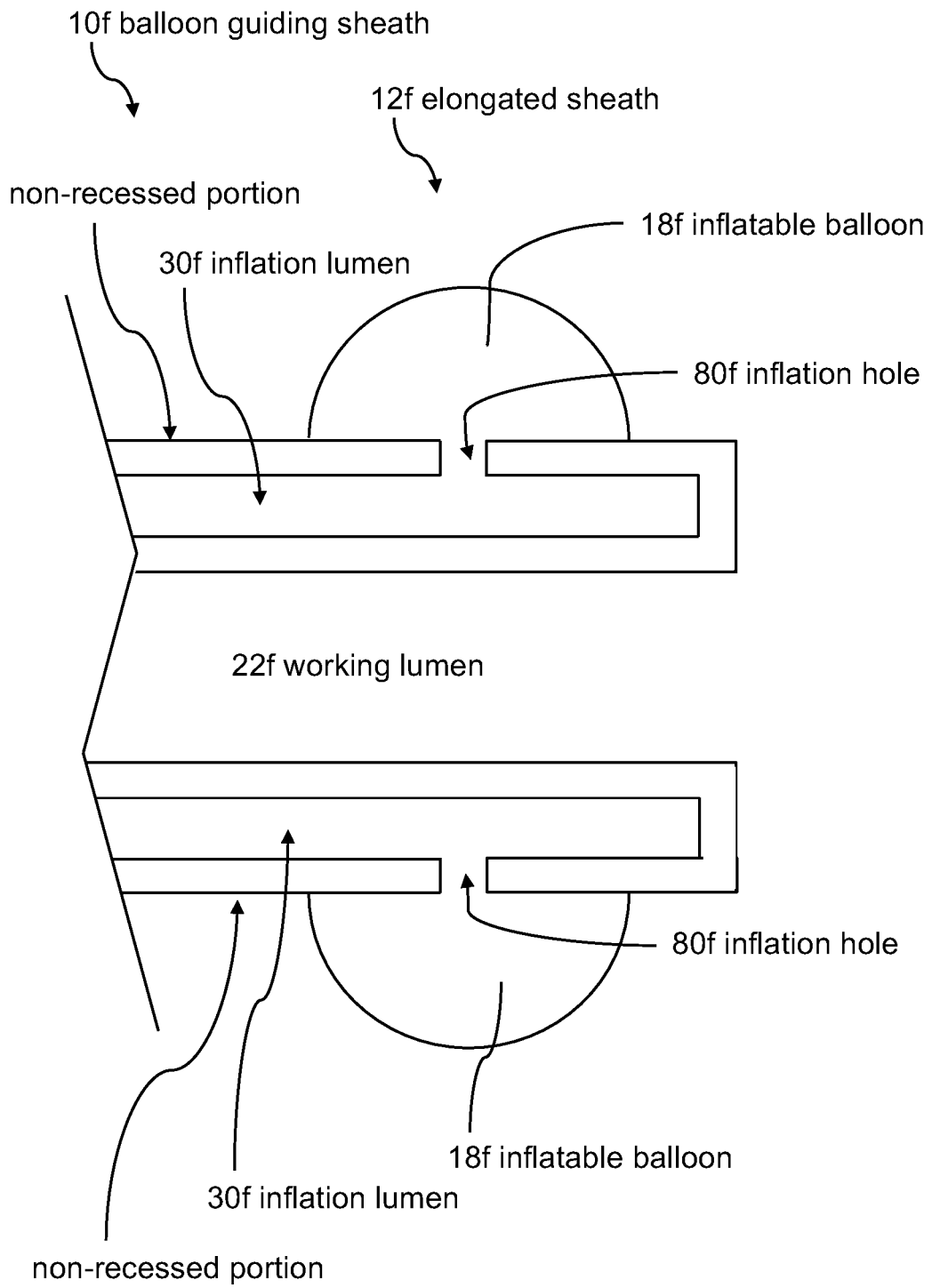
FIG. 28 illustrates a cross-sectional view of section 28-28 of the balloon guiding sheath, according to some embodiments.

FIG. 28 illustrates yet another embodiment of a balloon guiding sheath 10f and elongated sheath 12f. As shown, the inflatable balloon 18f (shown in the inflated state) is located in a non-recessed portion of the outer surface of the elongated sheath 12f. In such embodiments, the outer surface, or outer profile, of the elongated sheath 12f may define a zero profile whereby the inflatable balloon 18f is flush bonded to the outer surface of the elongated sheath 12f. This embodiment is unique with respect to the prior art (U.S. Pat. Nos. 6,638,245 and 6,702,782 assigned to Concentric Medical, Inc., see FIGS. 4a and 4b) because the outer surface of the elongated sheath 12f, as shown in FIG. 28, is able to achieve a generally constant outer diameter without having to recess the portion of the elongated sheath located beneath the inflatable balloon 18f.

As shown in various figures, such as FIGS. 1 and 28, in some embodiments, the inflatable balloon 18 is located in a non-recessed portion of the outer surface of the elongated sheath 12.

In some embodiments, the elongated sheath 12 is arranged and configured to have sufficient stiffness and tip flexibility to enable insertion of the working length of the sheath into a patient's vasculature through an arteriotomy in a patient's radial artery to position the distal port 20 at a target site in at least one of a petrous portion of a patient's internal carotid artery, a cavernous portion of the patient's internal carotid artery, and a cerebral portion of the patient's internal carotid artery.

The disclosure also includes a balloon guiding sheath 10 that includes an elongated sheath 12. As shown in FIGS. 2B, 2C, 3A, and 22, the elongated sheath 12 may include a proximal end, a distal end opposite the proximal end, an inner tube 13a, 13c extending between the proximal end and the distal end, an outer tube 13b, 13d surrounding the inner tube 13a, 13c and extending between the proximal end and the distal end, an access port 14 located adjacent the proximal end, a distal port 20 located adjacent the distal end, and a working lumen 22 extending through the elongated sheath 12 between the access port 14 and the distal port 20. The balloon guiding sheath 10 may also include an inflatable balloon 18 located on an outer surface of the elongated sheath 12 adjacent the distal end. The inflatable balloon 18 may be fluidly coupled to an inflation lumen 30, 32 extending between the inflatable balloon 18 and an inflation port 16 located adjacent the proximal end. As shown in FIG. 12B, the balloon guiding sheath 10 may also include at least one vent hole 40 located between an outer surface 118 of the elongated sheath 12 and an inner surface 120 of the inflatable balloon 18. The at least one vent hole 40 may allow media to flow from the inflatable balloon 18 to an external portion outside the balloon guiding sheath 10.

As illustrated in FIG. 1, the elongated sheath 12 may be sized and configured to enable insertion into a patient's vasculature through an arteriotomy in a patient's radial artery to position the inflatable balloon 18 at a target site to thereby remove the thrombus with the balloon guiding sheath 10s. The insertion site may be referred to as transradial arterial access.

As shown in FIGS. 2C and 12B, the at least one vent hole 40 may be located along a proximal side 122 of the inflatable balloon 18. Even still, in some embodiments, the at least one vent hole 40 is located along a proximal edge 124 of the inflatable balloon 18. The proximal side 122 may refer to any portion of the inflatable balloon located on the proximal half of the inflatable balloon. In this regard, if the inflatable balloon were divided into equal halves with respect to the third direction (as shown in FIG. 12B), the upper half, or the half located closer to the proximal tip, may include the proximal side 122, while the lower half, or the half located closer to the distal tip, may include the distal side. The proximal edge 124 may refer to the proximal most point of the inflatable balloon.

As shown in FIGS. 2C, 3B, 11B, 12B, 20B, and 23B. The at least one vent hole 40 may include a first vent hole 40a and a second vent hole 40b radially spaced from the first vent hole 40a. Furthermore, in some embodiments, the first vent hole 40a is located opposite the second vent hole 40b along the elongated sheath 12.

With reference to FIG. 3A, the balloon guiding sheath 12 may further comprise a reinforcement layer 31 located between the inner tube 13a and the outer tube 13b. In this regard, the reinforcement layer 31 may be arranged and configured to enable flow of at least one of fluid and media through the inflation lumen 30.

As shown in FIGS. 5, 8, 19, and 22, the elongated sheath may define a working length comprising a proximal portion located distal the proximal end, and a distal portion 94 located between the proximal portion 90 and the distal end, and the elongated sheath 12 defines a generally constant outer diameter from the proximal portion 90 to the distal portion 94.

In some embodiments, the generally constant outer diameter is equal to 0.123 inches. Additionally, in some embodiments, the generally constant outer diameter is equal to 0.110 inches. Even still, in some embodiments, the generally constant outer diameter is equal to 0.102 inches.

Figure 29A:
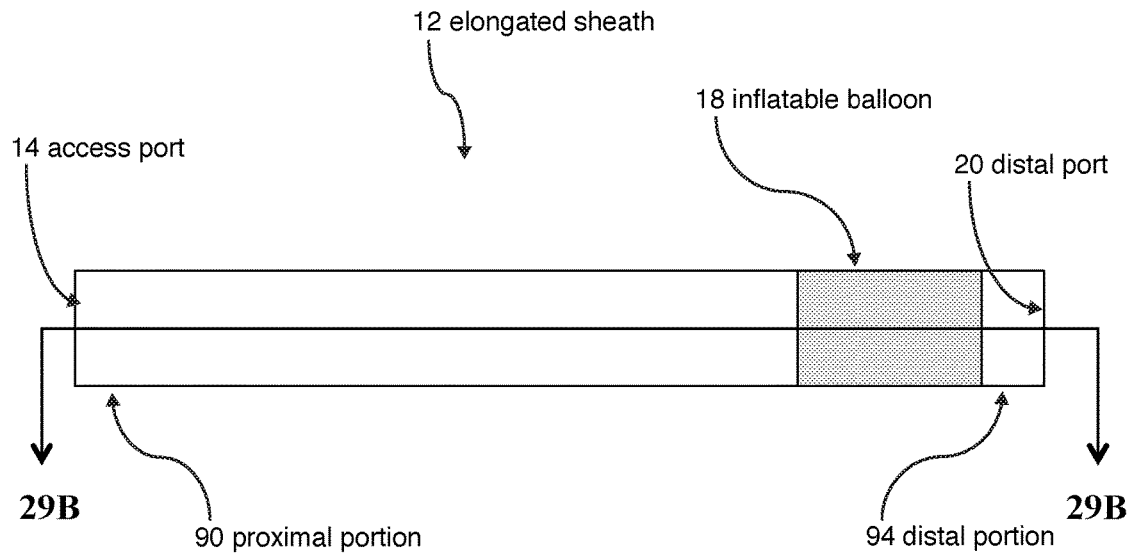
FIG. 29A illustrates another balloon guiding sheath, according to some embodiments.
Figure 29B:
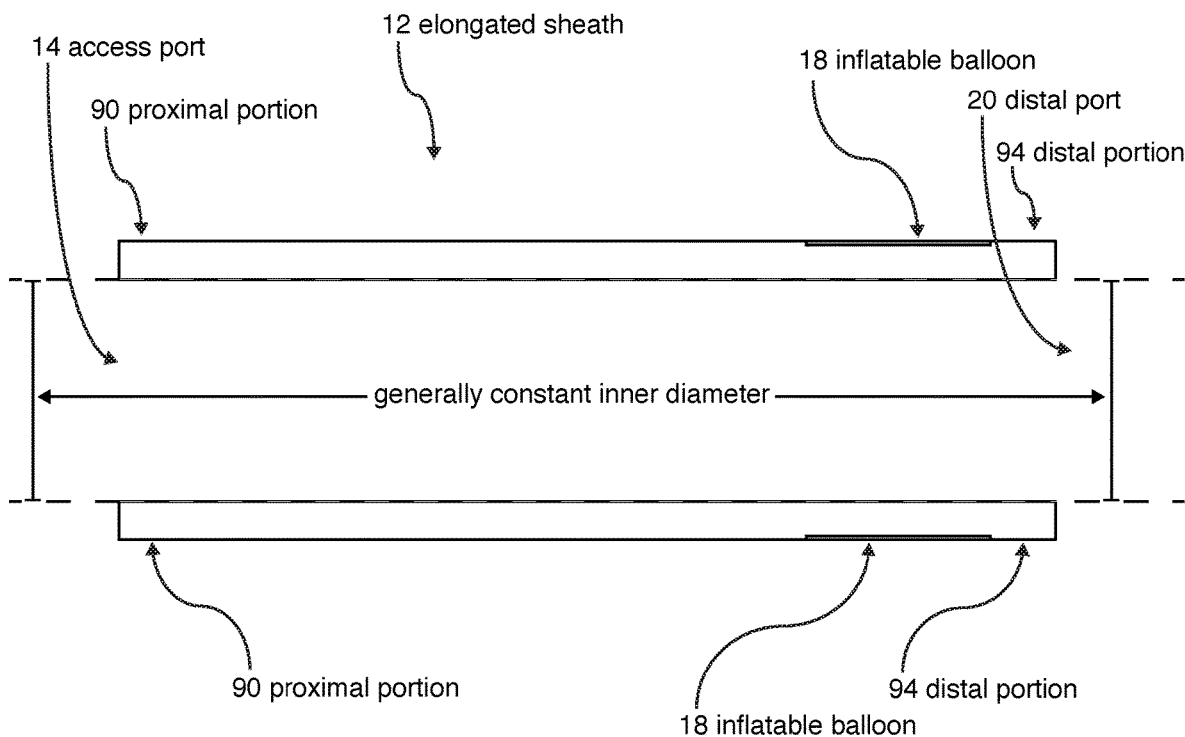
FIG. 29B illustrates a cross-sectional view of section 29-29 of the balloon guiding sheath, according to some embodiments.

Now with reference to FIGS. 29A and 29B, in some embodiments, the elongated sheath 12 defines a working length comprising a proximal portion 90 located distal the proximal end, and a distal portion 94 located between the proximal portion 90 and the distal end. The elongated sheath 12 may define a generally constant inner diameter from the proximal portion 90 to the distal portion 94. In some embodiments, the generally constant inner diameter extends from the access port to the distal port.

In some embodiments, the generally constant inner diameter is equal to 0.103 inches. As well, in some embodiments, the generally constant inner diameter is equal to 0.088 inches. Even still, in some embodiments, the generally constant inner diameter is equal to 0.087 inches.

Figure 30:
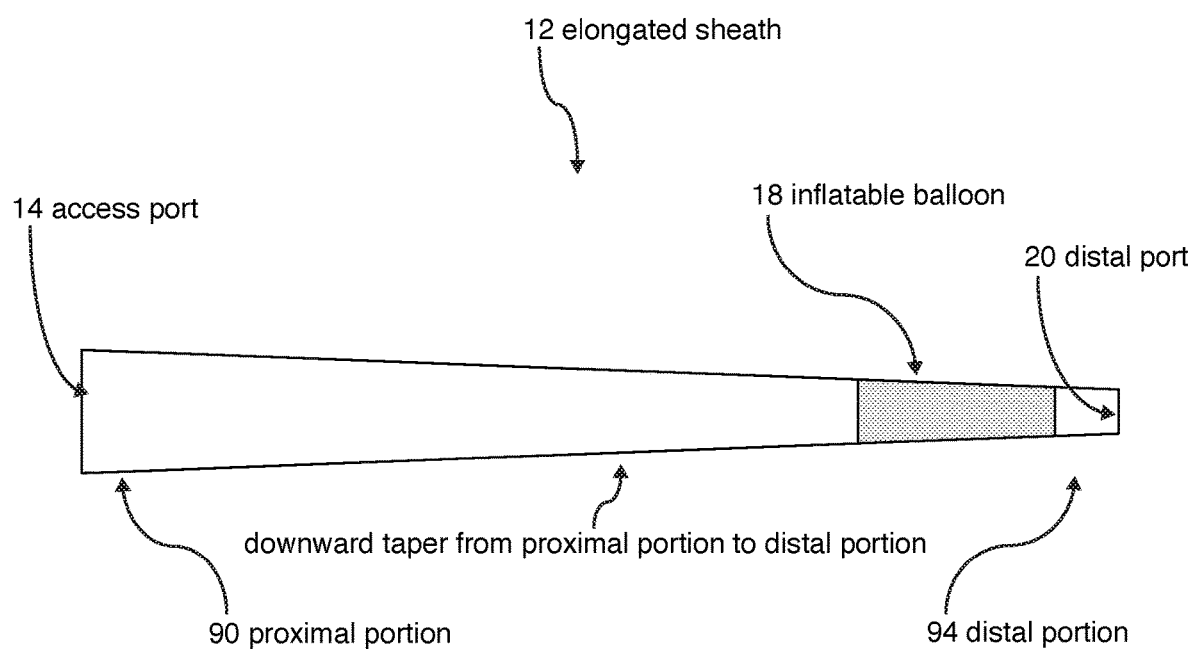
FIG. 30 illustrates another balloon guiding sheath, according to some embodiments.

FIG. 30 shows a simplified view of an elongated sheath 12 intended to illustrate the downward taper from the proximal portion 90 to the distal portion 94. In this regard, the elongated sheath 12 may define an outer diameter that tapers downward from the proximal portion 90 to the distal portion 94. In other words, in some embodiments, the outer diameter of the elongated sheath adjacent the proximal portion 90 is larger than the outer diameter adjacent the distal portion 94. The downward taper shown in FIG. 30 is exaggerated to illustrate the taper; however, the commercially deployed embodiment may have a more subtle downward taper from the proximal portion 90 to the distal portion 94.

Interpretation

Various portions of the disclosure refer to components by number, and some by letter as well. For example, the inflatable balloon may be referred to as inflatable balloon 18 and inflatable balloon 18f. It should be appreciated that the inflatable balloons 18 and 18f may be used interchangeably throughout any of the embodiments disclosed. In other words, inflatable balloon 18 may be deployed in an embodiment where the disclosure refers to inflatable balloon 18f, and vice versa. The component numbering and lettering scheme is not meant to be exclusive, but rather meant to be inclusive and to allow the components, by the same root name ("inflatable balloon"), to be used interchangeably despite having different letters (e.g., 18b or 18f). The same holds true for all components disclosed throughout.

As presented in this disclosure, the term "substantially" shall mean "for the most part." As such, if we say that a first object is substantially horizontally aligned with a second object this means that at least half a surface area of the first object overlaps with at least half a surface area of the second object. Within a numerical context "substantially" shall mean ±0.001 inches. For example, to say that an inner diameter of a working lumen is substantially equal to 0.091 inches, means that the inner diameter is 0.091±0.001 inches.

As presented in this disclosure, the term "generally" shall be interpreted numerically as ±0.003 inches. For example, to say that an elongated sheath defines a generally constant outer diameter shall mean that the outer diameter is generally constant but may vary by ±0.003 inches. For example, if the outer diameter is 0.123 inches and generally constant shall mean that the outer diameter may vary between 0.126 inches and 0.120 inches.

Furthermore, as presented in this disclosure, the term "about" shall mean approximately or roughly. Within a numerical context "about" shall mean ±0.5 centimeters. For example, to say that the length of a guiding sheath is about 90 centimeters, means that the guiding sheath is 90±0.5 centimeters.

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments include A, B, and C. The term "and/or" is used to avoid unnecessary redundancy.

Although the embodiments herein are described with various specific embodiments, it will be obvious for a person skilled in the art to practice the invention with modifications. However, all such modifications are deemed to be within the scope of the claims. While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

Furthermore, the foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A balloon guiding sheath, comprising: an elongated sheath having a proximal end, a distal end opposite the proximal end, an inner tube extending between the proximal end and the distal end, an outer tube surrounding the inner tube and extending between the proximal end and the distal end, an access port located adjacent the proximal end, a distal port located adjacent the distal end, and a working lumen extending through the elongated sheath between the access port and the distal port; an inflatable balloon located on an outer surface of the elongated sheath adjacent the distal end and configured to, in an inflated state, occlude blood flow through a vessel at a treatment site, the inflatable balloon being fluidly coupled to an inflation lumen extending between the inflatable balloon and an inflation port located adjacent the proximal end; and at least one vent hole located between the outer surface of the elongated sheath and an inner surface of the inflatable balloon and on only a proximal side of the inflatable balloon, wherein the at least one vent hole is fluidly coupled to the inflatable balloon and configured to allow air to flow from the inflatable balloon to an external portion outside the balloon guiding sheath, and wherein the at least one vent hole is configured to prevent liquid from passing through the at least one vent hole.

2. A balloon guiding sheath, comprising:
an elongated sheath defining a proximal end, a distal end opposite the proximal end, a working lumen, and an inflation lumen;
an inflatable balloon located on an outer surface of the elongated sheath and configured to, in an inflated state, occlude blood flow through a vessel at a treatment site, the inflatable balloon being fluidly coupled to the inflation lumen; and
at least one vent hole fluidly coupled to the inflatable balloon and configured to allow media to flow from the inflatable balloon to a location outside the balloon guiding sheath and vent air in the media, wherein the at least one vent hole is located on only a proximal side of the inflatable balloon to enable the media vented from the inflatable balloon to flow away from the treatment site.

3. The balloon guiding sheath of claim 2,
wherein the elongated sheath comprises an inner tube and an outer tube, and
wherein the inflation lumen is located between the inner and outer tubes.

4. The balloon guiding sheath of claim 3, further comprising a reinforcement layer located between the inner tube and the outer tube, the reinforcement layer arranged and configured to enable flow of at least one of the fluid or the media through the inflation lumen.

5. The balloon guiding sheath of claim 2, wherein the elongated sheath is sized and configured to enable insertion into vasculature of a patient through an arteriotomy in a radial artery of the patient to position the inflatable balloon at a target site.

6. The balloon guiding sheath of claim 2, wherein the at least one vent hole is located along a proximal edge of the inflatable balloon.

7. The balloon guiding sheath of claim 2, wherein the at least one vent hole comprises a first vent hole and a second vent hole radially spaced from the first vent hole.

8. The balloon guiding sheath of claim 7, wherein the first vent hole is located opposite the second vent hole along the elongated sheath.

9. The balloon guiding sheath of claim 2, wherein the elongated sheath defines the working length comprising a proximal portion located distal the proximal end, and a distal portion located between the proximal portion and the distal end, and wherein the elongated sheath defines a generally constant outer diameter from the proximal portion to the distal portion.

10. The balloon guiding sheath of claim 9, wherein the generally constant outer diameter is equal to 0.102 inches, 0.110 inches, or 0.123 inches.

11. The balloon guiding sheath of claim 2, wherein the elongated sheath defines the working length comprising a proximal portion located distal the proximal end, and a distal portion located between the proximal portion and the distal end, and wherein the elongated sheath defines a generally constant inner diameter from the proximal portion to the distal portion.

12. The balloon guiding sheath of claim 11, wherein the generally constant inner diameter is equal to 0.087 inches, 0.088 inches, or 0.103 inches.

13. The balloon guiding sheath of claim 2, wherein the elongated sheath defines the working length comprising a proximal portion located distal the proximal end, and a distal portion located between the proximal portion and the distal end, and wherein the elongated sheath defines an outer diameter that tapers downward from the proximal portion to the distal portion.

14. The balloon guiding sheath of claim 2, wherein the inflatable balloon is located in a non-recessed portion of the outer surface.

15. The balloon guiding sheath of claim 2, wherein the elongated sheath includes a distal port located adjacent the distal end and defines the working length long enough to enable the distal port to reach a cavernous portion of an internal carotid artery of a patient from a radial artery of the patient.

16. The balloon guiding sheath of claim 2, wherein the elongated sheath includes a distal port located adjacent the distal end and defines the working length, wherein the elongated sheath is arranged and configured to have sufficient stiffness and tip flexibility to enable insertion of the working length into a vasculature of a patient through an arteriotomy in a radial artery of the patient to position the distal port at a target site in at least one of a petrous portion of an internal carotid artery of the patient, a cavernous portion of the internal carotid artery of the patient, and a cerebral portion of the internal carotid artery of the patient.

17. The balloon guiding sheath of claim 2, wherein the at least one vent hole is configured to vent small amounts of the media in the inflated state of the balloon once the air in the media has been vented from the inflatable balloon.

18. The balloon guiding sheath of claim 2, wherein the at least one vent hole is configured to maintain the balloon in the inflated state at a relatively low pressure.

19. The balloon guiding sheath of claim 2, the at least one vent hole is formed by:
 bonding a wire between the inflatable balloon and the elongated sheath; and
 removing the wire prior to use.

* * * * *